(12) United States Patent
Rosen et al.

(10) Patent No.: US 10,203,246 B2
(45) Date of Patent: Feb. 12, 2019

(54) SYSTEMS AND METHODS FOR CALIBRATION OF A HANDHELD SPECTROMETER

(71) Applicant: Verifood, Ltd., Herzliya (IL)

(72) Inventors: Sagee Rosen, Netzer Sireni (IL); Dana Shemuly, Kfar-Sava (IL); Omer Keilaf, Kfar Saba (IL); Eli Zlatkin, Tel-Aviv (IL); Elad Heiman, Tel-Aviv (IL)

(73) Assignee: VERIFOOD, LTD., Herzliya (IL)

( * ) Notice: Subject to any disclaimer, the term of this patent is extended or adjusted under 35 U.S.C. 154(b) by 0 days.

(21) Appl. No.: 15/355,888

(22) Filed: Nov. 18, 2016

(65) Prior Publication Data

US 2017/0153142 A1  Jun. 1, 2017

Related U.S. Application Data

(60) Provisional application No. 62/258,362, filed on Nov. 20, 2015.

(51) Int. Cl.
  *G01J 3/02* (2006.01)
  *G01N 21/27* (2006.01)
  *G01J 3/28* (2006.01)

(52) U.S. Cl.
  CPC .......... *G01J 3/0275* (2013.01); *G01J 3/0205* (2013.01); *G01J 3/0264* (2013.01); *G01J 3/0272* (2013.01);
  (Continued)

(58) Field of Classification Search
  CPC ...... G01J 3/0275; G01J 3/0264; G01J 3/0272; G01J 3/0297; G01N 21/274
  See application file for complete search history.

(56) References Cited

U.S. PATENT DOCUMENTS

| 679,577 A | 7/1901 | Schaffner |
|---|---|---|
| 5,469,252 A | 11/1995 | Doles et al. |

(Continued)

FOREIGN PATENT DOCUMENTS

| CN | 1437702 A | 8/2003 |
|---|---|---|
| CN | 101501465 A | 8/2009 |

(Continued)

OTHER PUBLICATIONS

Acktar Advanced Coatings Website. Accessed Jun. 3, 2015. http://www.acktar.com/.

(Continued)

*Primary Examiner* — Dominic J Bologna
(74) *Attorney, Agent, or Firm* — Wilson, Sonsini, Goodrich & Rosati

(57) ABSTRACT

The spectrometer methods and apparatus disclosed herein provide improved accuracy and can better accommodate variability among spectrometer systems and associated components. In many instances one or more of a calibration cover, an accessory, or a spectrometer are each associated with a unique identifier and corresponding calibration data. The calibration data associated with the unique identifiers can be stored in a database used to determine spectral information from measurements of objects obtained with individual spectrometer devices. The spectrum of the object can be determined in response to the unique identifiers and associated calibration data in order to provide improved accuracy and decreased cost.

21 Claims, 41 Drawing Sheets

(52) U.S. Cl.
CPC ............... *G01J 3/0291* (2013.01); *G01J 3/28* (2013.01); *G01N 21/274* (2013.01)

(56) References Cited

U.S. PATENT DOCUMENTS

| | | | |
|---|---|---|---|
| 5,557,544 A * | 9/1996 | Simon | G01J 3/02 235/375 |
| 5,866,430 A * | 2/1999 | Grow | G01N 21/65 436/172 |
| 5,966,212 A | 10/1999 | Hendler et al. | |
| 6,031,233 A | 2/2000 | Levin et al. | |
| 6,031,619 A | 2/2000 | Wilkens et al. | |
| 6,038,022 A * | 3/2000 | Jones | B01L 9/00 356/244 |
| 6,069,696 A | 5/2000 | McQueen et al. | |
| 6,072,576 A | 6/2000 | McDonald et al. | |
| 6,212,312 B1 | 4/2001 | Grann et al. | |
| 6,333,501 B1 | 12/2001 | Labrenz | |
| 6,441,375 B1 | 8/2002 | Joseph et al. | |
| 6,456,373 B1 | 9/2002 | Wienecke et al. | |
| 6,483,583 B1 | 11/2002 | Wright et al. | |
| 6,615,142 B1 | 9/2003 | Hovde | |
| 6,639,666 B2 | 10/2003 | Li | |
| 6,700,661 B1 | 3/2004 | Cadell et al. | |
| 6,717,669 B2 | 4/2004 | Ruiz | |
| 6,836,325 B2 | 12/2004 | Maczura et al. | |
| 6,864,978 B1 | 3/2005 | Hazen et al. | |
| 6,958,479 B2 | 10/2005 | Burling-Claridge et al. | |
| 7,009,702 B2 | 3/2006 | Caruso et al. | |
| 7,038,774 B2 | 5/2006 | Hazen et al. | |
| 7,068,366 B2 | 6/2006 | Burk et al. | |
| 7,075,643 B2 | 7/2006 | Holub | |
| 7,084,974 B1 | 8/2006 | Barwicz et al. | |
| 7,145,650 B2 | 12/2006 | Wang et al. | |
| 7,151,600 B2 | 12/2006 | Imura | |
| 7,158,225 B2 | 1/2007 | Tedesco et al. | |
| 7,235,766 B2 | 6/2007 | Shur et al. | |
| 7,236,243 B2 | 6/2007 | Beecroft et al. | |
| 7,245,372 B2 | 7/2007 | Han | |
| 7,248,370 B2 | 7/2007 | Jones | |
| 7,251,037 B2 | 7/2007 | Jones | |
| 7,262,839 B2 | 8/2007 | Treado et al. | |
| 7,286,233 B2 | 10/2007 | Pizzi | |
| 7,339,665 B2 | 3/2008 | Imura | |
| 7,414,724 B2 | 8/2008 | Eckert et al. | |
| 7,420,663 B2 | 9/2008 | Wang et al. | |
| 7,426,446 B2 | 9/2008 | Hagler | |
| 7,433,042 B1 | 10/2008 | Cavanaugh et al. | |
| 7,436,511 B2 | 10/2008 | Ruchti et al. | |
| 7,489,396 B1 | 2/2009 | Vrhel et al. | |
| 7,528,957 B2 | 5/2009 | Lewis et al. | |
| 7,535,617 B2 | 5/2009 | Gupta et al. | |
| 7,649,627 B2 | 1/2010 | Yamamoto | |
| 7,667,740 B2 | 2/2010 | Hofer | |
| 7,697,136 B2 | 4/2010 | Imura | |
| 7,767,969 B2 | 8/2010 | Nagai et al. | |
| 7,805,319 B2 | 9/2010 | Badinelli | |
| 7,817,273 B2 | 10/2010 | Bahatt et al. | |
| 7,868,296 B2 | 1/2011 | Haran et al. | |
| 7,876,435 B2 | 1/2011 | Becker-Ross et al. | |
| 7,881,892 B2 | 2/2011 | Soyemi et al. | |
| 7,897,923 B2 | 3/2011 | Shelley et al. | |
| 7,907,282 B2 | 3/2011 | Coates | |
| 7,929,130 B2 | 4/2011 | Dirk | |
| 7,986,193 B2 | 7/2011 | Krah | |
| 7,999,933 B2 | 8/2011 | McClure | |
| 8,060,383 B2 | 11/2011 | Badinelli | |
| 8,125,633 B2 | 2/2012 | Whelan et al. | |
| 8,144,322 B2 | 3/2012 | Nagashima et al. | |
| 8,149,415 B2 | 4/2012 | Sanders et al. | |
| 8,169,607 B2 | 5/2012 | Sano et al. | |
| 8,169,608 B2 | 5/2012 | Sano et al. | |
| 8,247,774 B2 | 8/2012 | Chou et al. | |
| 8,269,174 B2 | 9/2012 | Gardner, Jr. et al. | |
| 8,274,739 B2 | 9/2012 | Lee et al. | |
| 8,284,401 B2 | 10/2012 | Choi et al. | |
| 8,330,945 B2 | 12/2012 | Choi et al. | |
| 8,462,420 B2 | 6/2013 | Lee et al. | |
| 8,477,305 B2 | 7/2013 | Shibayama et al. | |
| 8,526,002 B2 | 9/2013 | Deflores et al. | |
| 8,542,359 B2 | 9/2013 | Choi, II et al. | |
| 8,593,628 B2 | 11/2013 | Shimbo et al. | |
| 8,604,412 B2 | 12/2013 | Shibayama et al. | |
| 8,654,327 B2 | 2/2014 | Bohle et al. | |
| 8,665,440 B1 | 3/2014 | Kompaniets et al. | |
| 8,675,188 B2 | 3/2014 | Liu et al. | |
| 8,711,360 B2 | 4/2014 | Funamoto | |
| 8,711,362 B2 | 4/2014 | Funamoto | |
| 8,735,820 B2 | 5/2014 | Mertens | |
| 8,742,320 B2 | 6/2014 | Shibayama et al. | |
| 8,760,645 B2 | 6/2014 | Misener et al. | |
| 8,773,659 B2 | 7/2014 | McClure | |
| 8,786,854 B2 | 7/2014 | Miyazono | |
| 8,848,187 B2 | 9/2014 | Uematsu et al. | |
| 8,862,445 B2 | 10/2014 | Priore et al. | |
| 8,867,033 B2 | 10/2014 | Carron et al. | |
| 8,868,387 B2 | 10/2014 | Den Boef et al. | |
| 8,873,046 B2 | 10/2014 | Miyazono | |
| 8,937,717 B2 | 1/2015 | Preston et al. | |
| 8,976,357 B2 | 3/2015 | Uematsu et al. | |
| 9,030,662 B2 | 5/2015 | Lee et al. | |
| 9,060,113 B2 | 6/2015 | Rhoads et al. | |
| 9,063,011 B2 | 6/2015 | Chen et al. | |
| 9,074,933 B2 | 7/2015 | Yokino et al. | |
| 9,128,055 B2 | 9/2015 | Sekino et al. | |
| 9,163,986 B2 | 10/2015 | Bouckaert | |
| 9,173,508 B2 | 11/2015 | Tornwall et al. | |
| 9,182,280 B1 | 11/2015 | Gardner et al. | |
| 9,234,800 B2 | 1/2016 | Kawamata et al. | |
| 9,239,264 B1 | 1/2016 | Demers | |
| 9,291,504 B2 | 3/2016 | Goldring et al. | |
| 9,297,821 B2 | 3/2016 | Walter et al. | |
| 9,301,626 B2 | 4/2016 | Tornwall et al. | |
| 9,310,564 B2 | 4/2016 | Martinelli et al. | |
| 9,377,396 B2 | 6/2016 | Goldring et al. | |
| 9,383,258 B2 | 7/2016 | Goldring et al. | |
| 9,383,308 B2 | 7/2016 | Bradley et al. | |
| 9,395,244 B2 | 7/2016 | Kurokawa et al. | |
| 9,417,180 B2 | 8/2016 | Seo et al. | |
| 9,448,114 B2 | 9/2016 | Goldring et al. | |
| 9,448,165 B2 | 9/2016 | Gulati et al. | |
| 9,453,794 B2 | 9/2016 | Gulati et al. | |
| 9,464,934 B2 | 10/2016 | Priore et al. | |
| 9,488,468 B2 | 11/2016 | Tsujii et al. | |
| 9,488,523 B2 | 11/2016 | Yokino et al. | |
| 9,500,523 B2 | 11/2016 | Goldring et al. | |
| 9,508,765 B2 | 11/2016 | Owa et al. | |
| 9,518,917 B2 | 12/2016 | Scherer et al. | |
| 9,546,902 B2 | 1/2017 | Kovacich et al. | |
| 9,546,904 B2 | 1/2017 | Pawluczyk et al. | |
| 9,557,220 B2 | 1/2017 | Yasui et al. | |
| 9,562,848 B2 | 2/2017 | Goldring et al. | |
| 9,568,363 B2 | 2/2017 | Yu et al. | |
| 9,574,942 B2 | 2/2017 | Goldring et al. | |
| 9,587,982 B2 | 3/2017 | Goldring et al. | |
| 2001/0009972 A1 | 7/2001 | Doi et al. | |
| 2002/0022273 A1* | 2/2002 | Empedocles | B01L 3/5025 436/171 |
| 2002/0039186 A1 | 4/2002 | Rosenberg et al. | |
| 2002/0131047 A1 | 9/2002 | Zarrabian et al. | |
| 2002/0145728 A1 | 10/2002 | Adams et al. | |
| 2002/0163641 A1 | 11/2002 | Shroder | |
| 2002/0191127 A1 | 12/2002 | Roberts et al. | |
| 2003/0122080 A1 | 7/2003 | Burling-Claridge et al. | |
| 2004/0019462 A1 | 1/2004 | Gehrlein et al. | |
| 2004/0036871 A1* | 2/2004 | McCallum | G01J 3/28 356/326 |
| 2004/0136577 A1 | 7/2004 | Rao et al. | |
| 2004/0213459 A1 | 10/2004 | Ishimaru et al. | |
| 2005/0117151 A1 | 6/2005 | Han | |
| 2005/0128477 A1 | 6/2005 | Caruso et al. | |
| 2005/0149598 A1 | 7/2005 | Mendlovic et al. | |
| 2005/0151975 A1 | 7/2005 | Melnyk | |
| 2005/0196046 A1 | 9/2005 | Hudnut et al. | |

(56) References Cited

U.S. PATENT DOCUMENTS

| | | |
|---|---|---|
| 2006/0086901 A1 | 4/2006 | Price et al. |
| 2006/0124656 A1 | 6/2006 | Popovich, Jr. et al. |
| 2006/0132760 A1* | 6/2006 | Imura .................... G01J 3/28 356/243.8 |
| 2006/0146315 A1 | 7/2006 | Treado |
| 2006/0279732 A1 | 12/2006 | Wang et al. |
| 2006/0280096 A1 | 12/2006 | Riley et al. |
| 2007/0230932 A1 | 10/2007 | Tanaka et al. |
| 2008/0061236 A1 | 3/2008 | Meredith et al. |
| 2008/0073510 A1 | 3/2008 | Finlay |
| 2008/0112853 A1 | 5/2008 | Hall |
| 2008/0137328 A1 | 6/2008 | Lee et al. |
| 2008/0204578 A1 | 8/2008 | Scheuch et al. |
| 2008/0265146 A1 | 10/2008 | Coates |
| 2008/0277625 A1 | 11/2008 | Nakamura et al. |
| 2008/0297379 A1 | 12/2008 | Yang et al. |
| 2008/0297791 A1 | 12/2008 | Imura |
| 2009/0051910 A1 | 2/2009 | Imura |
| 2009/0201577 A1 | 8/2009 | Laplante et al. |
| 2009/0294637 A1 | 12/2009 | Kusano et al. |
| 2010/0080351 A1 | 4/2010 | Hession-Kunz et al. |
| 2010/0085537 A1 | 4/2010 | Ramella-Roman et al. |
| 2010/0110442 A1 | 5/2010 | Adibi et al. |
| 2010/0128370 A1 | 5/2010 | Chen et al. |
| 2010/0134794 A1 | 6/2010 | Odegard et al. |
| 2010/0165337 A1 | 7/2010 | Dirk |
| 2010/0191493 A1 | 7/2010 | Brown et al. |
| 2010/0201979 A1 | 8/2010 | Momtahan et al. |
| 2010/0271352 A1 | 10/2010 | Nakano et al. |
| 2010/0284005 A1 | 11/2010 | Malinen et al. |
| 2010/0292581 A1 | 11/2010 | Howard et al. |
| 2010/0309454 A1 | 12/2010 | Zhang |
| 2011/0037975 A1 | 2/2011 | McClure |
| 2011/0255745 A1 | 10/2011 | Hodder et al. |
| 2011/0261252 A1 | 10/2011 | Chen |
| 2011/0318717 A1 | 12/2011 | Adamowicz |
| 2012/0018829 A1 | 1/2012 | Beck et al. |
| 2012/0019819 A1 | 1/2012 | Messerchmidt |
| 2012/0053426 A1 | 3/2012 | Webster et al. |
| 2012/0088486 A1 | 4/2012 | Messerchmidt |
| 2012/0099102 A1 | 4/2012 | Bello |
| 2012/0286046 A1 | 11/2012 | Ciurczak et al. |
| 2013/0021611 A1 | 1/2013 | Tsurutani |
| 2013/0107260 A1 | 5/2013 | Nozawa |
| 2013/0155402 A1 | 6/2013 | Walton et al. |
| 2013/0182250 A1 | 7/2013 | McClure |
| 2013/0258341 A1 | 10/2013 | Day et al. |
| 2014/0046630 A1 | 2/2014 | Smith et al. |
| 2014/0052555 A1 | 2/2014 | MacIntosh |
| 2014/0064479 A1 | 3/2014 | Manikandan et al. |
| 2014/0168636 A1 | 6/2014 | Funamoto et al. |
| 2014/0293091 A1 | 10/2014 | Rhoads et al. |
| 2014/0320858 A1 | 10/2014 | Goldring et al. |
| 2014/0333932 A1 | 11/2014 | Uematsu et al. |
| 2015/0036138 A1 | 2/2015 | Watson et al. |
| 2015/0055132 A1 | 2/2015 | Ricketts et al. |
| 2015/0062577 A1 | 3/2015 | Hartwell et al. |
| 2015/0103354 A1 | 4/2015 | Saptari et al. |
| 2015/0108333 A1 | 4/2015 | Bouckaert |
| 2015/0116707 A1 | 4/2015 | Tatsuda |
| 2015/0119661 A1 | 4/2015 | Gilbert et al. |
| 2015/0153225 A1 | 6/2015 | Baudelet |
| 2015/0204833 A1 | 7/2015 | O'Brien et al. |
| 2015/0292948 A1 | 10/2015 | Goldring et al. |
| 2015/0300879 A1 | 10/2015 | Goldring et al. |
| 2015/0323383 A1* | 11/2015 | Pastore ............. G01J 3/0264 356/326 |
| 2015/0369725 A1 | 12/2015 | Carvalho et al. |
| 2016/0018260 A1 | 1/2016 | Samuels |
| 2016/0033328 A1 | 2/2016 | Walters |
| 2016/0091369 A1 | 3/2016 | Sakurai et al. |
| 2016/0103069 A1 | 4/2016 | Umapathy et al. |
| 2016/0223400 A1 | 8/2016 | Carron et al. |
| 2016/0231171 A1 | 8/2016 | Assefa et al. |
| 2016/0238449 A1 | 8/2016 | Goldring et al. |
| 2016/0245700 A1 | 8/2016 | Uematsu et al. |
| 2016/0258813 A1 | 9/2016 | Kuri |
| 2016/0263910 A1 | 9/2016 | Kanai et al. |
| 2016/0282182 A1 | 9/2016 | Kanai et al. |
| 2016/0290863 A1 | 10/2016 | Goldring et al. |
| 2016/0299004 A1 | 10/2016 | Thamm |
| 2016/0299061 A1 | 10/2016 | Goldring et al. |
| 2016/0305820 A1 | 10/2016 | Zollars et al. |
| 2016/0313184 A1 | 10/2016 | Owechko |
| 2016/0334274 A1 | 11/2016 | Xu |
| 2016/0356646 A1 | 12/2016 | Wiegand et al. |
| 2016/0356647 A1 | 12/2016 | Wiegand et al. |
| 2016/0356704 A1 | 12/2016 | Kim et al. |
| 2017/0003167 A1 | 1/2017 | Ave |
| 2017/0027447 A1 | 2/2017 | Sutin et al. |
| 2017/0038257 A1 | 2/2017 | Liu et al. |
| 2017/0160131 A1 | 6/2017 | Goldring et al. |
| 2017/0234729 A1 | 8/2017 | Goldring et al. |

FOREIGN PATENT DOCUMENTS

| | | |
|---|---|---|
| JP | H0792022 A | 4/1995 |
| JP | 2004294361 A | 10/2004 |
| JP | 2005148018 A | 6/2005 |
| JP | 2007218878 A | 8/2007 |
| JP | 2008286522 A | 11/2008 |
| JP | 2009104547 A | 5/2009 |
| JP | 2011198801 A | 10/2011 |
| WO | WO-9953350 A1 | 10/1999 |
| WO | WO-2005008198 A2 | 1/2005 |
| WO | WO-2010027982 A2 | 3/2010 |
| WO | WO-2010036906 A1 | 4/2010 |
| WO | WO-2013065035 A1 | 5/2013 |
| WO | WO-2013082272 A1 | 6/2013 |
| WO | WO-2013106307 A1 | 7/2013 |
| WO | WO-2013148461 A1 | 10/2013 |
| WO | WO-2013150290 A1 | 10/2013 |
| WO | WO-2013162850 A1 | 10/2013 |
| WO | WO-2013163268 A1 | 10/2013 |
| WO | WO-2013165887 A1 | 11/2013 |
| WO | WO-2014014534 A2 | 1/2014 |
| WO | WO-2014033783 A1 | 3/2014 |
| WO | WO-2014014534 A3 | 4/2014 |
| WO | WO-2014064447 A1 | 5/2014 |
| WO | WO-2014102629 A1 | 7/2014 |
| WO | WO-2014129305 A1 | 8/2014 |
| WO | WO-2014139003 A1 | 9/2014 |
| WO | WO-2014192007 A1 | 12/2014 |
| WO | WO-2015009602 A1 | 1/2015 |
| WO | WO-2015015493 A2 | 2/2015 |
| WO | WO-2015015493 A3 | 3/2015 |
| WO | WO-2015038372 A1 | 3/2015 |
| WO | WO-2015042617 A1 | 3/2015 |
| WO | WO-2015058166 A2 | 4/2015 |
| WO | WO-2015058166 A3 | 6/2015 |
| WO | WO-2015101992 A2 | 7/2015 |
| WO | WO-2015101992 A3 | 9/2015 |
| WO | WO-2015138028 A2 | 9/2015 |
| WO | WO-2015138028 A3 | 11/2015 |
| WO | WO-2016022283 A1 | 2/2016 |
| WO | WO-2016033224 A1 | 3/2016 |
| WO | WO-2016059946 A1 | 4/2016 |
| WO | WO-2016124659 A1 | 8/2016 |
| WO | WO-2016196727 A2 | 12/2016 |
| WO | WO-2016196727 A3 | 1/2017 |

OTHER PUBLICATIONS

Anoplate Website. Accessed Jun. 3, 2015. http://www.anoplate.com/capabilities/anoblack_ni.html.

Avian Technologies Website. Accessed Jun. 3, 2015. http://www.aviantechnologies.com/products/coatings/diffuse_black.php.

European search report and search opinion dated Feb. 7, 2017 for EP Application No. 14831451.1.

European search report and search opinion dated Jul. 24, 2015 for EP Application No. 12845773.6.

European search report and search opinion dated Aug. 7, 2017 for EP Application No. 15733267.7.

(56) References Cited

OTHER PUBLICATIONS

"Interference Filter Handbook," published by JDS Uniphase (Second Edition), Sep. 2006, p. 195-202 and 213-214.
International search report and written opinion dated Jan. 26, 2015 for PCT Application No. IL2014/050688.
International search report and written opinion dated Mar. 22, 2013 for PCT Application No. IL2012/000367.
International search report and written opinion dated Jul. 14, 2015 for PCT Application No. PCT/IL2015/050002.

* cited by examiner

SYSTEMS AND METHODS FOR CALIBRATION OF A HANDHELD SPECTROMETER

CROSS-REFERENCE

The present application is a non-provisional of, and claims the benefit of, U.S. Provisional Patent Application 62/258,362, filed on Nov. 20, 2015, the entire contents of which are incorporated herein by reference.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND OF THE INVENTION

Spectrometry systems are commonly used to measure characteristics of the interaction between light and matter. Spectrometer systems can measure the amount of light reflected from a sample, and particularly the dependence of light reflection on the wavelength of light. Alternatively, spectrometer systems may measure the amount of light transmission through a material and particularly the dependence of light transmission on the wavelength of light. Some spectrometer systems may measure the amount of scattering of light by a material and particularly the dependence of light scattering on the wavelength of light.

A spectrometer system may include one or more of an illumination source, a light guiding element, a reflective element and a detecting element. The various elements in the spectrometer system may affect the measured data. In order to decrease the variations in measured spectra of a sample due to contributions from spectrometer system elements, calibration can be used to compensate for the variances in the spectrometer system.

In some cases, even relatively small differences among spectrometer systems or any elements thereof, such as various accessories, optical components, or calibration elements, can be relevant. Such system-to-system variations can be particularly relevant when spectral sample data is collected from and shared by a variety of similar spectrometer systems. In such cases, calibrating each spectrometer system with a single, common calibration reference may not be practical, and manufacturing highly matching calibration references for each spectrometer system may be costly.

In light of the above, it would be beneficial to provide systems and methods for improving the accuracy of spectrometer systems that accommodates for variability of the spectrometers and associated components, in a practical and economical manner.

SUMMARY OF THE INVENTION

The spectrometer methods and apparatus disclosed herein provide improved accuracy and can better accommodate variability among spectrometer systems and associated components. In many instances one or more of a calibration cover, an accessory, or a spectrometer are each associated with a unique identifier and corresponding calibration data. The calibration data associated with the unique identifiers can be stored in a database used to determine spectral information from measurements of objects obtained with individual spectrometer devices. The spectrum of the object can be determined in response to the unique identifiers and associated calibration data in order to provide improved accuracy and decreased cost.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative instances, in which the principles of the invention are utilized, and the accompanying drawings of which:

FIG. 17 shows an exploded assembly diagram of an.

DETAILED DESCRIPTION OF THE INVENTION

The spectrometer methods and apparatus disclosed herein are well suited for combination with many types of spectrometers. The serialization disclosed herein can be used with many types of spectrometers and accessories.

A spectrometer system may comprise one or more accessories used to control the sample position or state relative to the spectrometer. For example, an accessory may comprise a cover that is configured to block the ambient light from illuminating the sample and also provide a well-defined spatial configuration of the sample relative to the spectrometer. An accessory may comprise sample container such as an accessory for measuring a pill, wherein the sample is placed inside a cavity to position the sample at a known orientation and distance with respect to the spectrometer. An accessory may comprise a liquid measurement accessory configured to provide a well-defined light path from the illumination module of the spectrometer to the optical module of the spectrometer, through a liquid sample.

As used herein like characters identify like elements.

The examples disclosed herein can be combined in one or more of many ways to provide improved spectrometer methods and apparatus.

As used herein like characters refer to like elements.

As used herein "light" encompasses electromagnetic radiation having wavelengths in one or more of the ultraviolet, visible, or infrared portions of the electromagnetic spectrum.

The dimensions of an optical beam as described herein can be determined in one or more of many ways. The size of the beam may comprise a full width half maximum of the beam, for example. The measurement beam may comprise blurred edges, and the measurement area of the beam defining the measurement area of the sample may comprise a portion of the beam extending beyond the full width half maximum of the beam, for example. The dimensions of the aiming beam can be similarly determined.

Figure 1:
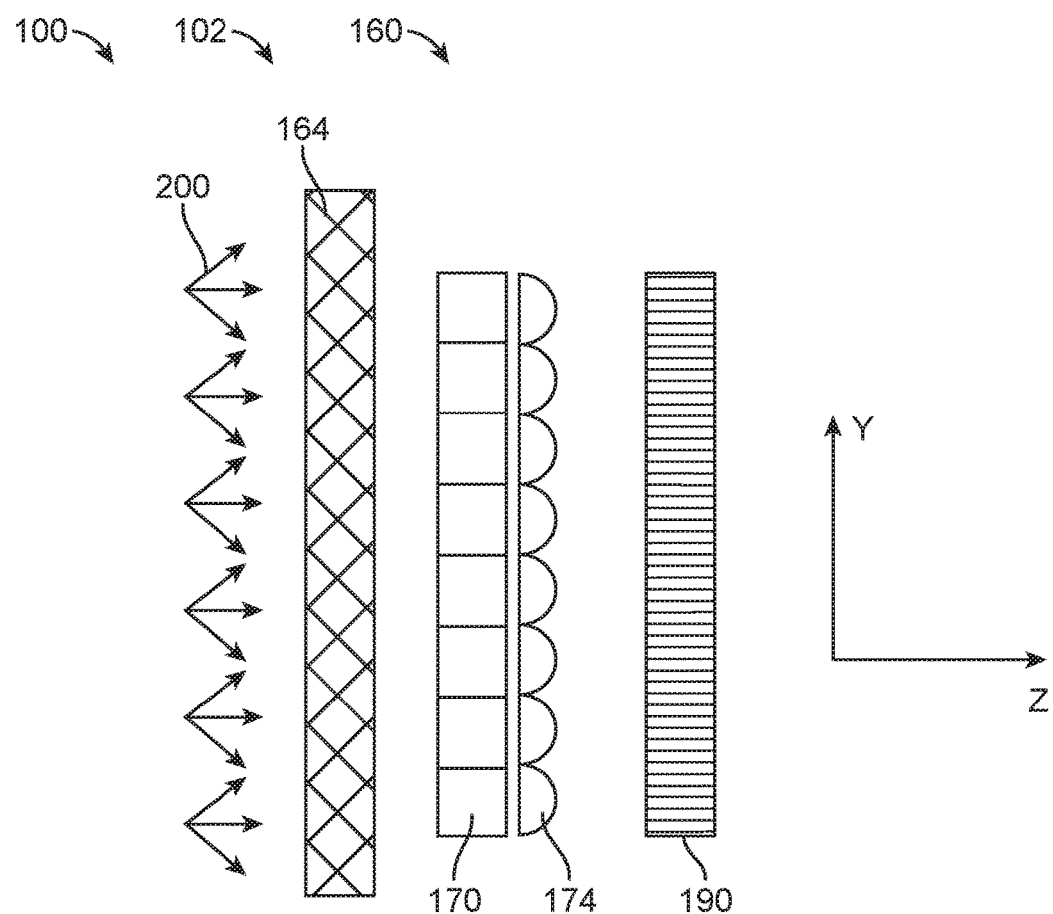
FIG. 1 shows schematic diagrams of the optical layout.

Reference is now made to FIG. 1, which illustrates non-limiting configurations of the compact spectrometer system 100 herein disclosed. As illustrated the system comprises a diffuser 164, a filter matrix 170, a lens array 174 and a detector 190.

The spectrometer can have a size and weight such that the spectrometer can be held by a user with only one hand. The spectrometer can have a size and weight such that the spectrometer can be portable. The spectrometer can have a weight of about 1 gram (g), 5 g, 10 g, 15 g, 20 g, 25 g, 30 g, 35 g, 40 g, 45 g, 50 g, 55 g, 60 g, 65 g, 70 g, 80 g. 85 g, 90 g, 95 g, 100 g, 110 g, 120 g, 130 g, 140 g, 150 g, 160 g, 170 g, 180 g, 190 g, or 200 g. The spectrometer can have a weight less than 1 g. The spectrometer can have a weight greater than 200 g. The spectrometer can have a weight that is between any of the two values given above. For example, the spectrometer can have a weight within a range from about 1 g to about 200 g, about 1 g to about 100 g, about 5 g to about 50 g, about 5 g to about 40 g, about 10 g to about 40 g, about 10 g to about 30 g, or about 20 g to about 30 g.

The spectrometer can have a total volume of at most about 200 $cm^3$, 150 $cm^3$, 100 $cm^3$, 95 $cm^3$, 90 $cm^3$, 85 $cm^3$, 80 $cm^3$, 75 $cm^3$, 70 $cm^3$, 65 $cm^3$, 60 $cm^3$, 55 $cm^3$, 50 $cm^3$, 45 $cm^3$, 40 $cm^3$, 35 $cm^3$, 30 $cm^3$, 25 $cm^3$, 20 $cm^3$, 15 $cm^3$, 10 $cm^3$, 5 $cm^3$, or 1 $cm^3$. The spectrometer can have a volume less than 1 $cm^3$. The spectrometer can have a volume greater than 100 $cm^3$. The spectrometer can have a volume that is between any of the two values given above. For example, the spectrometer may have a volume within a range from about 1 $cm^3$ to about 200 $cm^3$, about 40 $cm^3$ to about 200 $cm^3$, about 60 $cm^3$ to about 150 $cm^3$, about 80 $cm^3$ to about 120 $cm^3$, about 80 $cm^3$ to about 100 $cm^3$, or about 90 $cm^3$.

The spectrometer shape can comprise a rectangular prism, cylinder, or other three-dimensional shape. The spectrometer can have a length of at most about 500 mm, 400 mm, 300 mm, 200 mm, 250 mm, 100 mm, 95 mm, 90 mm, 85 mm, 80 mm, 75 mm, 70 mm, 65 mm, 60 mm, 55 mm, 50 mm, 45 mm, 40 mm, 35 mm, 30 mm, 25 mm, 20 mm, 15 mm, 10 mm, or 5 mm. The spectrometer can have a length less than 5 mm. The spectrometer can have a length greater than 500 mm. The spectrometer can have a length that is between any of the two values given above. For example, the spectrometer have a length within a range from about 10 mm to about 100 mm, about 25 mm to about 75 mm, or about 50 mm to about 70 mm. The spectrometer can have a width of at most about 500 mm, 400 mm, 300 mm, 200 mm, 250 mm, 100 mm, 95 mm, 90 mm, 85 mm, 80 mm, 75 mm, 70 mm, 65 mm, 60 mm, 55 mm, 50 mm, 45 mm, 40 mm, 35 mm, 30 mm, 25 mm, 20 mm, 15 mm, 10 mm, or 5 mm. The spectrometer can have a width less than 5 mm. The spectrometer can have a width greater than 500 mm. The spectrometer can have a width that is between any of the two values given above. For example, the spectrometer may have a width within a range from about 10 mm to about 75 mm, about 20 mm to about 60 mm, or about 30 mm to about 50 mm. The spectrometer can have a height of at most about 500 mm, 400 mm, 300 mm, 200 mm, 250 mm, 100 mm, 95 mm, 90 mm, 85 mm, 80 mm, 75 mm, 70 mm, 65 mm, 60 mm, 55 mm, 50 mm, 45 mm, 40 mm, 35 mm, 30 mm, 25 mm, 20 mm, 15 mm, 10 mm, or 5 mm. The spectrometer can have a height less than 5 mm. The spectrometer can have a height greater than 500 mm. The spectrometer can have a height that is between any of the two values given above. For example, the spectrometer may have a height within a range from about 1 mm to about 50 mm, about 5 mm to about 40 mm, or about 10 mm to about 20 mm. The spectrometer may, for example, have dimensions within a range from about 0.1 cm×0.1 cm×2 cm to about 5 cm×5 cm×10 cm. In the case of a cylindrical spectrometer the spectrometer can have a radius of at most about 500 mm, 400 mm, 300 mm, 200 mm, 250 mm, 100 mm, 95 mm, 90 mm, 85 mm, 80 mm, 75 mm, 70 mm, 65 mm, 60 mm, 55 mm, 50 mm, 45 mm, 40 mm, 35 mm, 30 mm, 25 mm, 20 mm, 15 mm, 10 mm, or 5 mm. The spectrometer can have a radius less than 5 mm. The spectrometer can have a radius greater than 500 mm. The spectrometer can have a radius that is between any of the two values given above.

One or more of the components of the spectrometer can be powered by a battery. The battery can be on-board the spectrometer. The battery can have a weight of at most about 50 g, 45 g, 40 g, 35 g, 30 g, 25 g, 20 g, 15 g, 10 g, 5 g, 1 g, or 0.1 g. The battery can have a weight less than 0.1 g. The battery can have a weight greater than 50 g. The battery can have a weight that is between any of the two values given above. For example, the batter may have a weight that is within a range from about 2 g to about 6 g, about 3 g to about 5 g, or about 4 g.

The compact spectrometer 102 may have an optical resolution of less than 10 nm, less than 5 nm, less than 4 nm, less than 3 nm, less than 2 nm, less than 1 nm, less than 0.5 nm, or less than 0.1 nm. The spectrometer can have an optical resolution that is between any of the two values given above. For example, the spectrometer may have an optical resolution that is within a range from about 0.1 nm to about 100 nm, about 1 nm to about 50 nm, about 1 nm to about 10 nm, or about 2 nm to about 5 nm. The spectrometer may have an optical resolution of approximately 5 nm, which is equivalent to approximately 100 cm$^{-1}$ at a wavelength of about 700 nm and equivalent to approximately 40 cm$^{-1}$ at a wavelength of about 1100 nm. The spectrometer may have an optical resolution that is between 100 cm$^{-1}$ and 40 cm$^{-1}$. The spectrometer can have a temporal signal-to-noise ratio (SNR) of about 1000 for a single sensor reading (without averaging, at maximum spectral resolution) for a wavelength of about 1000 nm, or an SNR of about 2500 for a wavelength of about 850 nm. The compact spectrometer, when configured to perform algorithmic processing or correction of measured spectral data, may be able to detect changes in normalized signals in the order of about $1\times10^{-3}$ to about $1\times10^{-4}$, or about $5\times10^{-4}$. The light source of the illumination module may be configured to have a stabilization time of less than 1 min, less than 1 s, less than 1 ms, or about 0 s.

The spectrometer system can comprise a plurality of optical filters of filter matrix 170. The optical filter can be of any type known in the art. Non-limiting examples of suitable optical filters include Fabry-Perot (FP) resonators, cascaded FP resonators, and interference filters. For example, a narrow bandpass filter (≤10 nm) with a wide blocking range outside of the transmission band (at least 200 nm) can be used. The center wavelength (CWL) of the filter can vary with the incident angle of the light impinging upon it.

In some instances, the central wavelength of the central band can vary by 10 nm or more, such that the effective range of wavelengths passed with the filter is greater than the bandwidth of the filter. In some instances, the central wavelength varies by an amount greater than the bandwidth of the filter. For example, the bandpass filter can have a bandwidth of no more than 10 nm and the wavelength of the central band can vary by more than 10 nm across the field of view of the sensor.

In some instances, the spectrometer system may comprise a detector 190, which may comprise an array of sensors. In some instances, the detector can be capable of detecting light in the wavelength range of interest. The compact spectrometer system disclosed herein can be used from the UV to the IR, depending on the nature of the spectrum being obtained and the particular spectral properties of the sample being tested. In some instances, a detector that is capable of measuring intensity as a function of position (e.g. an array detector or a two-dimensional image sensor) can be used.

In some cases the spectrometer does not comprise a cylindrical beam volume hologram (CVBH).

In some cases, the spectrometer system can comprise a diffuser. When the light emanating from the sample is not sufficiently diffuse, a diffuser can be placed in front of other elements of the spectrometer. Collimated (or partially collimated light) can impinge on the diffuser, which then produces diffuse light which then impinges on other aspects of the spectrometer, e.g. an optical filter.

In some instances, the spectrometer system can comprise a filter matrix. The filter matrix can comprise one or more filters, for example a plurality of filters. The filter matrix can comprise more than 2, 10, 50, or 100 filters (also referred to as sub-filters). The use of a single filter can limit the spectral range available to the spectrometer. For example, if the angle of incidence of light is larger than 30°, the system may not produce a signal of sufficient intensity due to lens aberrations and the decrease in the efficiency of the detector at large angles. For an angular range of 30° and an optical filter CWL of ~850 nm, the spectral range available to the spectrometer can be about 35 nm, for example. As this range can be insufficient for some spectroscopy based applications, instances with larger spectral ranges may comprise an optical filter matrix composed of a plurality of sub-filters. Each sub-filter can have a different CWL and thus covers a different part of the optical spectrum. The sub-filters can be configured in one or more of many ways and be tiled in two dimensions, for example.

Depending on the number of sub-filters, the wavelength range accessible to the spectrometer can reach hundreds of nanometers. In configurations comprising a plurality of sub-filters, the approximate Fourier transforms formed at the image plane (i.e. one per sub-filter) overlap, and the signal obtained at any particular pixel of the detector can result from a mixture of the different Fourier transforms.

In some cases, the filter matrix can be arranged in a specific order to inhibit cross talk on the detector of light emerging from different filters and to minimize the effect of stray light. For example, if the matrix is composed of 3×4 filters then there are 2 filters located at the interior of the matrix and 10 filters at the periphery of the matrix. The 2 filters at the interior can be selected to be those at the edges of the wavelength range. Without being bound by a particular theory the selected inner filters may experience the most spatial cross-talk but be the least sensitive to cross-talk spectrally.

The spectrometer system can comprise a detector 190. The detector can be sensitive to one or more of ultraviolet wavelengths of light, visible wavelengths of light, or infrared wavelengths of light.

The detector can be located in a predetermined plane. The predetermined plane can be the focal plane of the lens array. Light of different wavelengths (X1, X2, X3, X4, etc.) can arrive at the detector as a series of substantially concentric circles of different radii proportional to the wavelength. The relationship between the wavelength and the radius of the corresponding circle may not be linear.

The detector can be configured to receive non-continuous spectra, for example a non-continuous spectra that can be unlike a spectra that a dispersive element would create. The non-continuous spectra can be missing parts of the spectrum. The non-continuous spectrum can have the wavelengths of the spectra at least in part spatially out of order, for example. In some cases, first short wavelengths can contact the detector near longer wavelengths, and second short wavelengths can contact the detector at distances further away from the first short wavelengths than the longer wavelengths.

The detector may comprise a plurality of detector elements, such as pixels for example. Each detector element may be configured so as to receive signals of a broad spectral range. The spectral range received on the first and second pluralities of detector elements may extend at least from about 10 nm to about 400 nm. In some instances, a spectral range received on the first and second pluralities of detector elements may extend at least from about 10 nm to about 700 nm. In many cases, the spectral range received on the first and second pluralities of detector elements may extend at least from about 10 nm to about 1600 nm. In some cases, the spectral range received on the first and second pluralities of detector elements may extend at least from about 400 nm to about 1600 nm. In some cases, the spectral range received on the first and second pluralities of detector elements may extend at least from about 700 nm to about 1600 nm.

In some cases, the lens array, the filter matrix, and the detector may not be centered on a common optical axis. In many instances the lens array, the filter matrix, and the detector are aligned on a common optical axis.

In many cases, the principle of operation of compact spectrometer comprises one or more of the following attributes. Light impinges upon the diffuser. The light next impinges upon the filter matrix at a wide range of propagation angles and the spectrum of light passing through the sub-filters is angularly encoded. The angularly encoded light then passes through the lens array (e.g. Fourier transform focusing elements) which performs (approximately) a spatial Fourier transform of the angle-encoded light, transforming it into a spatially-encoded spectrum. Finally the light reaches the detector. The location of the detector element relative to the optical axis of a lens of the array corresponds to the wavelength of light, and the wavelength of light at a pixel location can be determined based on the location of the pixel relative to the optical axis of the lens of the array. The intensity of light recorded by the detector element such as a pixel as a function of position (e.g. pixel number or coordinate reference location) on the sensor corresponds to the resolved wavelengths of the light for that position.

In some cases, an additional filter can be placed in front of the compact spectrometer system in order to block light outside of the spectral range of interest (i.e. to prevent unwanted light from reaching the detector).

In instances in which the spectral range covered by the optical filters is insufficient, additional sub-filters with differing CWLs can be used.

In some cases, one or more shutters can allow for the inclusion or exclusion of light from part of the system. For example shutters can be used to exclude particular sub-filters. Shutters may also be used to exclude individual lens.

In some instances, the measurement of the sample can be performed using scattered ambient light.

In many instances, the spectrometer system can comprise a light source. The light source can be of any type (e.g. laser or light-emitting diode) known in the art appropriate for the spectral measurements to be made. In some cases the light source can emit light from 350 nm to 1100 nm. The wavelength(s) and intensity of the light source will depend on the particular use to which the spectrometer will be put. In some cases, the light source can emit light from 0.1 mW to 500 mW Because of its small size and low complexity, the compact spectrometer system herein disclosed can be integrated into a mobile communication device such as a cellular telephone. It can either be enclosed within the device itself, or mounted on the device and connected to it by wired or wireless means for providing power and a data link. By incorporating the spectrometer system into a mobile device, the spectra obtained can be uploaded to a remote location, analysis can be performed there, and the user notified of the results of the analysis. The spectrometer system can also be equipped with a GPS device and/or altimeter so that the location of the sample being measured can be reported. Further non-limiting examples of such components include a camera for recording the visual impression of the sample and sensors for measuring such environmental variables as temperature and humidity.

Because of its small size and low cost, the spectrometer system herein disclosed can also be integrated into kitchen appliances such as ovens (e.g. microwave ovens), food processors, toilets refrigerators etc. The user can then make a determination of the safety of the ingredients in real time during the course of food storage and preparation.

In many instances, the spectrometer can also include a power source (e.g. a battery or power supply). In some cases, the spectrometer can be powered by a power supply from a consumer hand held device (e.g. a cell phone). In some cases, the spectrometer can have an independent power supply. In some instances a power supply from the spectrometer can supply power to a consumer hand held device.

In many instances, the spectrometer can comprise a processing and control unit. In some cases, the spectrometer may not analyze the data collected, and the spectrometer can relay data to a remote processing and control unit, such as a back end server. Alternatively or in combination, the spectrometer may partially analyze the data prior to transmission to the remote processing and control unit. The remote processing and control unit can be coupled to the spectrometer with a consumer hand held device (e.g. a cell phone). The remote processing and control unit can be a cloud based system which can transmit analyzed data or results to a user. In some cases, a hand held device can be configured to receive analyzed data and can be associated with the spectrometer. The association can be through a physical connection or wireless communication, for example.

The spectrometers as described herein can be adapted, with proper choice of light source, detector, and associated optics, for a use with a wide variety of spectroscopic techniques. Non-limiting examples include Raman, fluorescence, and IR or UV-VIS reflectance and absorbance spectroscopies. Because, as described above, compact spectrometer system can separate a Raman signal from a fluorescence signal, in some cases, the same spectrometer can be used for both spectroscopies.

In some instances the spectrometer system can come equipped with a memory with a database of spectral data stored therein and a microprocessor with analysis software programmed with instructions. In some cases, the spectrometer system can be in communication with a computer memory having a database of spectral data stored therein and a microprocessor with analysis software programmed in. The memory can be volatile or non-volatile in order to store the user's own measurements in the memory. The database and/or all or part of the analysis software can be stored remotely, and the spectrometer system can communicate with the remote memory via a network (e.g. a wireless network) by any appropriate method. Alternatively, the database of spectral data can be provided with a computer located near the spectrometer, for example in the same room.

In some instances in which the database is located remotely, the data base can be updated often at regular intervals, for example continuously. In these instances, each measurement made by a user of the spectrometer can increase the quality and reliability of future measurements made by any user.

Once a spectrum is then obtained it can be analyzed. In some cases, the analysis may not be contemporaneous. In some cases the analysis can occur in real time. The spectrum can be analyzed using any appropriate analysis method. Non-limiting examples of spectral analysis techniques that can be used include Principal Components Analysis, Partial Least Squares analysis, and the use of a neural network algorithm to determine the spectral components.

An analyzed spectrum can determine whether a complex mixture being investigated contains a spectrum associated with components. The components can be, e.g., a substance, mixture of substances, or microorganisms.

The intensity of these components in the spectrum can be used to determine whether a component is at a certain concentration, e.g. whether their concentration of an undesirable component is high enough to be of concern. Non-limiting examples of such substances include toxins, decomposition products, or harmful microorganisms. In some instances, if it is deemed likely that the sample is not fit for consumption, the user can be provided with a warning.

In some instances, the spectrometer can be connected to a communication network that allows users to share the information obtained in a particular measurement. An updatable database located in the "cloud" (i.e. the distributed network) constantly receives the results of measurements made by individual users and updates itself in real time, thus enabling each successive measurement to be made with greater accuracy and confidence as well as expanding the number of substances for which a spectral signature is available.

In various instances, the conversion of the raw intensity data to a spectrum may be performed either locally (with a processor and software supplied with the spectrometer system) or remotely. Heavier calculations for more complicated analyses for example can be performed remotely.

In instances that incorporate remote data analysis, the data transferred to the remote system may include one or more of raw detector data; pre-processed detector data or post-processed detector data in which the processing was performed locally; or the spectrum derived from the raw detector data.

In some cases, the spectrometer may not comprise a monochromator.

In some instances, the following signal processing scheme can be used. First, an image or a series of images can be captured by the image sensor in the spectrometer mentioned above. The images can be analyzed by a local processing unit. This stage of analysis may include any or all of image averaging, compensation for aberrations of the optical unit, reduction of detector noise by use of a noise reduction algorithm, or conversion of the image into a raw spectrum. The raw spectrum is then transmitted to a remote processing unit; in some cases, the transmission can be performed using wireless communication.

The raw spectrum can be analyzed remotely. Noise reduction can be performed remotely.

In instances in which a Raman spectrum is obtained, the Raman signal can be separated from any fluorescence signal. Both Raman and fluorescence spectra can be compared to existing calibration spectra. After a calibration is performed, the spectra can be analyzed using any appropriate algorithm for spectral decomposition; non-limiting examples of such algorithms include Principal Components Analysis, Partial Least-Squares analysis, and spectral analysis using a neural network algorithm. This analysis provides the information needed to characterize the sample that was tested using the spectrometer. The results of the analysis are then presented to the user.

Figure 2:
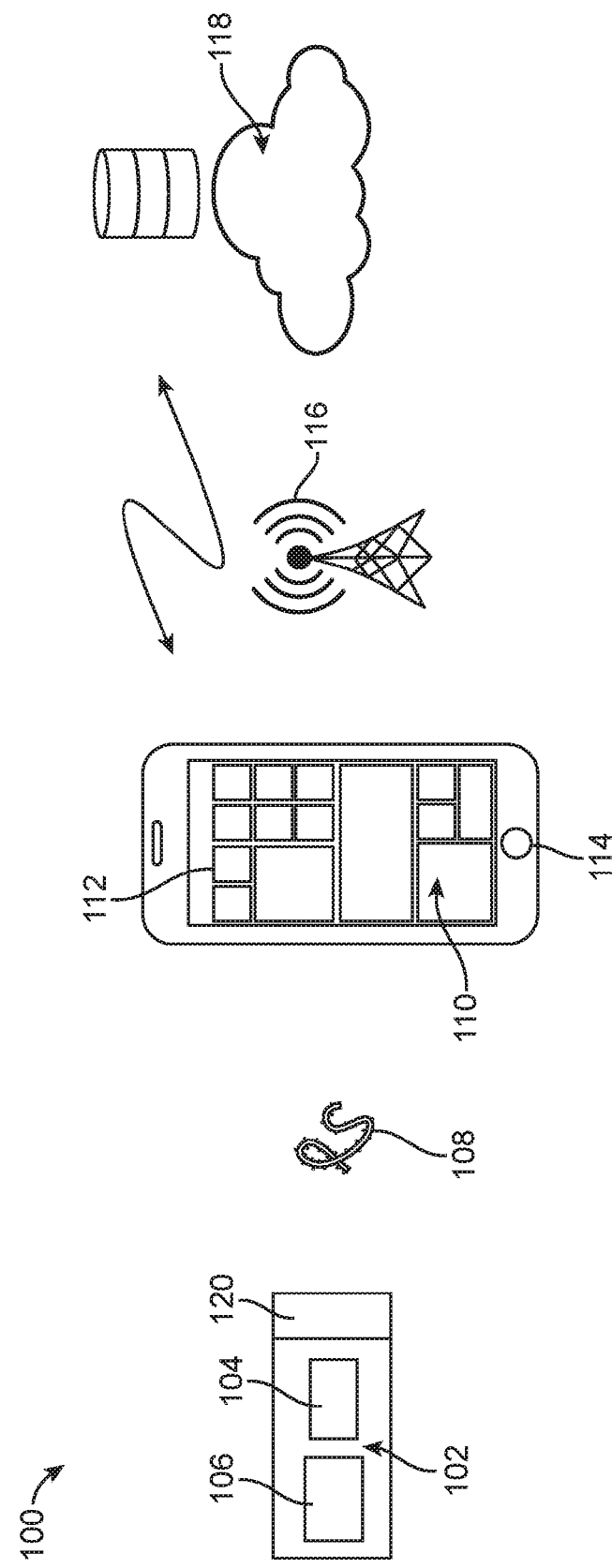
FIG. 2 shows a schematic diagram of a spectrometer system.

FIG. 2 shows a schematic diagram of a spectrometer system according to configurations. In many cases, the spectrometer system 100 can comprise a spectrometer 102 and a consumer hand held device 110 in wireless communication 116 with a cloud based storage system 118. The spectrometer 102 can acquire the data as described herein. The hand held spectrometer 102 may comprise a processor 106 and communication circuitry 104 coupled to spectrometer head 120 having spectrometer components as described herein. The spectrometer can transmit the data to the hand-held device 110 with communication circuitry 104 with a communication link, such as a wireless serial communication link, for example Bluetooth™. The hand held device can receive the data from the spectrometer 102 and transmit the data to a back end server of the cloud based storage system 118.

The hand held device 110 may comprise one or more components of a smart phone, such as a display 112, an interface 114, a processor, a computer readable memory and communication circuitry. The device 110 may comprise a substantially stationary device when used, such as a wireless communication gateway, for example.

The processor 106 may comprise a tangible medium embodying instructions, such as a computer readable memory embodying instructions of a computer program. Alternatively or in combination the processor may comprise logic such as gate array logic in order to perform one or more logic steps.

Figure 3:
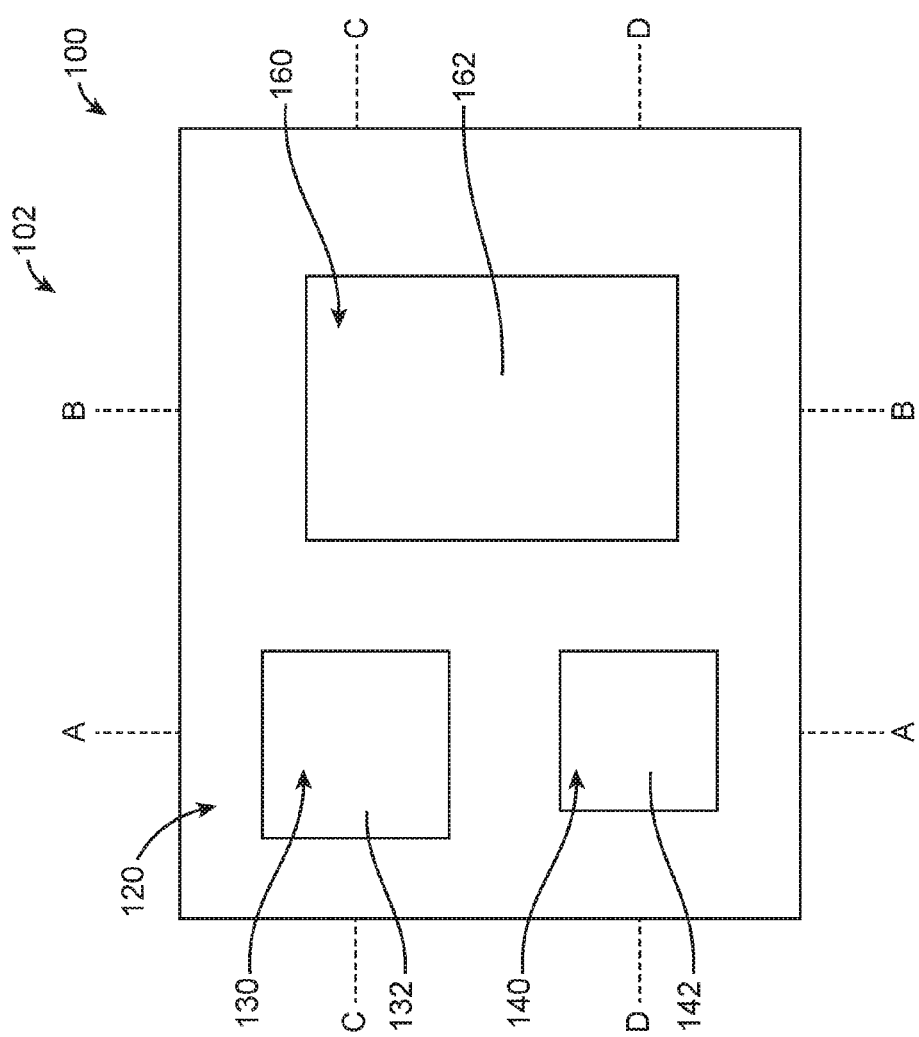
FIG. 3 shows a schematic diagram of a spectrometer head.

FIG. 3 shows a schematic diagram of spectrometer head in accordance with configurations. In many instances, the spectrometer 102 can comprise a spectrometer head 120. The spectrometer head comprises one or more of a spectrometer module 160, a temperature sensor module 130, and an illumination module 140. Each module, when present, can be covered with a module window. For example, the spectrometer module 160 can comprise a spectrometer window 162, the temperature sensor module 130 can comprise a temperature sensor window 132, and the illumination module 140 can comprise an illumination window 142.

In many instances, the illumination module and the spectrometer module are configured to have overlapping fields of view at the sample. The overlapping fields of view can be provided in one or more of many ways. For example, the optical axes of the illumination source, the temperature sensor and the matrix array can extend in a substantially parallel configuration. Alternatively, one or more of the optical axes can be oriented toward another optical axis of another module.

Figure 4:
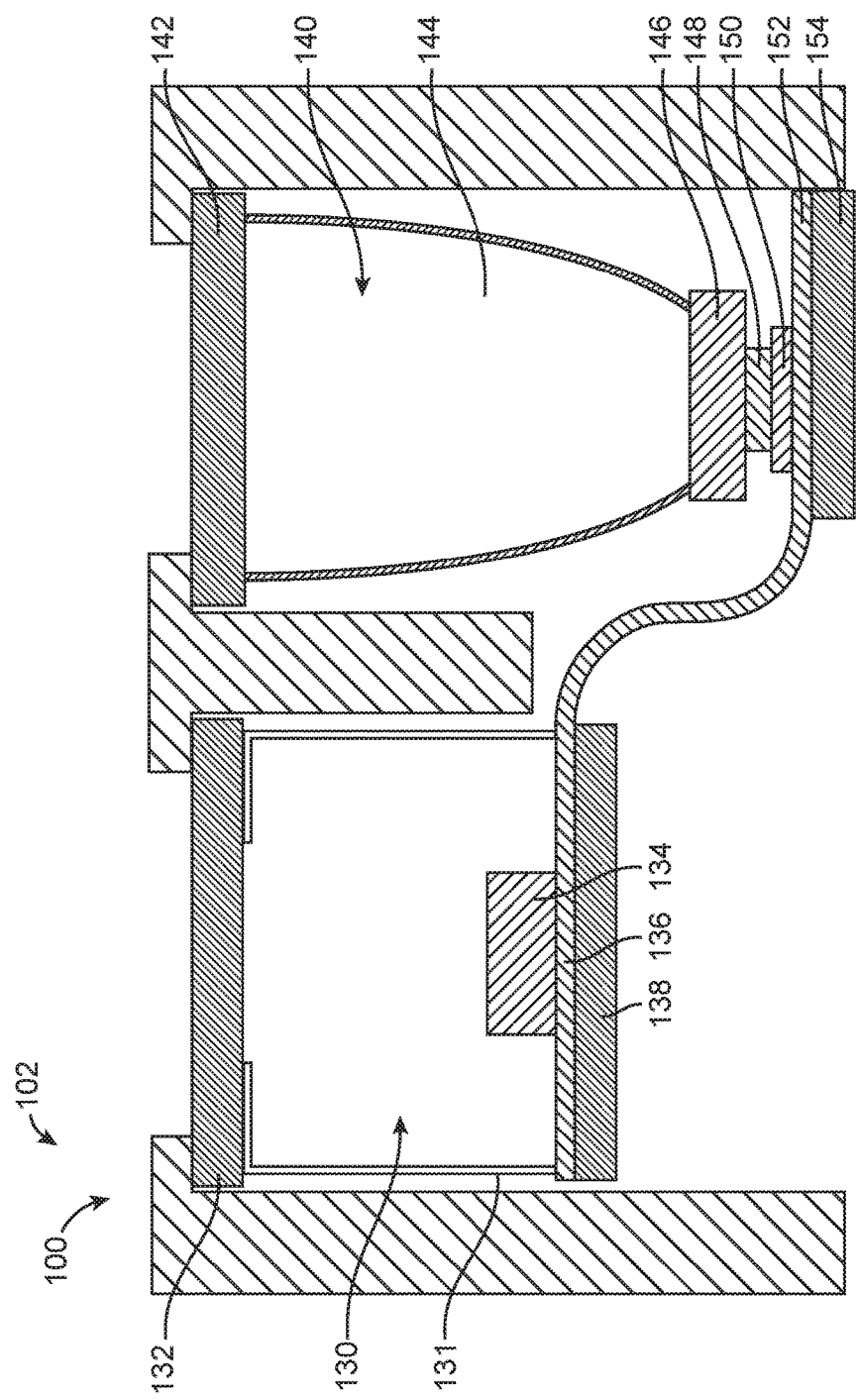
FIG. 4 shows a schematic diagram of cross-section A of the spectrometer head of FIG. 3.

FIG. 4 shows a schematic drawing of cross-section A of the spectrometer head of FIG. 3, in accordance with configurations. In order to lessen the noise and/or spectral shift produced from fluctuations in temperature, a spectrometer head 102 comprising temperature sensor module 130 can be used to measure and record the temperature during the measurement. In some instances, the temperature sensor element can measure the temperature of the sample in response to infrared radiation emitted from the sample, and transmit the temperature measurement to a processor. Accurate and/or precise temperature measurement can be used to standardize or modify the spectrum produced. For example, different spectra of a given sample can be measured based on the temperature at which the spectrum was taken. In some cases, a spectrum can be stored with metadata relating to the temperature at which the spectrum was measure. In many instances, the temperature sensor module 130 comprises a temperature sensor window 132. The temperature sensor window can seal the sensor module. The temperature sensor window 132 can be made of material that is substantially non-transmissive to visible light and transmits light in the infrared spectrum. In some cases the temperature sensor window 132 comprises germanium, for example. In some cases, the temperature sensor window is about 0.2, 0.3, 0.4, 0.5, 0.6, 0.7, 0.8, 0.9 or 1.0 mm thick.

The temperature sensor can comprise a field of view (herein after "FoV") limiter. In many instances, the temperature sensor has a field of view oriented to overlap with a field of view of the detector and a field of view of an illuminator. For example, the field of view can be limited by an aperture formed in a material supporting the window 132 of temperature sensor module and the dimensions of the temperature sensor 134. In some cases, the temperature sensor module can have a limited field of view and comprise a heat conductive metal cage disposed on a flex printed circuit board (PCB) 136. The PCB 136 can be mounted on a stiffener 138 in order to inhibit movement relative to the other modules on the sensor head. In some cases, the flexible circuit board can be backed by stiffener 138 comprising a metal. The temperature sensor 134 can be a remote temperature sensor. In some cases, the temperature sensor can give a temperature that is accurate to within about 5, 4, 3, 2, 1, 0.7, 0.4, 0.3, 0.2 or 0.1 degree Celsius of the ambient temperature of the sample. In some instances, the temperature sensor can measure the ambient temperature with precision to 3, 2, 1, 0.5, or 0.1 degree Celsius.

In many instances, the spectrometer head can comprise illumination module 140. The illumination module can illuminate a sample with light. In some cases, the illumination module can comprise an illumination window 142. The illumination window can seal the illumination module. The illumination window can be substantially transmissive to the light produced in the illumination module. For example, the illumination window can comprise glass. The illumination module can comprise a light source 148. In some cases, the light source can comprise one or more light emitting diodes (LED). In some cases, the light source can comprise a blue LED. In some instances, the light source comprises a red or green LED or an infrared LED.

The light source 148 can be mounted on a mounting fixture 150. In some cases, the mounting fixture comprises a ceramic package. For example, the light fixture can be a flip-chip LED die mounted on a ceramic package. The mounting fixture 150 can be attached to a flexible printed circuit board (PCB) 152 which can optionally be mounted on a stiffener 154 to reduce movement of the illumination module. The flex PCB of the illumination module and the PCT of temperature sensor modules may comprise different portions of the same flex PCB, which may also comprise portions of spectrometer PCB.

The wavelength of the light produced by the light source 148 can be shifted by a plate 146. Plate 146 can be a wavelength shifting plate. In some cases, plate 146 comprises phosphor embedded in glass. Alternatively or in combination, plate 146 can comprise a nano-crystal, a quantum dot, or combinations thereof. The plate can absorb light from the light source and release light having a frequency lower than the frequency of the absorbed light. In some instances, a light source can produce visible light, and plate 146 absorbs the light and emits near infrared light. In some cases, the light source can be in close proximity to or directly touches the plate 146. In some cases, the light source and associated packaging can be separated from the plate by a gap to limit heat transfer. For example the gap between the light source and the plate can be at least 0.1, 0.2, 0.3, 0.4, 0.5, 0.6, 0.7, 0.8, 0.9, 1.0, 1.5, 2.0, 2.5, 3.0, 3.5, 4.0, 5.0, 6.0, 7.0, 8.0, 9.0, or 10.0 mm. In some cases, the light source packaging touches the plate 146 in order to conduct heat from the plate such that the light source packaging comprises a heat sink.

The illumination module can further comprise a light concentrator such as a parabolic concentrator 144 or a condenser lens in order to concentrate the light. In some instances, the parabolic concentrator 144 is a reflector. In some instances, the parabolic concentrator 144 comprises stainless steel. In some cases, the parabolic concentrator 144 comprises gold-plated stainless steel. In some cases, the concentrator can concentrate light to a cone. For example, the light can be concentrated to a cone with a field of view of about 30-45, 25-50, or 20-55 degrees.

In some cases, the illumination module can be configured to transmit light and the spectrometer module can be configured to receive light along optical paths extending substantially perpendicular to an entrance face of the spectrometer head. In some instances, the modules can be configured to such that light can be transmitted from one module to an object (such as a sample 108) and reflected or scattered to another module which receives the light.

In some instances, the optical axes of the illumination module and the spectrometer module can be configured to be non-parallel such that the optical axis representing the spectrometer module is at an offset angle to the optical axis of the illumination module. This non-parallel configuration can be provided in one or more of many ways. For example, one or more components can be supported on a common support and offset in relation to an optic such as a lens in order to orient one or more optical axes toward each other. Alternatively or in combination, a module can be angularly inclined with respect to another module. In some cases, the optical axis of each module is aligned at an offset angle of greater than 1, 2, 3, 4, 5, 6, 7, 8, 9, 10, 12, 14, 16, 18, 20, 25, 30, 35, 40, 45, or 50 degrees. In some cases, the illumination module and the spectrometer module are configured to be aligned at an offset angle of less than 1, 2, 3, 4, 5, 6, 7, 8, 9, 10, 12, 14, 16, 18, 20, 25, 30, 35, 40, 45, or 50 degrees. In some instances, the illumination module and the spectrometer module are configured to be aligned at an offset angle between about 1-10, 11-20, 21-30, 31-40 or 41-50 degrees. In some cases, the offset angle of the modules can be set firmly and is not adjustable. In some instances, the offset angle of the modules can be adjustable. In some cases, the offset angle of the modules can be automatically selected based on the distance of the spectrometer head from the sample. In some cases, two modules can have parallel optical axes. In some cases, two or more modules can have offset optical axes. In some instances, the modules can have optical axes offset such that they converge on a sample. The modules can have optical axes offset such that they converge at a set distance. For example, the modules can have optical axes offset such that they converge at a distance of about 10, 20, 30, 40, 50, 60, 70, 80, 90, 100, 150, 200, 250, 300, 350, 400, or 500 mm away.

Figure 5:
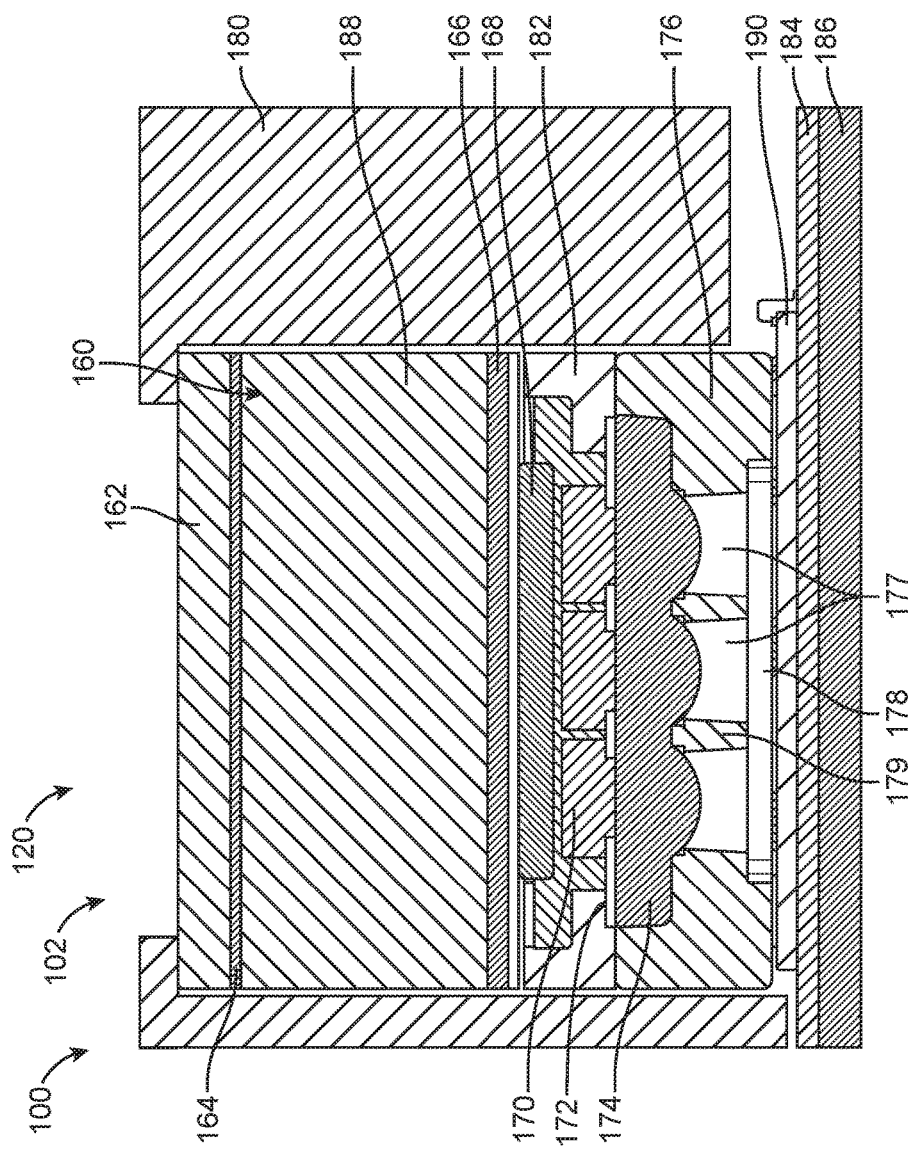
FIG. 5 shows a schematic diagram of cross-section B of the spectrometer head of FIG. 3.

FIG. 5 shows a schematic drawing of cross-section B of the spectrometer head of FIGS. 3 and 4, in accordance with configurations. In many instances, the spectrometer head 102 can comprise a spectrometer module 160. The spectrometer module can be sealed by a spectrometer window 162. In some cases, the spectrometer window 162 can be selectively transmissive to light with respect to the wavelength in order to analyze the spectral sample. For example, spectrometer window 162 can be an IR-pass filter. In some cases, the window 162 can be glass. The spectrometer module can comprise one or more diffusers. For example, the spectrometer module can comprise a first diffuser 164 disposed below the spectrometer window 162. The first diffuser 164 can distribute the incoming light. For example, the first diffuser can be a cosine diffuser. Optionally, the spectrometer module comprises a light filter 188. Light filter 188 can be a thick IR-pass filter. For example, filter 188 can absorb light below a threshold wavelength. In some cases, filter 188 absorbs light with a wavelength below about 1000, 950, 900, 850, 800, 750, 700, 650, or 600 nm. In some instances, the spectrometer module can comprise a second diffuser 166. The second diffuser can generate Lambertian light distribution at the input of the filter matrix 170. The filter assembly can be sealed by a glass plate 168. Alternatively or in combination, the filter assembly can be further supported a filter frame 182, which can attach the filter assembly to the spectrometer housing 180. The spectrometer housing 180 can hold the spectrometer window 162 in place and further provide mechanical stability to the module.

The first filter and the second filter can be arranged in one or more of many ways to provide a substantially uniform light distribution to the filters. The substantially uniform light distribution can be uniform with respect to an average energy to within about 25%, for example to within about 10%, for example. In some cases, the first diffuser can distribute the incident light energy spatially on the second diffuser with a substantially uniform energy distribution profile. In some instances, the first diffuser can make the light substantially homogenous with respect to angular distribution. The second diffuser further diffuses the light energy of the substantially uniform energy distribution profile to a substantially uniform angular distribution profile, such that the light transmitted to each filter can be substantially homogenous both with respect to the spatial distribution profile and the angular distribution profile of the light energy incident on each filter. For example, the angular distribution profile of light energy onto each filter can be uniform to within about +/−25%, for example substantially uniform to within about +/−10%.

In many instances, the spectrometer module can comprise a filter matrix 170. The filter matrix can comprise one or more filters. In many instances, the filter matrix can comprise a plurality of filters. For example, the filter matrix can comprise filters arranged in a square, rectangle, circle, oval, or disordered arrangement of filters. The filter array can comprise at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 200 or more filters. In some cases, the filter matrix can comprise between 1 and 36 inclusive filters arranged in a square or rectangular arrangement selected from the group consisting of 1×1, 1×2, 2×2, 3×1, 2×3, 3×3, 4×1, 4×2, 4×3, 4×4, 5×1, 5×2, 5×3, 5×4, 5×5, 6×1, 6×2, 6×3, 6×4, 6×5 or 6×6. In some cases, the filter array can comprise between about 10 and about 100 filters. In some cases, the filter array comprises between about 10 and about 30 filters. In some cases, the filter array comprises 4 rows filters wherein each row comprises 3 filters.

In some instances, each filter of the filter matrix 170 can be configured to transmit a range of wavelengths distributed about a central wavelength. The range of wavelengths can be defined as a full width half maximum (hereinafter "FWHM") of the distribution of transmitted wavelengths for a light beam transmitted substantially normal to the surface of the filter as will be understood by a person of ordinary skill in the art. A wavelength range can be defined by a central wavelength and by a spectral width. The central wavelength can be the mean wavelength of light transmitted through the filter, and the band spectral width of a filter can be the difference between the maximum and the minimum wavelength of light transmitted through the filter. For example, a filter can have a central wavelength of 300 nm and a wavelength range of 20 nm which would transmit light having a wavelength from 290 to 310 nm, and the filter would substantially not transmit light below 290 nm or above 310 nm. In some cases, each filter of the plurality of filters is configured to transmit a range of wavelengths different from other filters of the plurality. In some cases, the range of wavelengths can overlap with ranges of said other filters of the plurality and wherein said each filter comprises a central wavelength different from said other filters of the plurality. In some instances, the spectral width of each filter can be less than 200, 190, 180, 170, 160, 150, 140, 130, 120, 110, 100, 90, 80, 70, 60, 50, 40, 30, 20, 18, 16, 14, 12, 10, 8, 6, 4, 3, 2, or 1 nm. In some instances, the spectral width of each filter is at least 1, 2, 4, 6, 8, 10, 12, 14, 16, 18, 20, 30, 40, 50, 60, 70, 80, 90, or 100 nm. In some cases, the spectral width of each filter can be between about 1 to about 60 nm, about 2 to about 50 nm, from about 4 to about 40 nm, or from about 8 to about 30 nm. In some cases, the central wavelengths of each filter at least 1, 2, 3, 4, 5, 6, 7, 8, 9, 10, 11, 12, 14, 16, 18, 20, 25, 30, 35, 40, 50, 60, 70, 80, 90, 100, or 200 nm from the central wavelength of each other filter.

In many instances, the filter array can comprise a substrate having a thickness and a first side and a second side, the first side can be oriented toward the diffuser, the second side can be oriented toward the lens array. In some cases, each filter of the filter array can comprise a substrate having a thickness and a first side and a second side, the first side oriented toward the diffuser, the second side oriented toward the lens array. The filter array can comprise one or more coatings on the first side, on the second side, or a combination thereof. Each filter of the filter array can comprise one or more coatings on the first side, on the second side, or a combination thereof. In some cases, each filter of the filter array can comprise one or more coatings on the second side, oriented toward the lens array. In some instances, each filter of the filter array can comprise one or more coatings on the second side, oriented toward the lens array and on the first side, oriented toward the diffuser. The one or more coatings on the second side can be an optical filter. For example, the one or more coatings can permit a wavelength range to selectively pass through the filter. Alternatively or in combination, the one or more coatings can be used to inhibit cross-talk among lenses of the array. In some instances, the plurality of coatings on the second side can comprise a plurality of interference filters, said each of the plurality of interference filters on the second side configured to transmit a central wavelength of light to one lens of the plurality of lenses. In some cases, the filter array can comprise one or more coatings on the first side of the filter array. The one or more coatings on the first side of the array can comprise a coating to balance mechanical stress. In some instances, the one or more coatings on the first side of the filter array can comprise an optical filter. For example, the optical filter on the first side of the filter array can comprise an IR pass filter to selectively pass infrared light. In many cases, the first side may not comprise a bandpass interference filter coating. In some cases, the first side may not comprise a coating.

In many instances, the array of filters may comprise a plurality of bandpass interference filters on the second side of the array. The placement of the fine frequency resolving filters on the second side oriented toward the lens array and apertures can inhibit cross-talk among the filters and related noise among the filters. In many cases, the array of filters can comprise a plurality of bandpass interference filters on the second side of the array, and may not comprise a bandpass interference filter on the first side of the array.

In many instances, each filter can defines an optical channel of the spectrometer. The optical channel can extend from the filer through an aperture and a lens of the array to a region of the sensor array. The plurality of parallel optical channels can provide increased resolution with decreased optical path length.

The spectrometer module can comprise an aperture array 172. The aperture array can prevent cross talk between the filters. The aperture array comprises a plurality of apertures formed in a non-optically transmissive material. In some cases, the plurality of apertures can be dimensioned to define a clear lens aperture of each lens of the array, wherein the clear lens aperture of each lens is limited to one filter of the array. In some cases, the clear lens aperture of each lens can be limited to one filter of the array.

In many instances the spectrometer module comprises a lens array 174. The lens array can comprise a plurality of lenses. The number of lenses can be determined such that each filter of the filter array corresponds to a lens of the lens array. Alternatively or in combination, the number of lenses can be determined such that each channel through the support array corresponds to a lens of the lens array. Alternatively or in combination, the number of lenses can be selected such that each region of the plurality of regions of the image sensor corresponds to an optical channel and corresponding lens of the lens array and filter of the filter array.

In many instances, each lens of the lens array comprises one or more aspheric surfaces, such that each lens of the lens array comprises an aspherical lens. In many cases, each lens of the lens array can comprise two aspheric surfaces. Alternatively or in combination, one or more individual lens of the lens array can have two curved optical surfaces wherein both optical surfaces are substantially convex. Alternatively or in combination, the lenses of the lens array may comprise one or more diffractive optical surfaces.

In many instances, the spectrometer module can comprise a support array 176. The support array 176 can comprise a plurality of channels 177 defined with a plurality of support structures 179 such as interconnecting annuli. The plurality of channels 177 may define optical channels of the spectrometer. The support structures 179 can comprises stiffness to add rigidity to the support array 176. The support array may comprise a stopper to limit movement and fix the position the lens array in relation to the sensor array. The support array 176 can be configured to support the lens array 174 and fix the distance from the lens array to the sensor array in order to fix the distance between the lens array and the sensor array at the focal length of the lenses of the lens array. In many cases, the lenses of the array can comprise substantially the same focal length such that the lens array and the sensor array are arranged in a substantially parallel configuration.

The support array 176 can extend between the lens array 174 and the stopper mounting 178. The support array 176 can serve one or more purposes, such as 1) providing the correct separation distance between each lens of lens array 170 and each region of the plurality of regions of the image sensor 190, and/or 2) preventing stray light from entering or exiting each channel, for example. In some cases, the height of each support in support array 176 can be calibrated to the focal length of the lens within lens array 174 that it supports. In some cases, the support array 176 can be constructed from a material that does not permit light to pass such as substantially opaque plastic. In some cases, support array 176 can be black, or comprises a black coating to further reduce cross talk between channels. The spectrometer module can further comprise a stopper mounting 178 to support the support array. In many instances, the support array can comprise an absorbing and/or diffusive material to reduce stray light, for example.

In many instances, the support array 176 can comprise a plurality of channels having the optical channels of the filters and lenses extending therethrough. In some cases, the support array comprises a single piece of material extending from the lens array to the detector (i.e. CCD or CMOS array).

The lens array can be directly attached to the aperture array 172, or can be separated by an air gap of at least 1, 2, 3, 4, 5, 6, 7, 8, 9, 10, 12, 14, 16, 18, 20, 30, 40, or 50 micrometers. The lens array can be directly on top of the support array 178. Alternatively or in combination, the lens array can be positioned such that each lens is substantially aligned with a single support stopper or a single optical isolator in order to isolate the optical channels and inhibit cross-talk. In some cases, the lens array is positioned to be at a distance approximately equal to the focal length of the lens away from the image sensor, such that light coming from each lens is substantially focused on the image sensor.

In some cases, the spectrometer module can comprise an image sensor 190. The image sensor can be a light detector. For example, the image sensor can be a CCD or 2D CMOS or other sensor, for example. The detector can comprise a plurality of regions, each region of said plurality of regions comprising multiple sensors. For example, a detector can be made up of multiple regions, wherein each region is a set of pixels of a 2D CMOS. The detector, or image sensor 190, can be positioned such that each region of the plurality of regions is directly beneath a different channel of support array 176. In many instances, an isolated light path is established from a single of filter of filter array 170 to a single aperture of aperture array 172 to a single lens of lens array 174 to a single stopper channel of support array 176 to a single region of the plurality of regions of image sensor 190. Similarly, a parallel light path can be established for each filter of the filter array 170, such that there are an equal number of parallel (non-intersecting) light paths as there are filters in filter array 170.

The image sensor 190 can be mounted on a flexible printed circuit board (PCB) 184. The PCB 184 can be attached to a stiffener 186. In some cases, the stiffener can comprise a metal stiffener to prevent motion of the spectrometer module relative to the spectrometer head 120.

Figure 6:
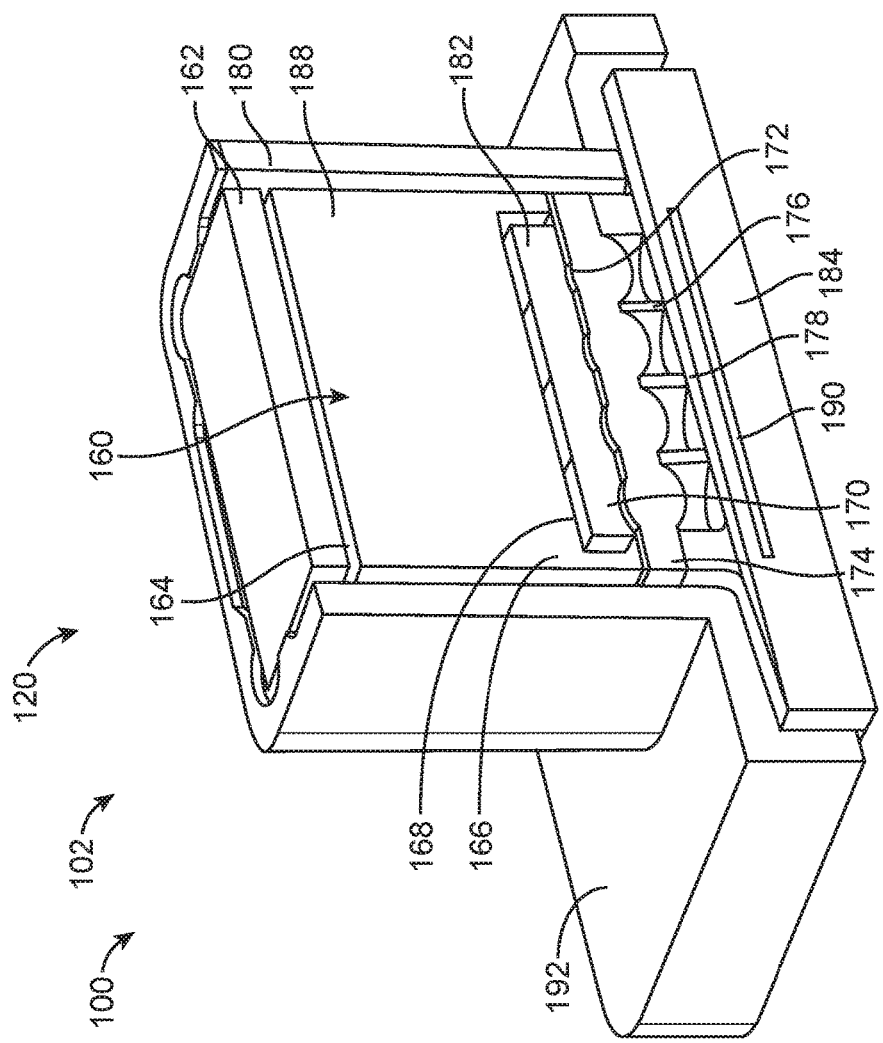
FIG. 6 shows a schematic diagram of a spectrometer module.

FIG. 6 shows an isometric view of a spectrometer module 160 in accordance with configurations. The spectrometer module 160 comprises many components as described herein. In many instances, the support array 176 can be positioned on a package on top of the sensor. In many instances, the support array can be positioned over the top of the bare die of the sensor array such that an air gap is present. The air gap can be less than 10, 9, 8, 7, 6, 5, 4, 3, 2 or 1 micrometer(s).

Figure 7:
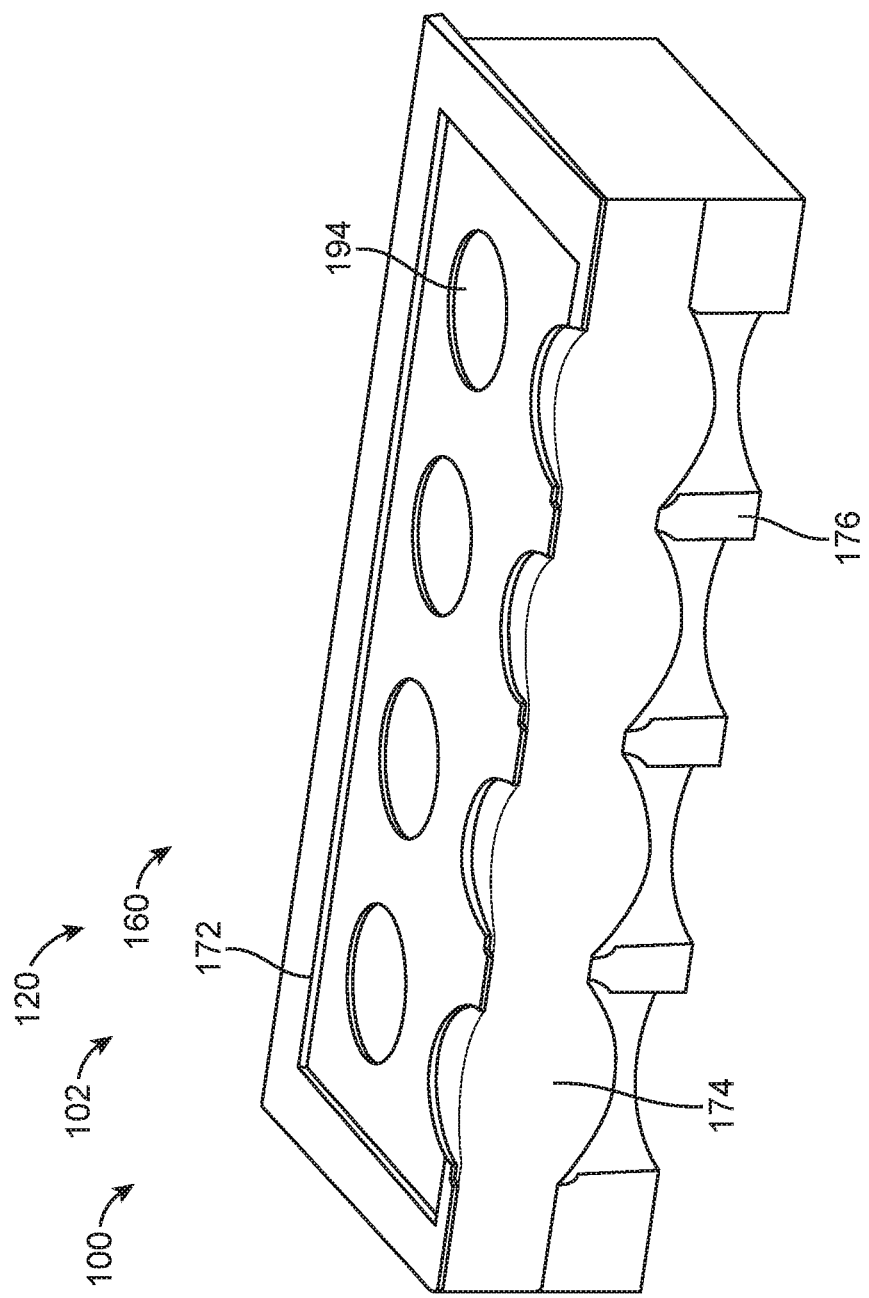
FIG. 7 shows a schematic diagram of apertures formed in a non-transmissive material and a lens array.

FIG. 7 shows the lens array 174 within the spectrometer module 160, in accordance with configurations. This isometric view shows the apertures 194 formed in a non-transmissive material of the aperture array 172 in accordance with configurations. In many cases, each channel of the support array 176 is aligned with a filter of the filter array 170, a lens of the lens array 174, and an aperture 194 of the aperture array in order to form a plurality of light paths with inhibited cross talk.

Figure 8:
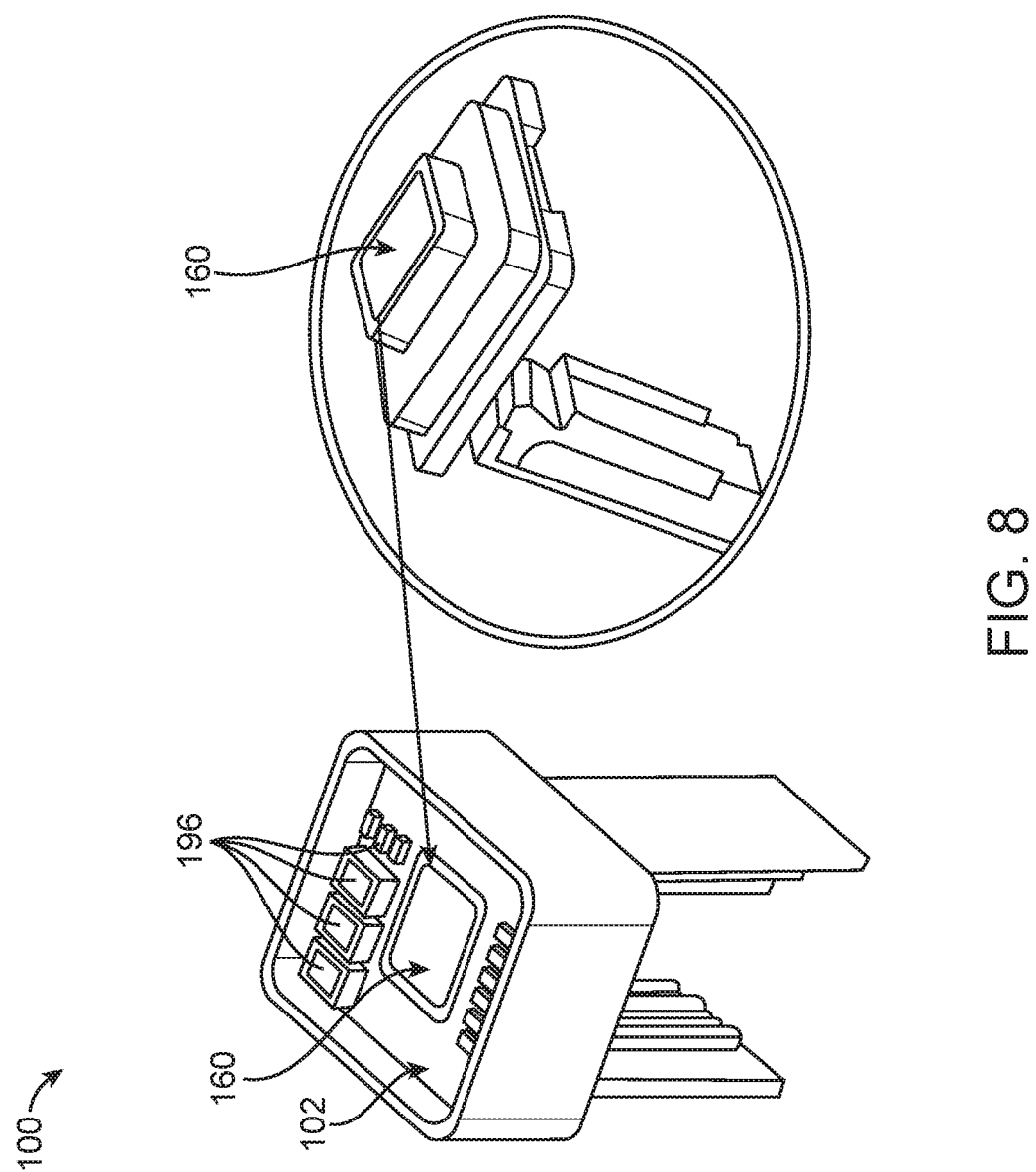
FIG. 8 shows a schematic diagram of a spectrometer.

FIG. 8 shows a spectrometer 102 in accordance with configurations. The spectrometer can comprise an optical head which can comprise a spectrometer module 160. The spectrometer can further comprise a temperature sensor module. In many cases, the spectrometer can comprise an illumination module. In many cases, the spectrometer can comprise light emitting diodes 196 distinct from an illumination module. The spectrometer can also comprise further components such as a Bluetooth™ module to communicate data to another device, a spectrometer processor 106, a power supply, or combinations thereof.

The spectrometer as described herein can be combined with a protective cover comprising a sheath. The protective cover may comprise an internal calibration material that allows the spectrometer to be calibrated when placed in the sheath. The spectrometer can also be provided with an accessory container that couples to one end of the sheath when the spectrometer has been placed therein. In some cases the accessory can couple to an end of the spectrometer when the spectrometer is not placed in the sheath.

Figure 9A:
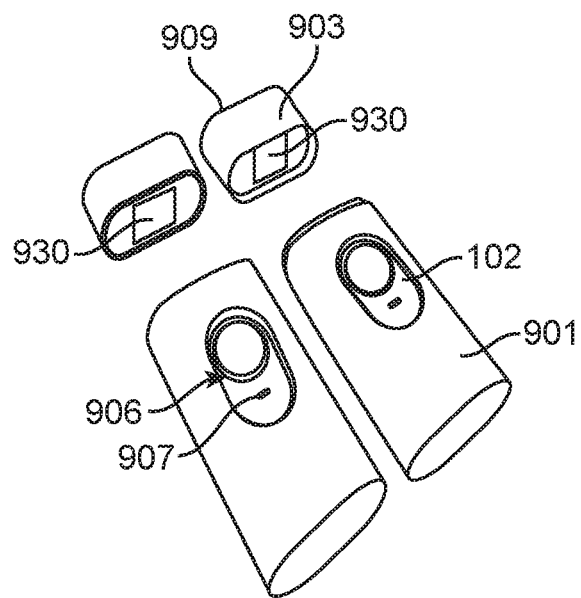
FIGS. 9A and 9B show perspective views of a spectrometer in a cover and a removable accessory container.
Figure 9B:
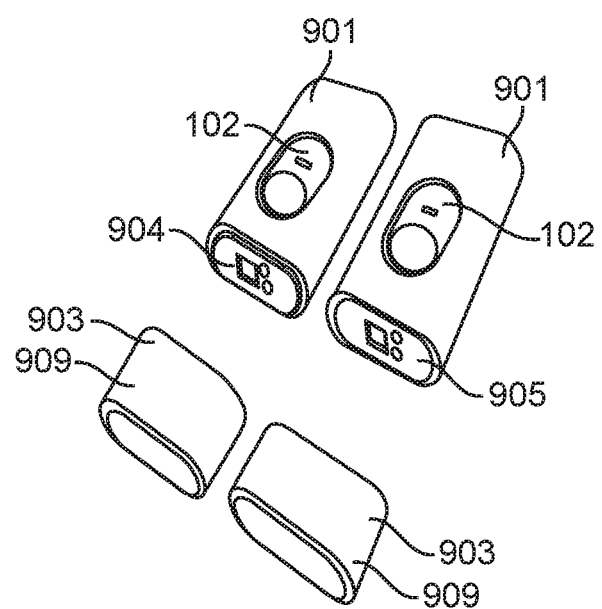

FIGS. 9A and 9B show perspective views of a spectrometer 102 as described herein placed in a protective sheath or cover 901 and coupled to a removable accessory 909 such as container 903, in accordance with configurations. In many cases, the cover 901 can comprise a protective sheath sized to receive the spectrometer. The cover can comprise a cover configured to fit over an end of the spectrometer or a cover configured to fit over more than an end of the spectrometer. The spectrometer can be removed from the sheath cover and placed in the sheath cover with an appropriate orientation to measure samples or calibrate the spectrometer. In many cases, the cover can have an open end and a closed end. In many instances, the spectrometer can comprise a protective housing sized to fit within the protective sheath. The spectrometer comprising the housing can be placed in the cover sheath with the optics of the spectrometer head directed toward the closed end of the cover sheath in order to calibrate the spectrometer. The cover may comprise a reflective calibration material to couple to the light source and the sensor array of the spectrometer, in order to reflect light from a calibration material to the sensor array in a repeatable manner. The reflective material may be a diffusive reflective material. The cover can be removable from the spectrometer. To measure a sample, the spectrometer can be placed in the cover 901 such that the spectrometer head faces the open end of the cover. In some cases, the cover can be configured to be removed and/or replaced by a user. The cover can provide a protective covering for the spectrometer during storage and use. In many instances, the cover can comprise a reference material for calibration of the spectrometer. The cover can additionally couple to an accessory 909 to provide a controlled measurement environment for conducting measurements of a sample.

Figure 9C:
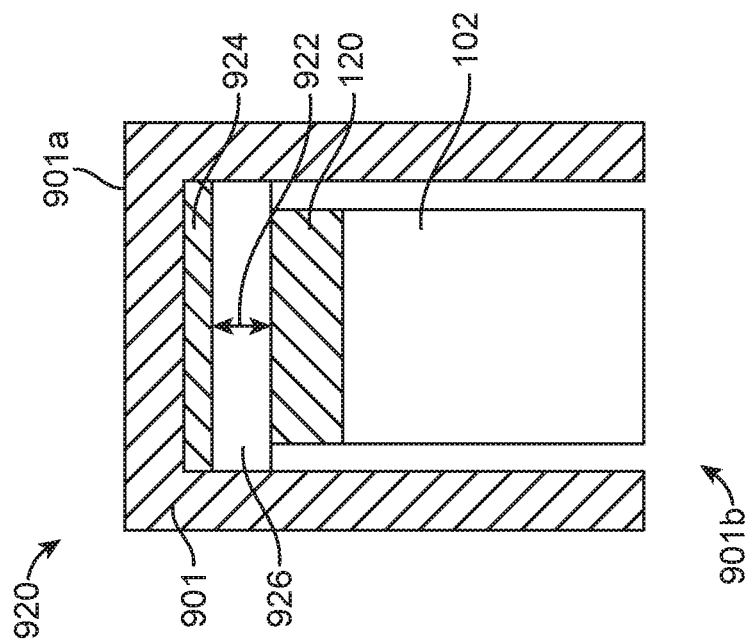
FIG. 9C shows a schematic diagram of a spectrometer placed within a cover in a measurement configuration.

FIG. 9C shows a schematic diagram of a spectrometer 102 placed within a cover 901 in a measurement configuration or orientation 910. The cover 901 may comprise a closed end 901*a* and an open end 901*b*. The spectrometer 102 may comprise a spectrometer head or optical module 120 as described herein. In the measurement configuration, the spectrometer may be placed in the cover such that the optical module is adjacent to the open end of the cover. In the measurement configuration, the spectrometer may be used to measure a sample 108 placed adjacent the optical module. The sample may be measured while the sample is placed at a measurement distance 912 between the optical head and the sample surface. In some configurations, the measurement distance 912 may be a predetermined measurement distance. For example, as described in further detail herein, the sample may be placed in a sample container configured to couple to the spectrometer and/or the cover such that the sample is placed at a predetermined measurement distance from the optical module of the spectrometer.

Figure 9D:
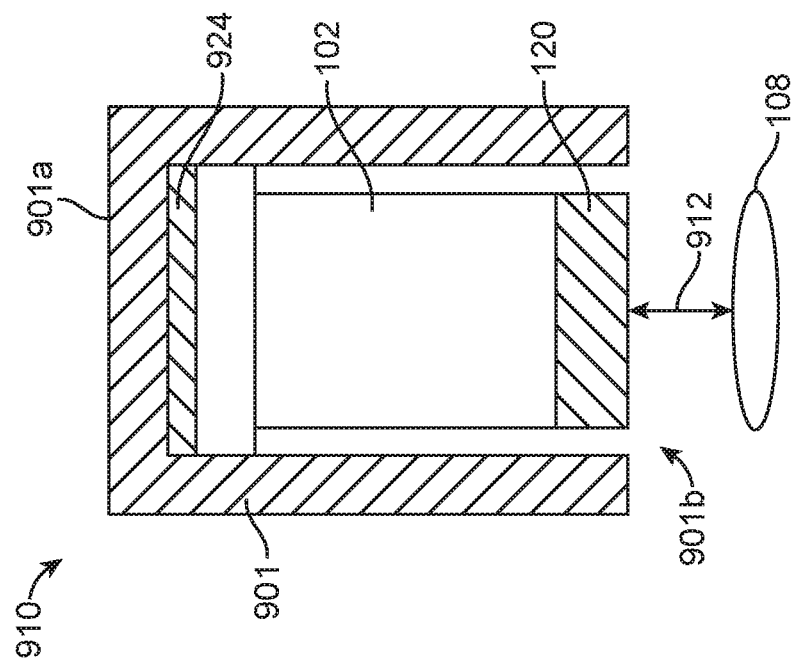
FIG. 9D shows a schematic diagram of a spectrometer placed within a cover in a calibration configuration.

FIG. 9D shows a schematic diagram of a spectrometer 102 placed within a cover 901 in a calibration configuration or orientation 920. The cover 901 may comprise a closed end 901*a* and an open end 901*b*, wherein the cover 901 may comprise a reference material or calibration material 924 disposed near the closed end, as described in further detail elsewhere herein. In the calibration configuration, the spectrometer may be placed in the cover such that the optical module 120 of the spectrometer is adjacent to the closed end 901*b* of the cover, and facing the calibration material 924. In the calibration configuration, the spectrometer may be calibrated by measuring the calibration material. The calibration material may be placed at a predetermined calibration distance 922 between the optical module and the calibration material. For example, as described in further detail herein, the cover may comprise a base 926 configured to couple to the optical module of the spectrometer and place the optical module at a fixed calibration distance 922 from the calibration material.

In some cases, the spectrometer can be placed in a cover or sheath 901. The sheath can be made from a light weight material. The sheath can be made from a polymer, metal, or composite material. The sheath can have a weight of at most about 50 g, 45 g, 40 g, 35 g, 30 g, 25 g, 20 g, 15 g, 10 g, 5 g, 4 g, 3 g, 2 g, 1 g, 0.1 g, or 0.001 g. The sheath can have a weight less than 0.001 g. The sheath can have a weight greater than 50 g. The sheath can have a weight that is between any of the two values given above. The sheath and spectrometer can have a combined weight of about 1 gram (g), 5 g, 10 g, 15 g, 20 g, 25 g, 30 g, 35 g, 40 g, 45 g, 50 g, 55 g, 60 g, 65 g, 70 g, 80 g. 85 g, 90 g, 95 g, 100 g, 110 g, 120 g, 130 g, 140 g, 150 g, 160 g, 170 g, 180 g, 190 g, or 200 g. The sheath and spectrometer can have a combined less than 1 g. The sheath and spectrometer can have a combined greater than 200 g. The sheath and spectrometer can have a combined that is between any of the two values given above.

The cover or sheath can be sized and shaped such that the sheath does not add significant bulk to the volume of the spectrometer. The spectrometer can have a snug fit when placed in the spectrometer. The spectrometer fitted in the sheath can have a total volume of at most about 100 cm$^3$, 95 cm$^3$, 90 cm$^3$, 85 cm$^3$, 80 cm$^3$, 75 cm$^3$, 70 cm$^3$, 65 cm$^3$, 60 cm$^3$, 55 cm$^3$, 50 cm$^3$, 45 cm$^3$, 40 cm$^3$, 35 cm$^3$, 30 cm$^3$, 25 cm$^3$, 20 cm$^3$, 15 cm$^3$, 10 cm$^3$, 5 cm$^3$, or 1 cm$^3$. The spectrometer fitted in the sheath can have a volume less than 1 cm$^3$. The spectrometer fitted in the sheath can have a volume greater than 100 cm$^3$. The spectrometer fitted in the sheath can have a volume that is between any of the two values given above.

The spectrometer when fitted in the cover or sheath can have a shape comprising a rectangular prism, cylinder, or other three-dimensional shape. The sheath can have a similar shape as the spectrometer. The spectrometer fitted in the sheath can have a length of at most about 500 mm, 400 mm, 300 mm, 200 mm, 250 mm, 100 mm, 95 mm, 90 mm, 85 mm, 80 mm, 75 mm, 70 mm, 65 mm, 60 mm, 55 mm, 50 mm, 45 mm, 40 mm, 35 mm, 30 mm, 25 mm, 20 mm, 15 mm, 10 mm, or 5 mm. The spectrometer fitted in the sheath can have a width of at most about 500 mm, 400 mm, 300 mm, 200 mm, 250 mm, 100 mm, 95 mm, 90 mm, 85 mm, 80 mm, 75 mm, 70 mm, 65 mm, 60 mm, 55 mm, 50 mm, 45 mm, 40 mm, 35 mm, 30 mm, 25 mm, 20 mm, 15 mm, 10 mm, or 5 mm. The spectrometer fitted in the sheath can have a length less than 5 mm. The spectrometer fitted in the sheath can have a length greater than 500 mm. The spectrometer fitted in the sheath can have a length that is between any of the two values given above. The spectrometer fitted in the sheath can have a height of at most about 500 mm, 400 mm, 300 mm, 200 mm, 250 mm, 100 mm, 95 mm, 90 mm, 85 mm, 80 mm, 75 mm, 70 mm, 65 mm, 60 mm, 55 mm, 50 mm, 45 mm, 40 mm, 35 mm, 30 mm, 25 mm, 20 mm, 15 mm, 10 mm, or 5 mm. The spectrometer fitted in the sheath can have a height less than 5 mm. The spectrometer fitted in the sheath can have a height greater than 500 mm. The spectrometer fitted in the sheath can have a height that is between any of the two values given above. In the case of a cylindrical spectrometer the spectrometer fitted in the sheath can have a radius of at most about 500 mm, 400 mm, 300 mm, 200 mm, 250 mm, 100 mm, 95 mm, 90 mm, 85 mm, 80 mm, 75 mm, 70 mm, 65 mm, 60 mm, 55 mm, 50 mm, 45 mm, 40 mm, 35 mm, 30 mm, 25 mm, 20 mm, 15 mm, 10 mm, or 5 mm. The spectrometer fitted in the sheath can have a radius less than 5 mm. The spectrometer fitted in the sheath can have a radius greater than 500 mm. The spectrometer fitted in the sheath can have a radius that is between any of the two values given above.

In many instances the accessory 909 may comprise a light source. The light source may be oriented such that a sample placed in the accessory is between the light source in the accessory and the optical head of the spectrometer. In some cases, the accessory may be configured to transmit light energy through a sample. The light energy that is transmitted through the sample may be detected by the optical head of the spectrometer. The light source in the accessory can be powered by a power source or power storage device in the accessory. In some cases, the light source in the accessory can be powered by a power source or power storage device in the spectrometer. The accessory can comprise one or more electrical contacts configured to contact one or more electrical contacts on the spectrometer. When the one or more electrical contacts on the accessory contact the one or more electrical contacts on the spectrometer, energy can be transferred from the power source or power storage device in the spectrometer to the light source in the accessory. In some instances the light source in the accessory can receive light from the light source in the spectrometer by a fiber optic transmission line. In some instances the accessory can further comprise a temperature sensor. The temperature sensor can measure temperature in the accessory and the measured temperature can be used in interpretation of spectrometer measurements of a sample placed in the accessory.

The accessory 909 can comprise a hollow region or cavity. The cavity can be a sample container 903. The sample container can be exposed to the spectrometer light source when the accessory is coupled to the spectrometer. Ambient light may not be permitted to enter the cavity when the accessory is coupled to the spectrometer. The sample container can comprise a non-optically transmissive material having a channel 930 formed therein to receive light energy from the spectrometer light source. The sample container can have walls that are coated with a material that does not reflect light energy. In some cases, the sample container can comprise at least one surface with a highly reflective coating. Alternatively or in combination, the sample container can have walls coated with a black coloring or coating. The black coloring or coating may not reflect light energy or may reflect a substantially small percentage of light energy.

At least one inner surface of the sample container 903 can be covered with or contain an optically reflective surface or entity. The optically reflective surface or entity can comprise a first reflective material having predetermined optical properties. The sample container can transmit reflected light, for example reflected light off the reflective surface or entity, or first reflective material, to the spectrometer sensor. The sample container can inhibit or prevent interference from ambient light. In many instances, ambient light can be light outside of the sample container. In some cases, the first reflective material can be a reflective material with a size and shape configured to fit within a recess formed in the sample container. The reflective material can have known optical properties. For example, an optical property that can be known for the reflective material can be reflectivity, absorptivity, and/or transmissivity. The known optical properties of the reflective material can be constant with respect to one or more environmental properties, for example, temperature, humidity, and/or pressure. The known optical properties of the reflective material can be constant with respect to the properties of light incident on the reflective material. In many instances, properties of the light incident on the reflective material can include wavelength, intensity, and/or frequency. In some cases, the sample container can comprise a second reflective material on an inner side wall of the channel to reflect light energy from the spectrometer light source toward the first reflective material, and from the first reflective material toward the spectrometer sensor array. The second reflective material can have a size and shape such that it is configured to fit along a side wall of the sample container channel. The second reflective material can have known optical properties.

The spectrometer can further comprise a support to engage the accessory 909 or the cover 901 and place the reflective material of the sample container 903 at a predetermined distance from the spectrometer light source and sensor array. The predetermined distance can be a fixed or variable distance. The accessory can comprise an engagement structure to engage the support on the spectrometer.

The support can be shaped to receive, couple to, and/or mate with the engagement structure of the accessory. The engagement structure can be removably coupled to the support. The accessory can be attached to the spectrometer when the support and engagement structure are positively mated or coupled. The engagement structure can permit placement and removal of the accessory on the spectrometer. The engagement structure can couple the accessory to the spectrometer such that ambient light cannot enter the container. In some cases, the engagement structure can comprise one or more of a protrusion, a rim, a flange, a recess, or a magnet. The support can comprise one or more of a protrusion, a rim, a flange, a recess, or a magnet configured to engage a corresponding portion of the engagement structure. In some cases, a locking mechanism can further couple the spectrometer and the cover. A user can release the locking mechanism to remove the accessory from the spectrometer. In many instances, a locking mechanism can be a pin and tumbler locking mechanism.

Additionally, an accessory 909 comprising a sample container 903 can be coupled to the spectrometer 102 as described herein. In some cases, the sample container 903 and the cover 901 can couple to the spectrometer interchangeably. Alternatively, the sample container and the cover can couple to the spectrometer simultaneously. The spectrometer 102, the cover 901, and the sample container 903 are shown in FIG. 9A and FIG. 9B. FIG. 9A shows the spectrometer 102 inside of the container of the cover 901, with a sample container 903. The sample container 903 can contain a material to be measured by the spectrometer. As shown in FIGS. 9A and 9B the spectrometer is placed in the cover with the spectrometer head facing outward. These configurations can be used to collect sample measurements. In alternate configurations, the spectrometer can be flipped such that the spectrometer head faces into the cover, wherein this configuration can be used during calibration.

In many cases, the container of the cover 901 comprises a sheath cover that can be configured to receive the spectrometer 102 contained within the housing as described herein. The cover 901 may comprise one or more openings 906 through which one or more structural features of the spectrometer can be accessed. In some cases, a protrusion 907 on the spectrometer 102 may be accessed through the one or more openings 906. The protrusion 907 can comprise a raised bump, raised line, a groove, a depression, a textured surface, a nub, and/or a raised structural feature that can be gripped by a user's hand and/or finger. A user may push the spectrometer 102 out of the container 902 by pushing and/or pulling on the protrusion 907 to apply a shear force to the spectrometer. The sheath cover may comprise an open end sized to receive the spectrometer and housing and a closed end opposite the open end. The spectrometer can be received in the sheath cover with the spectrometer optics head oriented toward the closed end, such that the spectrometer and sheath comprise a calibration configuration. Alternatively, the spectrometer can be received in the sheath cover with the spectrometer optics head oriented toward the open end, such that the spectrometer and sheath comprise a measurement configuration. The calibration material can be located closer to the closed end than the open end in order to calibrate the spectrometer.

The sheath or cover may comprise a structure having an open end, a closed end, and an interior sized to receive the spectrometer, and one or more engagement structures to receive the spectrometer in a first orientation with spectrometer optics oriented toward the closed end and a second orientation with the spectrometer optics oriented toward the open end.

The sample container 903 (e.g. accessory 909) can provide a controlled environment for measurement of a sample material by the spectrometer. The sample container can be removably attached to the spectrometer. In many cases, a user can measure properties of a sample material by placing the material in the sample container, attaching the sample container to the spectrometer and using the spectrometer to measure the material in the sample container. The sample container can place the material at a known distance from the spectrometer light source. When attached to the spectrometer, the sample container can inhibit noise signals from ambient light sources. Ambient light sources can be any light sources that do not originate from the light source of the spectrometer.

In many instances, the calibration material can be spaced apart from the optics head with a calibration distance in the calibration orientation and wherein the sample container is sized and shaped to place the sample spaced apart from the optics head with a measurement distance in the measurement orientation similar to the calibration distance to within about 100%.

In many cases, the sample container and the spectrometer can comprise mating or coupling attachment structural features. The sample container can be mounted on the optical head side of the spectrometer. In many cases, the coupling attachment structural features can be complementary structural features on the sample container and the spectrometer. The complimentary structural features can comprise one or more of a protrusion, a rim, a flange, a recess, or a magnet configured to couple the sample container to the spectrometer. FIG. 9B shows a sample container 903 configured to fit over a stepped protrusion 904 on a spectrometer 102. Alternatively, FIG. 9B also shows a sample container 903 configured to couple to a flush surface 905 of the spectrometer 102.

The sample container and/or the cover can comprise asymmetric mating structural features such that the sample container can connect to the spectrometer only in a preferred orientation. In many instances, asymmetric mating structural features can be grooves, channels, pins, or other shape factors provided on either or both of the container and/or cover and the spectrometer. The asymmetric mating structural features can prevent the sample container from connecting to the spectrometer in at least one orientation. The asymmetric structural features can force the sample container to be mounted on the spectrometer such that a sample in the sample container is in a known location relative to the spectrometer. The known location can be a known location relative to the light source in the spectrometer. In some instances, the known location relative to the light source in the spectrometer is a horizontal or vertical distance. In some cases, the known location relative to the light source in the spectrometer is an angular orientation in relation to the light source and the sensor array.

Figure 10:
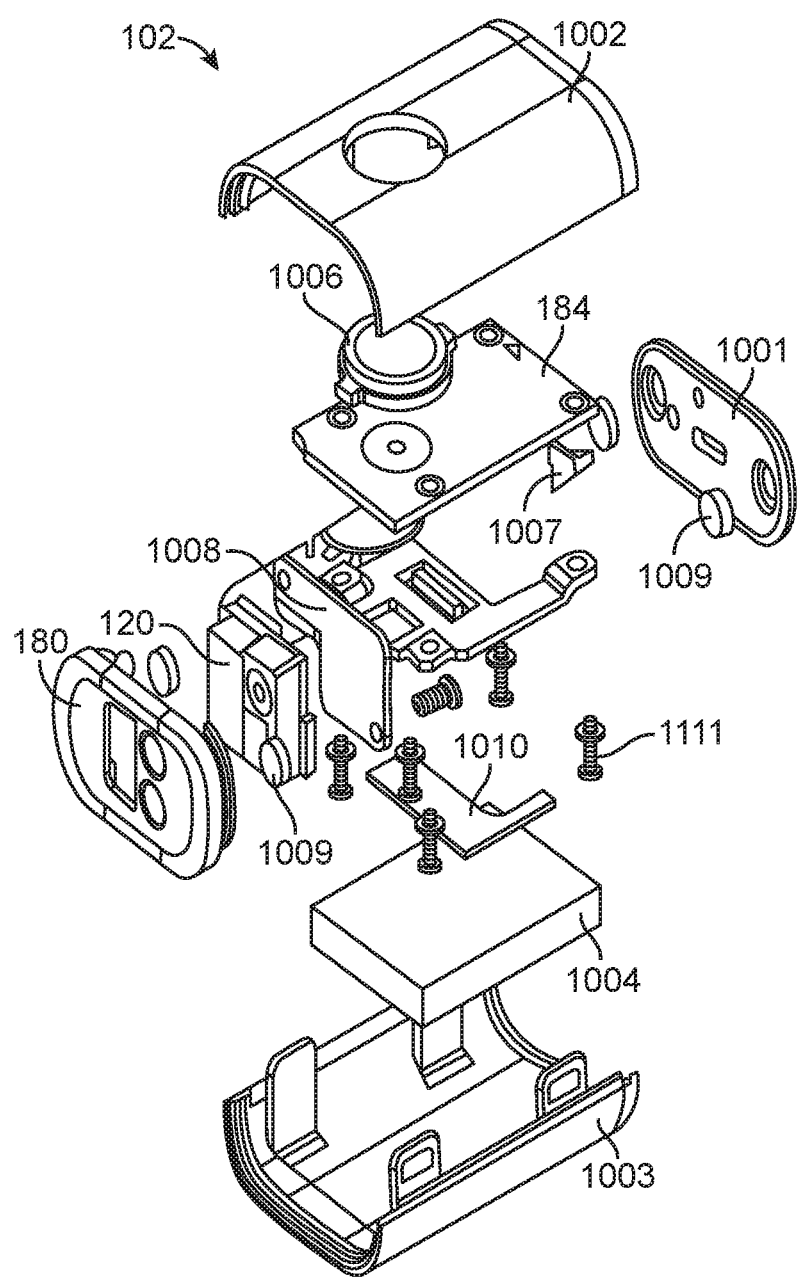
FIG. 10 shows an exploded assembly diagram of a spectrometer.

FIG. 10 shows and exploded view of the spectrometer 102. The spectrometer shown in FIG. 10 can be placed in the cover as described herein. The spectrometer can be enclosed by a set of housing pieces. The housing pieces can be connected by one or more screws or fasteners 1111. The housing pieces can include a head housing 180, a tail housing 1001, a top housing 1002, and a bottom housing 1003. The housing pieces can be removably connected. In some cases, the housing pieces can snap or slide open or apart to open and provide access to an interior region enclosed by the housing pieces. In some instances the housing pieces can be opened to provide access to a battery 1004. The battery can be a rechargeable or replaceable battery. In the case of a rechargeable battery, the battery can be removed from the housing for recharging or the spectrometer can comprise charging contact to charge the battery while the battery is in the device. The charging contact can provide an electrical connection between the battery and an exterior surface of the housing. The battery 1004 can be a power source for the spectrometer components, for example, the battery can power the light source can one or more processors on-board the spectrometer configured to perform measurements. The battery can be fixed in the housing by an adhesive, for example battery tape 1010. An operating button 1006 can allow a user to control battery power to one or more components in the spectrometer. In some cases, a user can power a spectrometer on and off by manipulating the operating button. An operating button can be a compressible button, switch, or touchscreen (e.g. capacitive screen). In many instances, a user can push the operating button 1006 to complete an electrical circuit such that the circuit is closed when a user pushes the button and the battery 1004 provides power to one or more components in the spectrometer. The user can push the button 1006 again to open the circuit and prevent the battery 1004 from providing power to one or more components in the spectrometer. In some cases, the operating button 1006 can be pressed in a predetermined sequence to program one or more features of the spectrometer. The button 1006 can be accessible through an opening on one or more of the housing pieces, for example, the button 1006 can be accessible through the top housing 1002. The battery 1004 can be connected to a battery indicator 1007. The battery indicator 1007 can be configured to sense the voltage of the battery 1004. The battery indicator can communicate the health (e.g. remaining charge) of the battery to a user. In many instances, the battery indicator 1007 can be an LED. The battery indicator can be visible by extruding through a housing piece or through a window on a housing piece. In many instances, the battery indicator can be visible through the tail housing 1001. In some cases the battery indicator can be an LED that is red and/or flashing when the battery has a low charge.

The battery 1004 can provide power to the spectrometer head 120 which can also be referred to as the optical module. The optical module 120 can be in communication with a PCB 184. The optical module 120 can be connected to a heat sink 1008. The heat sink 1008 can be a thermally conductive material configured to remove heat from either or both of the optical module 120 and the PCB 184. In some cases, the heat sink 1008 can comprise heating fins. The optical module can be covered by the head housing 180. The head housing can comprise one or more windows such that optical components of the optical module can be exposed to the exterior of the housing.

The spectrometer can comprise a measurement portion and a handle portion to direct the measurement portion toward a sample. The handle portion can be sized and configured for handling by a user with one hand. The spectrometer can comprise the support configured to couple to the engagement structure on the cover. The measurement portion can comprise the support. The handle portion can comprise a support sized and shaped to receive the cover. The cover can be coupled to either or both of the measurement portion or the handle portion. The support can comprise a housing to enclose the light source and the sensor array. The spectrometer can have a window to receive light from a sample. The support and the cover can be configured to place a reflective material at a predetermined distance from the window with a gap extending between the reflective material and the window.

The head and tail housing can comprise one or more magnets 1009. The magnets can be exposed to the outer surface of the housing or the magnets can be imbedded in the housing such that they are not exposed on the outer surface. The magnets can be configured to mate with, attract, or couple to magnets or magnetic materials provided on the cover and/or the sample container. The magnets can be the support on the spectrometer configured to couple to the engagement structure on the cover. The engagement structure can comprise a cover magnetic material configured to couple to the support magnetic material. In some cases, the engagement structure and the support can comprise corresponding asymmetric engagement structures to position the cover at a predetermined position and angular orientation with respect to the light source and the sensor array. In many cases, the polarity of the magnets can be an asymmetric engagements structure when the polarity is chosen such that some orientations of the cover and spectrometer are permitted while other configurations are prevented.

Figure 11:
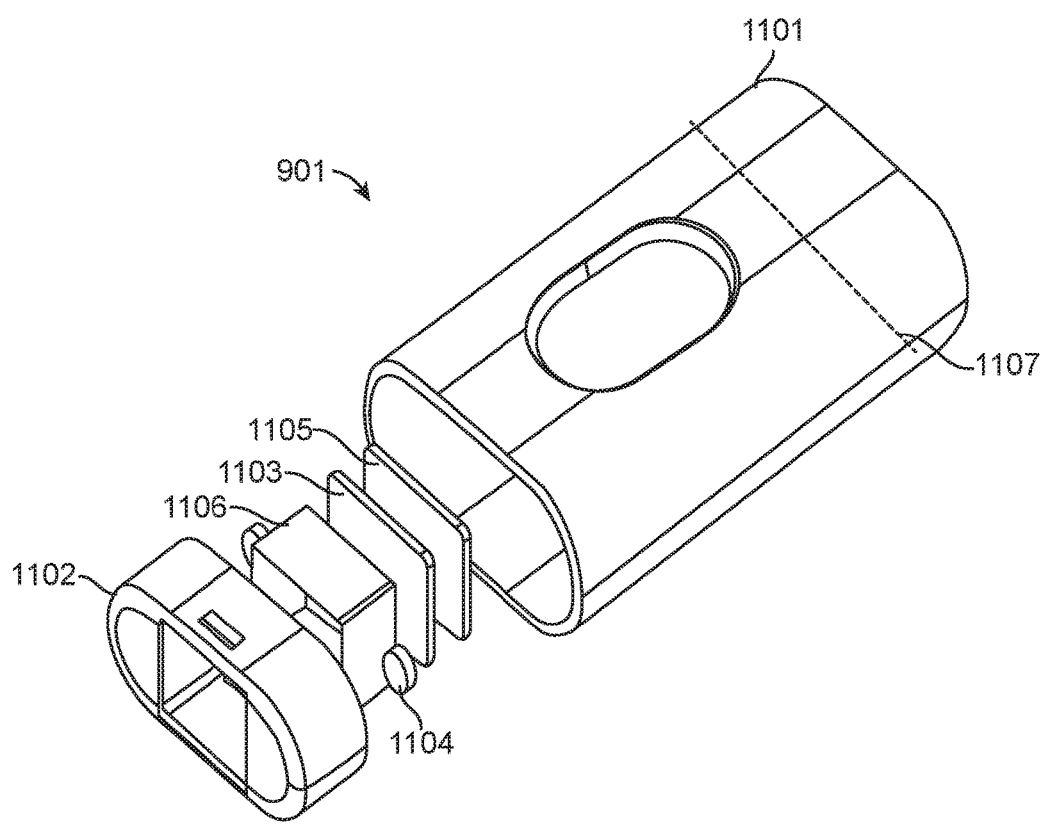
FIG. 11 shows an exploded assembly diagram of a cover.

FIG. 11 shows an exploded view of the cover 901. The cover can have a body 1101 and a base 1102. The base 1102 can house the reflective material 1103. In a full assembly (e.g. not exploded) the base 1102 can be placed into the body 1101. An approximate location of the base in the full assembly is shown by the dotted line 1107. The reflective material can be adhered to an inner surface of the cover with an adhesive 1105. The adhesive 1105 can be a compressible adhesive, for example, a foam. The base can house the reflective material 1103 in a reflector box 1106 embedded in the base. In some instances, the reflector box can have inner walls covered or coated with a reflective layer. The reflective layer material can be metallic, for example gold. The reflective layer can be a diffuse reflector. The reflective layer can be a specular reflector. The reflective layer coating the inner walls can act as a mirror such that the reflective material 1103 appears infinite to an incident light source. The infinite appearance of the reflective material 1103 can reduce or eliminate contamination from materials other than the reflective material 1103. The reflective material 1103 can have a substantially constant reflectivity. The substantially constant reflectivity can be known. The substantially constant reflectivity can be fixed to within about 1% for a constant wavelength light source. In some cases, the substantially constant reflectivity can be fixed to within about 1% for a range of wavelengths. The range of wavelengths can be a range of at least 400 nm. Alternatively, the substantially constant reflectivity can be variable for a range of wavelengths. The substantially constant reflectivity can vary no more than about 10% over a range of wavelengths of at least about 400 nm. The variability of the reflectivity as a function of wavelength can be known.

The base 1102 can further comprise one or more engagement structural features configured to couple or mate to a supports on the spectrometer. In many instances, the engagement structural features can be one or more magnets 1104. When inserted into the cover body 1101, the magnets 1009 on the spectrometer 100 can connect to the magnets 1104 on the base 1102.

The reflective material 1103 can be used to calibrate the spectrometer. The calibration can eliminate or correct for non-uniformities in the light source and/or the spectrometer. The spectrometer can further comprise a processor coupled to the sensor array. The processor can comprise a tangible medium embodying instruction to measure a calibration signal with the cover optically coupled to the sensor array. The processor can comprise instructions to adjust one or more calibration parameter in response to the calibration signal. The calibration parameters can be measurement signal properties. For example, the calibration parameters can be amplitude of a measurement signal comprising one or more a gain of the sensor array or an amount of light energy from the light source. The processor can comprise one or more substantially constant calibration parameters corresponding to the substantially constant reflective material. The processor can be in communication with a memory storage device on or off board the spectrometer that comprises expected or known properties of the constant reflective material. If the spectrometer measures a reflective property outside of the expected or known properties of the constant reflective material the processor can initiate a recalibration or adjustment of one or more calibration parameters. The processor can comprise instructions to adjust the one or more calibration parameters in response to the calibration signal and the one or more substantially constant calibration parameters.

The cover can be provided to calibrate the spectrometer. The calibration can be performed automatically by the spectrometer in response to a user instruction to perform the calibration. A user can instruct the spectrometer to perform the calibration by attaching the cover with the reflective material on the spectrometer, or by a physical user input (e.g. pushing a button or flipping a switch). In the case of automatic calibration, the spectrometer can be calibrated without an input signal from a user. The automatic calibration can be initiated by a processor on or off board the spectrometer. The processor can be configured to detect that the device requires calibration and initiate the calibration.

In many instances an automatic calibration algorithm can be initiated when a user turn the spectrometer on (e.g. presses the power button to complete a battery circuit to provide power to the spectrometer components). The processor can assume that the device is in the cover and aimed at the reflective material in the cover. The assumption can be confirmed by a sensor. For example, a sensor can be a switch indicating that the cover is mounted, or performing a quick reading with or without light source illumination to verify presence of the reflective material. Alternatively, the automatic calibration algorithm can be initiated when stored data in the cloud based storage system 118 for the calibration standard (e.g. reflective material) is older than a threshold age or below a threshold accuracy.

Calibration of the spectrometer can result in a more accurate measurement of a sample material. The cover can comprise a single piece of optically non-transmissive material for calibration. The optically non-transmissive material can comprise the reflective material. The reflective material can be a reference material with known optical properties. In some cases, the reference material can be a "white reference" material. A white reference material can be a material with a flat spectral response. The white reference material may comprise one or more of many known white reference materials, such as Spectralon™, commercially available from Labsphere, as published on the world wide web at the domain "labsphere.com".

Measurements of the white reference material can be used to remove non-uniformities in the light source and/or the spectrometer when measuring sample materials. The cover can provide the white reference material in a controlled environment for calibration. In some cases, the cover can provide the white reference material in an environment substantially free from ambient light and with a constant and known distance between the sensor and the sample material (e.g. white reference). Other possible materials are glass coated sheets, sand-blasted aluminum and other metals.

In many instances as described herein, calibration measurements are obtained with the "white reference" (hereinafter "WR") material with light or dark signals, and combinations thereof. In some cases, the measurement may comprise a "WR-dark" measurement when the illuminator is turned off. For many WR measurements, the sheath cover and reference material are placed on the spectrometer as described herein.

In many instances, the spectrometer can be calibrated by taking a "WR-dark" measurement. The "WR-dark" measurement can be a spectrometer measurement of the reference material without the illumination source. The "WR-dark" measurement can provide data on ambient light and other effects like sensor dark noise. Ambient light and other effects like sensor dark noise can inhibit measurement interpretation, therefore it can be helpful to quantify these parameters in order to subtract them out or disregard them in sample measurements. The "WR-dark" measurement can be repeated at least about 5, 10, 15, 20, 25, or 30 trials and the "WR-dark" measurement can be averaged over the repeated trials. The "WR-dark" measurement can be at least about 15 milliseconds long. After the "WR-dark" measurement is performed the white reference (WR) signal can be measured. In some cases, the "WR-dark" signal may not be measured and the calibration method can begin by measuring the WR signal. The WR signal can also be measured repeatedly or a series of repeated trials. The WR signal can be repeated for at least about 10, 20, 30, 40, 50, 60, 70, 80, 90, or 100 trials. Each measurement can take at least about 15 milliseconds. All of the WR signal measurement trials can be averaged. If a "WR-dark" measurement was taken the "WR-dark" measurement average can be subtracted from the average WR signal measurement. The WR signal measurement can be transmitted or otherwise communicated to the cloud based storage system 118. The cloud based storage system 118 can further validate the signal measurement and if valid the signal can be stored as a reference signal.

Figure 12:
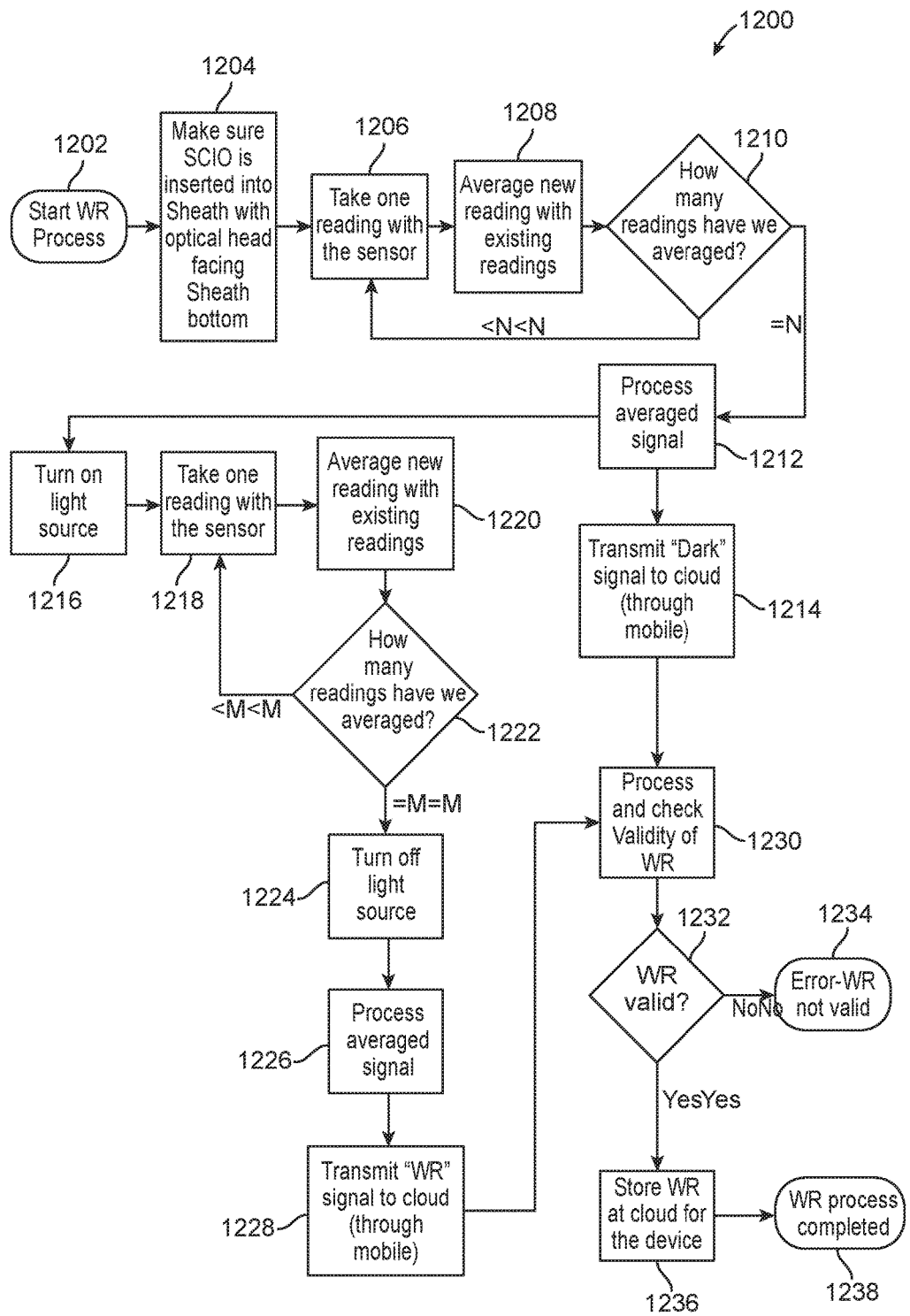
FIG. 12 shows a process flow diagram of a method of calibrating a spectrometer.

FIG. 12 shows a method 1200 that can be performed to automatically, semi-automatically, or manually, initiate and perform a calibration of the spectrometer. In a step 1202, the white reference process can initiate. In a step 1204, the spectrometer can detect that the cover is connected. The cover can comprise a reference reflective material as described herein. In a step 1204, it can be confirmed that the spectrometer is inserted into the cover or sheath and that the optical head of the spectrometer is correctly oriented toward the closed end of the cover. Correct orientation can be towards the bottom of the sheath. In a step 1206, a measurement or reading of the reference reflective material can be taken or collected. In a step 1208, the collected measurement can be averaged with previous measurements or subsequent measurements. In a step 1210, the total number of readings or measurements in the average can be considered. If the number of readings is below a value, N, where N is an integer greater than or equal to zero, step 1206 can be repeated. In a step 1212, which may occur when N is equal to a greater than a chosen threshold value, the average signal or measurement can be processed. In a step 1214, the measurement can be transmitted to a cloud based storage system 118. The signal can be transmitted through a mobile device. In step 1214, the measurement can be a dark measurement. In step 1216, the light source can be tuned on. In a step 1218, a measurement or reading can be collected or taken with the spectrometer sensor. In a step 1220, the measurement or reading can be averaged with previous measurements or subsequent measurements. In a step 1222, the total number of readings or measurements in the average can be considered. If the number of readings is below a value, M, where M is an integer greater than or equal to zero, step 1218 can be repeated. In a step 1224, the light source can be turned off. In a step 1226, which may occur when N is equal to a greater than a chosen threshold value, the average signal or measurement can be processed. In a step 1228, the measurement can be transmitted to a cloud based storage system 118. The signal can be transmitted through a mobile device. In a step 1230, the dark measurement and the light measurement can be combined to check the validity of a measurement of the reference material (e.g. white reference). In a step 1232, a binary decision can be made regarding the validity of the measurement of the reference material. In a step 1234, an error can indicate that the decision is that the measurement is not valid. In a step 1236, the measurement can be valid and stored on the cloud device 118. In a step 1238, the calibration method can be determined to be complete.

FIG. 12 shows a method 1200 of calibrating a spectrometer. A person of ordinary skill in the art will recognize many variations, alterations and adaptations based on the disclosure provided herein. For example, the order of the steps of the method can be changed, some of the steps removed, some of the steps duplicated, and additional steps added as appropriate. Some of the steps may comprise sub-steps. Some of the steps may be automated and some of the steps can be manual. The processor as described herein may comprise one or more instructions to perform at least a portion of one or more steps of the method 1200.

In many instances, the accessory 909 may comprise structural features that are configured to orient the sample with a defined and repeatable position and orientation relative to the spectrometer light source and/or a spectrometer detector. The accessory can be configured to position and orient a liquid or solid sample. The accessory 909 can comprise a cavity with a structure such as a groove, indentation, dent, depression, hole, ridge, and/or any other physical structure configured to hold a sample with a predetermined orientation relative to the spectrometer. In some cases, the accessory can be configured to center the sample in the cavity. Samples with different shapes can orient in the structural feature in a similar way each time they are measured such that consistency between measurements on the same sample can be achieved. In some cases, the sample can be small relative to the spectrometer. In some cases the sample can be a pill (e.g., paramedical pill). A plurality of accessories can be provided in which each accessory comprises a structural recess sized and shaped to receive a specific object such as a specific pill formulation of a medication.

Figure 13:
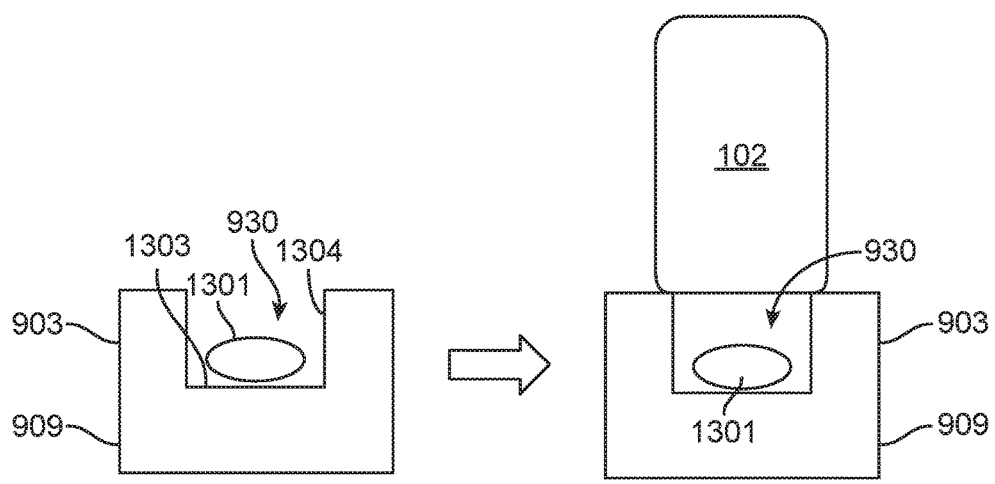
FIG. 13 shows a method of placing a sample in an accessory for measurement of the sample.

FIG. 13 shows a schematic diagram of a pill sample 1301 placed in a sample container 903 comprising an accessory 909. The sample 1301 can be placed in a structure 1303 configured to hold the sample in a predetermined orientation in the accessory relative to the spectrometer during a measurement. The inner walls 1304 of the structure 1303 can be coated with a reflective material. The inner walls of the structure 1303 can be coated with a metallic material. In some cases, at least one inner surface of the structure can be coated with a spectrally flat diffusive material (e.g., Spectralon™). The spectrally flat diffusive material can be behind the sample when the sample is placed in the structure. The inner walls of the structure 1303 can comprise the walls and/or surfaces of the structure 1303 that surround the sample. The accessory 909 can be sized and configured such that the accessory 909 can be placed on a surface while the sample is measured. The surface can comprise a stable surface such as a table or other smooth level surface. To measure the sample 1301 the spectrometer 102 can be fitted on the accessory 909. The spectrometer and the accessory can be connected by complementary magnets provided on the spectrometer and the accessory. When the spectrometer 102 is placed on the accessory 909 the sample 1301 can be enclosed between the spectrometer and the accessory such that ambient light cannot reach the sample. In many instances, the spectrometer is sized and shaped to fit onto the accessory container.

Figure 14A:
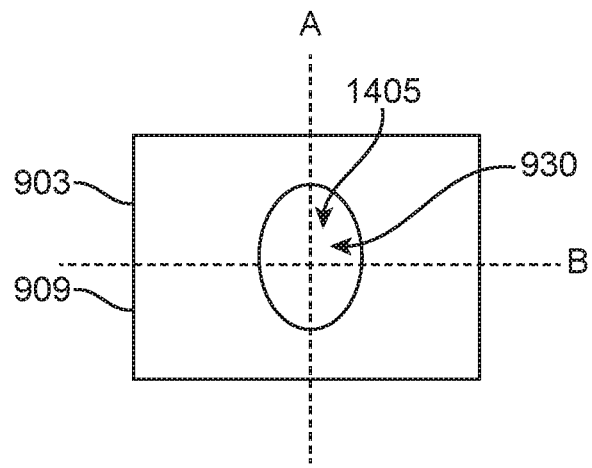
FIG. 14A shows a top view of a structure that can be provided on an accessory configured to orient a sample.
Figure 14B:
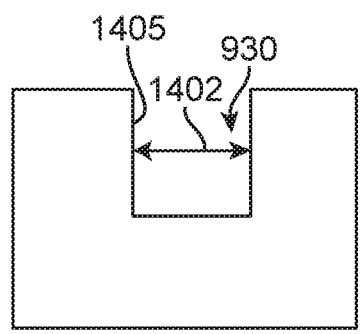
FIG. 14B shows a first cross section view of a structure that can be provided on an accessory configured to orient a sample.
Figure 14C:
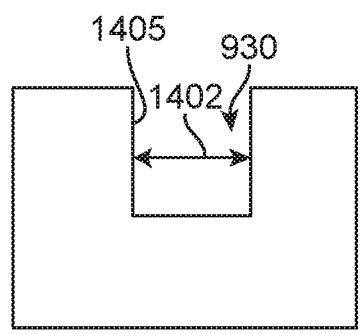
FIG. 14C shows a second cross section view of a structure that can be provided on an accessory configured to orient a sample.
Figure 15A:
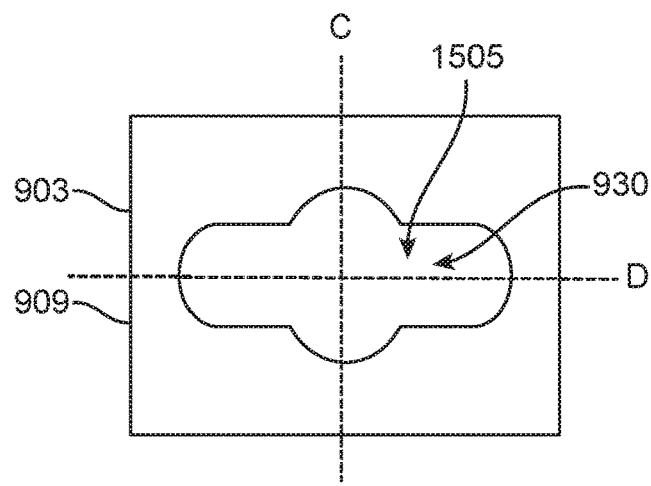
FIG. 15A shows a top view of a structure that can be provided on an accessory configured to orient a sample.
Figure 15B:
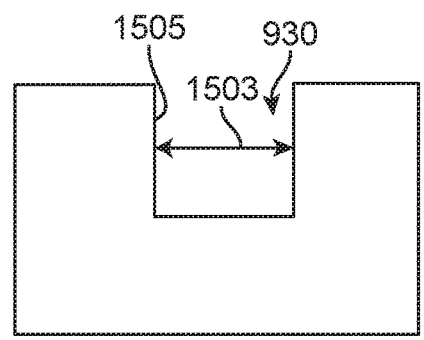
FIG. 15B shows a cross section view of a structure as in FIG. 15A that can be provided on an accessory configured to orient a sample.
Figure 15C:
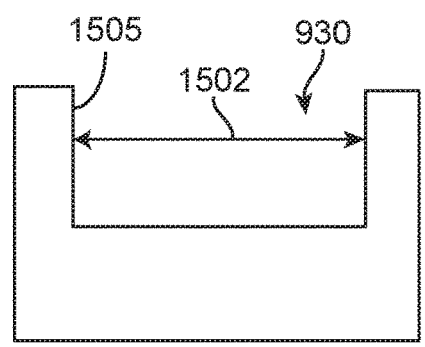
FIG. 15C shows a top view of a structure as in FIGS. 15A and 15B that can be provided on an accessory configured to orient a sample.

FIG. 14A shows a top view of an accessory 909 comprising sample container 903 with structures that can be sized and shaped hold a solid object. In a first case the accessory comprises a first structure with a circular depression 1405 comprising a channel 930. The circular depression can have a diameter 1402 of at least about 1 mm, 5 mm, 10 mm, 15 mm, 20 mm, 25 mm, 30 mm, 35 mm, 40 mm, 45 mm, or 50 mm, for example. The circular depression is shown a in a top view of the accessory. A cross section along line A (shown in FIG. 14B) and a cross section along line B (shown in FIG. 14 C) can be identical. The accessory shown in FIG. 14A can be configured to hold a sample with a circular or spherical shape. The accessory shown with FIG. 14A can be configured to hold a circular or spherical pill, for example. In a second case shown in FIG. 15A, the accessory 909 comprising sample container 903 can have a second structure with an irregular depression 1505, comprising a channel 930. The irregular depression can have a longest dimension 1502 of at least about 1 mm, 5 mm, 10 mm, 15 mm, 20 mm, 25 mm, 30 mm, 35 mm, 40 mm, 45 mm, or 50 mm. The irregular depression can have a relatively shorter dimension 1503 of at least about 1 mm, 5 mm, 10 mm, 15 mm, 20 mm, 25 mm, 30 mm, 35 mm, 40 mm, 45 mm, or 50 mm. The irregular depression can generally be described as a circle laid over an oblong shape. The irregular depression is shown a in a top view in FIG. 15A of the accessory 903. In the second case a cross section along line C (shown in FIG. 15B) and a cross section along line D (shown in FIG. 14C) can have different widths such that one of the depressions shown in the two cross sections is longer than the other. The accessory shown and described by the second case can be configured to hold a sample with a circular, spherical, or oblong shape. The accessory shown and described by the first case can be configured to hold a circular, spherical, or oblong pill.

Figure 16:
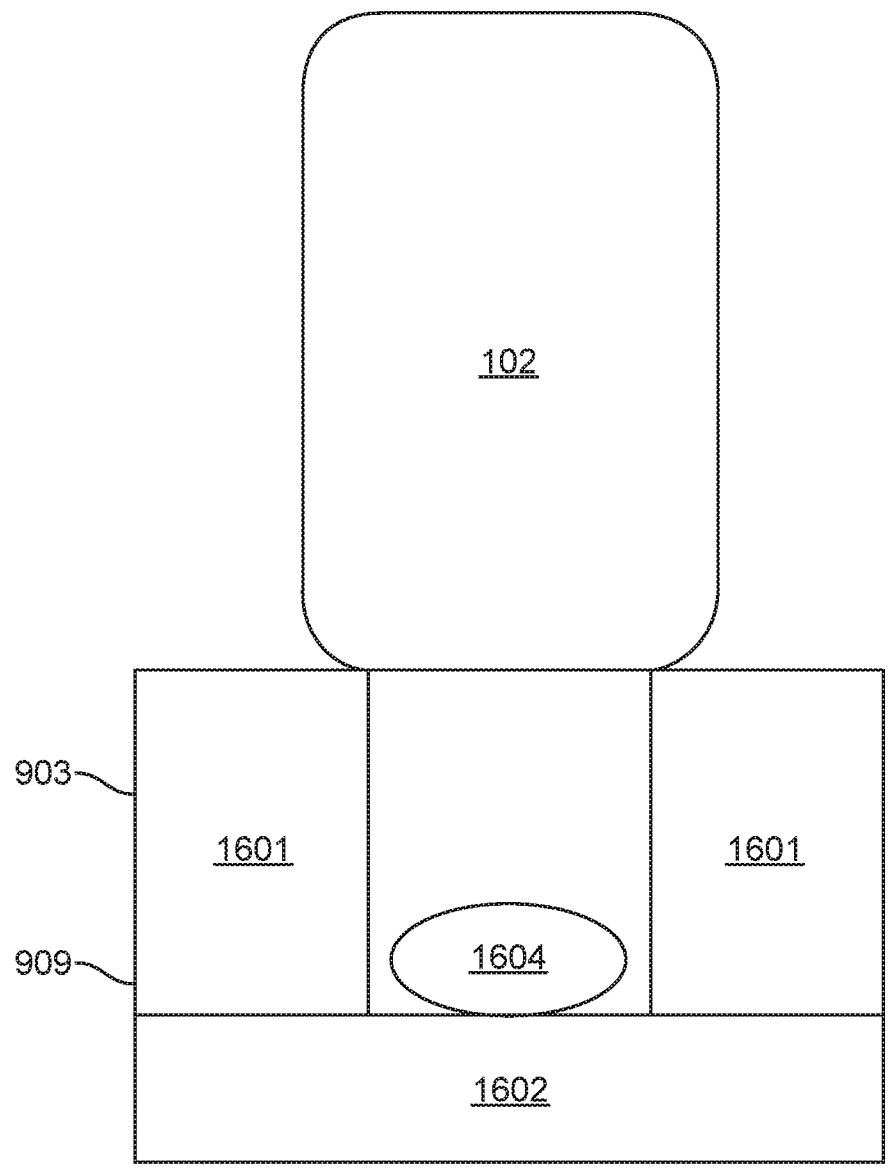
FIG. 16 shows an accessory comprising a plurality of connectable parts.

In some instances, the accessory can comprise a plurality of parts. The parts can be mechanically connected to form the accessory. In some cases the parts can be connected by a magnetic connection to form the accessory 909 comprising container 903. FIG. 16 shows a schematic of an accessory 909 comprising a plurality of connectable parts. In some cases the accessory can comprise more than two connectable parts. In the instances shown in FIG. 16, a first part 1601 can connect to a second part 1602. The first part 1601 and the second part 1602 can be connected by a mechanical fit or a magnetic connection. Additionally, the spectrometer 100 can be fitted on the first part 1601 for measuring of a sample inside the accessory container 903. The spectrometer 102 can be fitted on the first part 1601 with a magnetic connection. The magnetic connection between the spectrometer 102 and the first part 1601 can be stronger than the magnetic connection between the first part 1601 and the second part 1602. In some cases, the sample 1604 can be placed on the second part 1602 before the first part 1601 and the second part 1602 are connected. Placing the sample 1604 on the second part 1602 before the first part 1601 is connected may permit a user to achieve a desired orientation of the sample 1604 on the second part 1602 without being obstructed by the first part 1601.

Figure 17:
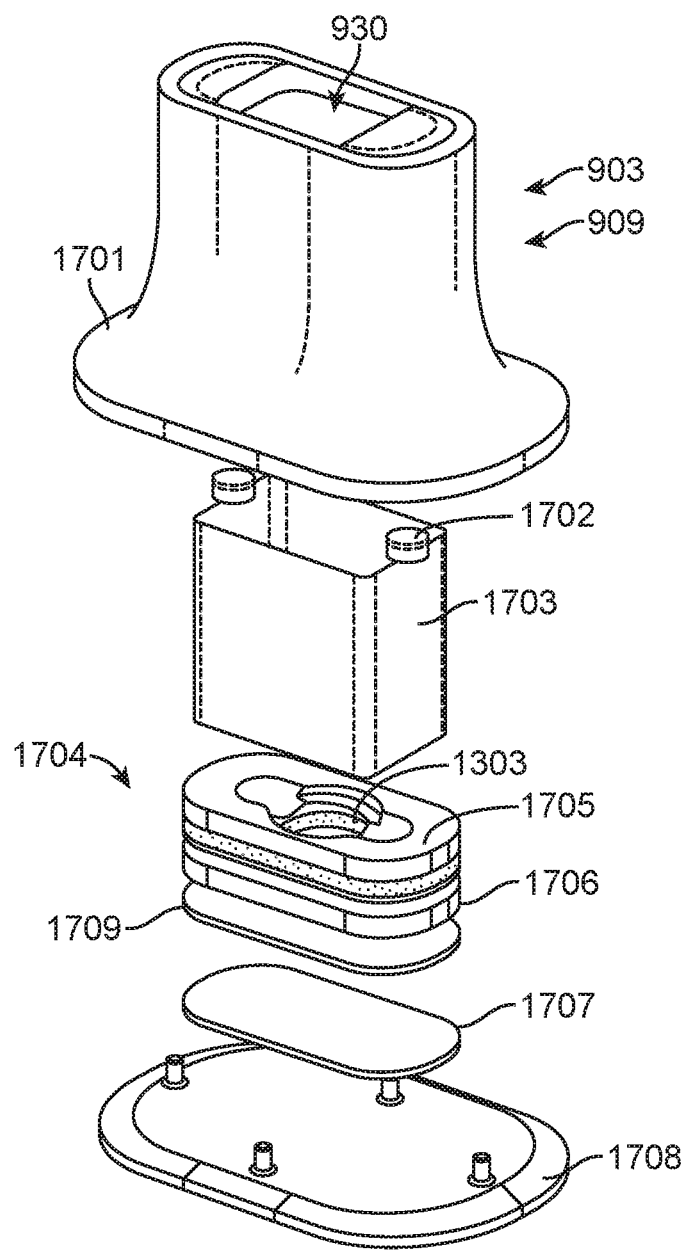

FIG. 17 shows a detailed exploded view of an accessory 909 comprising sample container 903. The accessory can comprise a body 1701 having a channel 930. The body can be a housing for one or more components of the accessory to fit inside of the body 1701. The body can comprise two or more magnets 1702. The two or more magnets can be configured to connect with two or more magnets on a spectrometer or a magnetic surface of the spectrometer when the accessory container 903 is connected to the spectrometer. At least a fraction of the inside of the housing can be coated with or coupled to a reflective box comprising a reflective material 1703. The reflective material 1703 can be a metallic material. When the sample is being measured, the reflective material can reflect at least a fraction of the light emitted by a light source of the spectrometer. The spectrometer housing can comprise an insert 1704 comprising the structure 1303 configured to hold the sample in a predetermined position and orientation.

The insert 1704 can comprise a top surface 1705. The top surface can be a surface that faces the spectrometer during measurement of the sample. The top surface 1705 can be coated with a diffusive and/or spectrally flat coating. Similarly, the bottom surface 1706 of the insert 1704 can comprise a diffusive and/or spectrally flat coating. The bottom surface can be a surface that is behind the sample when the sample is measured by the spectrometer. The insert 1704 can be connected to a base 1708 of the accessory with an adhesive 1707. The base 1708 can connect to the body 1701 of the accessory 903 to fully enclose the components in the accessory 903. A reflective foil 1709 can be placed adjacent to a surface of the structure. The reflective foil can prevent stray ambient light from entering the structure 1303 of the insert 1704. In some cases, a foam (not shown) can be placed between the foil 1709 and the adhesive 1707. The foam can be chosen such that a desired spacing can be provided between the sample and the light source. A thinner foam can be used to increase the distance between the light source and the sample while a relatively thicker foam can be used to decrease the distance between the light source and the sample.

Figure 18A:
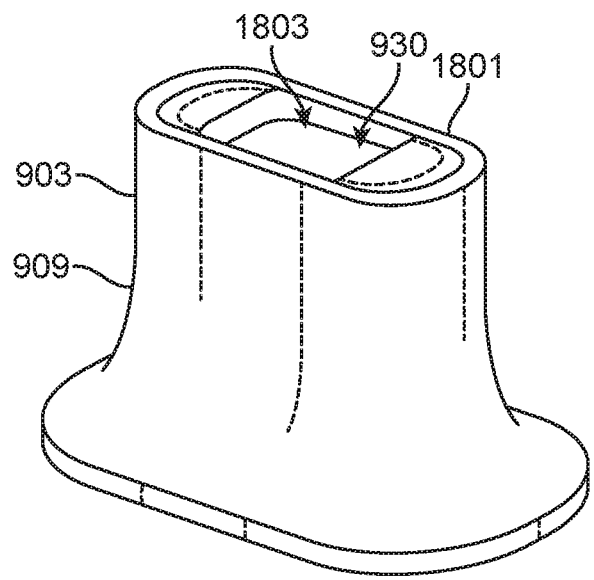
FIGS. 18A and 18B show perspective and a cross sectional diagrams, respectively, of an accessory.
Figure 18B:
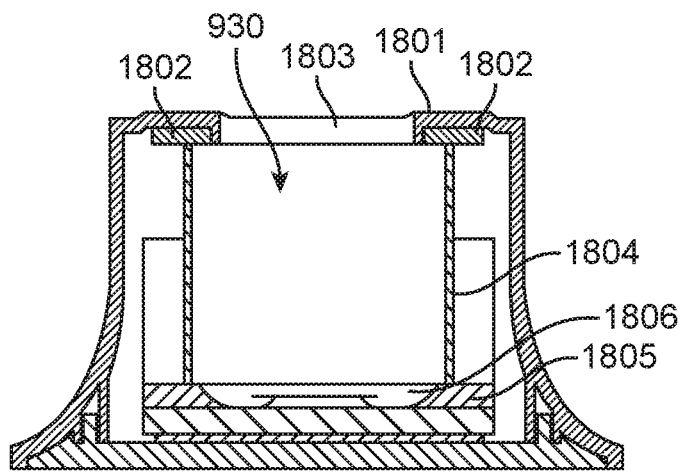

FIG. 18A shows a perspective view of an assembled accessory 909 comprising sample container 903. FIG. 18B shows a cross sectional view of the accessory 909 comprising the container 903. The accessory can have a first end 1801 configured to connect to the spectrometer. The first end can comprise two or more magnets 1802 configured to connect to two or more magnets or a magnetic surface of the spectrometer. The first end 1801 can comprise an opening 1803 through which a sample can be loaded into a channel 930 of the accessory. The inner walls 1804 of the accessory can comprise a reflective coating. A bottom surface 1805 of the accessory can comprise a depression 1806 configured to hold a sample.

The method of calibrating the sample can be used to measure the sample with the accessory holder as described herein, and the method of measuring may comprise one or more steps of the method of calibrating.

The accessories, covers and containers as described herein are well suited for use with many types of spectrometers, including hand held and stationary spectrometers.

In some instances an accessory can be configured to permit measurement of a liquid sample. The liquid sample can comprise a clear or opaque liquid. The liquid sample can comprise a solution, a slurry, a Newtonian fluid, a non-Newtonian fluid, a homogenous mixture, or an inhomogeneous mixture. In some cases the liquid sample can comprise gas bubbles. The liquid sample can comprise a liquid that can be consumed by an animal (e.g., milk, water, carbonated beverage, alcoholic beverage, or juice). The liquid sample can comprise motor oil. The liquid sample can comprise urine. The liquid sample can comprise blood.

The accessory can be formed from a material that is safe for use with food and/or drink. The accessory can be formed from a material that will not contaminate food and/or drink with a chemical that is toxic for consumption by an animal. In some cases, the accessory can be formed from a material that can be washed by hand or in a dishwasher without melting, degrading, and/or breaking. In some instances, the accessory can be formed from a material that is disposable. The disposable material can comprise laminated paper or cardboard.

The inner walls of the channel formed in an accessory or sample container as described herein may comprise a substantially light-absorbing material, such that when the spectrometer is coupled to the accessory, light from the illumination module that hits the inner walls is absorbed by the inner walls rather than reflected back into the channel. For example, the inner walls may be coated with a substantially light-absorbing material, or the inner walls may be formed from a substantially light-absorbing material.

Figure 19B:
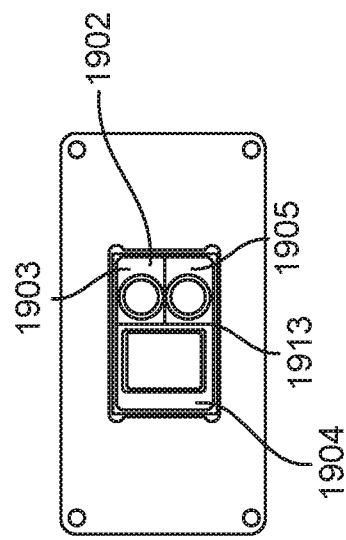
FIG. 19B shows a window provided on an accessory configured to perform a measurement of a liquid sample.
Figure 19A:
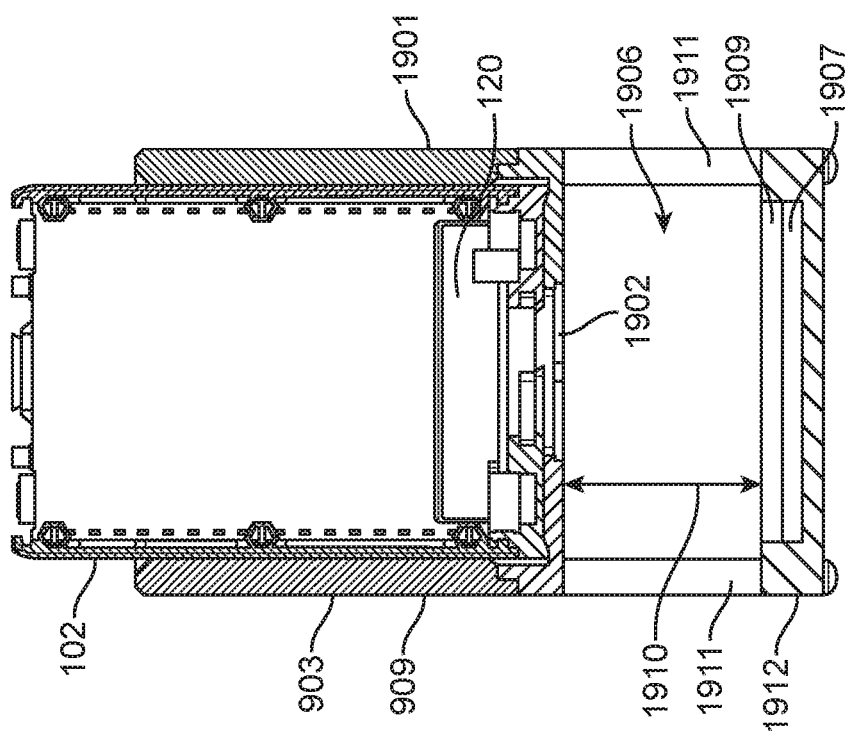
FIG. 19A shows a cross section view of a spectrometer fitted in an accessory configured to perform a measurement of a liquid sample.

FIG. 19A shows a cross section view of a spectrometer 102 coupled to an accessory 909 comprising a sample container 903 configured to permit measurement of a liquid sample. The accessory 909 can comprise a protective cover 1901. The spectrometer 102 can be fitted in the protective cover 1901 when the spectrometer is connected to the accessory. The spectrometer and the protective cover 1901 can form a liquid tight seal. The spectrometer and the protective cover 1901 can form an air tight seal. When the spectrometer is fitted and connected to the accessory liquid may not be able to permeate a boundary between the spectrometer and the protective cover. The protective cover can prevent liquid from contacting the spectrometer. The protective cover can prevent liquid from damaging the spectrometer. The seal formed between the spectrometer can the protective cover can comprise a gasket, o-ring, or other mechanical seal, for example. The seal formed between the spectrometer and the protective cover can comprise a rubber, Teflon, plastic, or metal seal, for example.

When the spectrometer 102 is coupled to the accessory 909, the spectrometer head 120 can be adjacent to a window 1902 of the accessory. The window can comprise a single window. The window can comprise two or more windows arranged in a single plane. The window can comprise two or more windows arranged on the same surface. The window can be formed from glass, plastic, or any other material configured to permit transmission of light. The window can be configured to permit transmission of light within a predetermined range of wavelengths. In cases where two or more windows are provided on the window, two or more of the windows can be configured to permit transmission of light in different wavelength ranges, for example.

FIG. 19B shows a surface of a window 1902 that can be provided on the accessory 909. The window can have a convex shape such that any gas bubbles that exist on the window will roll off by buoyancy when the spectrometer is oriented with an elongate axis of the spectrometer extending vertically. Reducing and/or eliminating gas bubbles on the window 1902 can ensure an accurate spectroscopy measurement of the liquid. In some cases one or more channels can be provided on the window to reduce or eliminate gas bubbles.

The window shown in FIG. 19B can comprise a first window 1903 configured to permit illumination light from the spectrometer to enter a liquid sample contained in the accessory 903. The window 1902 may comprise a second window 1904 and a third window 1905. Each of the first window, the second window and the third window can be optically isolated from each other in order to inhibit interference of signals. An opaque material 1913 can extend between the windows in order to inhibit cross-talk and light traveling from one window to the other windows. The windows may comprise energy transmission channels to transmit light to or from the sample. For example, the each window may comprise an energy transmission channel. Each of the channels can be optically isolated from each other. Alternatively or in combination, each of the energy transmission channels may comprise a material to transfer energy in addition to or alternatively to light energy. For example, one or more of the energy transmission channels may comprise a metal to relay heat energy from the sample to the metal and from the metal to an infrared temperature sensor.

The first window 1903 can be arranged adjacent to the illumination window 142 (shown in FIG. 3) of the spectrometer 102 when the spectrometer is fitted in or coupled to the accessory. The first window 1903 can be arranged adjacent to the illumination window 142 of the spectrometer 102 when the spectrometer is fitted in the accessory such that edges of the first window 1903 are aligned with edges of the illumination window 142 of the spectrometer 102. The first window 1903 can be arranged adjacent to the illumination window 142 of the spectrometer 102 when the spectrometer is fitted in the accessory such that a perimeter of the first window 1903 is aligned with a perimeter of the illumination window 142 of the spectrometer 102. The first window 1903 can be arranged adjacent to the illumination window 142 of the spectrometer 102 when the spectrometer is fitted in the accessory such the first window 1903 is aligned with the illumination window 142 of the spectrometer 102. The first window 1903 can be arranged adjacent to the illumination window 142 of the spectrometer 102 when the spectrometer is fitted in the accessory such the first window 1903 is coaxial with the illumination window 142 of the spectrometer 102.

The window 1902 can further comprise second window 1904 configured to permit light to travel from the sample to the spectrometer. The second window 1904 can be arranged adjacent to the spectrometer window 162 (shown in FIG. 3) of the spectrometer 102 when the spectrometer is fitted in or coupled to the accessory. The second window 1904 can be arranged adjacent to the spectrometer window 162 of the spectrometer 102 when the spectrometer is fitted in the accessory such that edges of the second window 1904 are aligned with edges of spectrometer window 162 of the spectrometer 102. The second window 1904 can be arranged adjacent to the spectrometer window 162 of the spectrometer 102 when the spectrometer is fitted in the accessory such that a perimeter of the second window 1904 is aligned with a perimeter of the spectrometer window 162 of the spectrometer 102. The second window 1904 can be arranged adjacent to the spectrometer window 162 of the spectrometer 102 when the spectrometer is fitted in the accessory such the second window 1904 is aligned with the spectrometer window 162 of the spectrometer 102. The second window 1904 can be arranged adjacent to the spectrometer window 162 of the spectrometer 102 when the spectrometer is fitted in the accessory such the second window 1904 is coaxial with the spectrometer window 162 of the spectrometer 102.

The window 1902 can further comprise third window 1905 configured to permit measurement of a temperature of the liquid sample contained in the accessory 909. The third window 1905 can be arranged adjacent to the temperature sensor window 132 of the spectrometer 102 when the spectrometer is fitted in or coupled to the accessory. The third window 1905 can be arranged adjacent to the temperature sensor window 132 (shown in FIG. 3) of the spectrometer 102 when the spectrometer is fitted in the accessory such that edges of the third window 1905 are aligned with edges of temperature sensor window 132 of the spectrometer 102. The third window 1905 can be arranged adjacent to the temperature sensor window 132 of the spectrometer 102 when the spectrometer is fitted in the accessory such that a perimeter of the third window 1905 is aligned with a perimeter of the temperature sensor window 132 of the spectrometer 102. The third window 1905 can be arranged adjacent to the temperature sensor window 132 of the spectrometer 102 when the spectrometer is fitted in the accessory such the third window 1905 is aligned with the temperature sensor window 132 of the spectrometer 102. The third window 1905 can be arranged adjacent to the temperature sensor window 132 of the spectrometer 102 when the spectrometer is fitted in the accessory such the third window 1905 is coaxial with the temperature sensor window 132 of the spectrometer 102.

The third window 1905 can be configured to permit transmission of an optical temperature measurement signal. The optical temperature measurement signal can comprise light with a wavelength in a range of about 1 μm to about 100 μm. The optical temperature measurement signal can comprise light with a wavelength in a range of about 1 μm to about 50 μm. The optical temperature measurement signal can comprise light with a wavelength in a range of about 5 μm to about 25 μm. The optical temperature measurement signal can comprise light with a wavelength in a range of about 4 μm to about 8 μm. The third window 1905 can comprise a germanium window, for example. The third window can be transmissive to light with a wavelength within the range of the optical temperature measurement signal wavelength range.

Alternatively or additionally, the third window can comprise a material with low heat capacitance, high thermal conductivity, and high emissivity. In some cases the third window can comprise a material with a heat capacitance of at most about 10 J/g·° C., 5 J/g·° C., 1 J/g·° C., 0.5 J/g·° C., 0.1 g·° C., or 0.01 g·° C. In some cases, the third window can comprise a material with a thermal conductivity of at least about 25 W/m·K, 50 W/m·K, 75 W/m·K, 100 W/m·K, 150 200 W/m·K, 250 W/m·K, 300 W/m·K, 350 W/m·K, 400 W/m·K, 450 W/m·K, or 500 W/m·K. In some cases, the third window can comprise a material with an emissivity of at least about 0.01, 0.02, 0.03, 0.04, 0.05, 0.1, 0.5, 0.75, 0.8, 0.9, or 1. The third window can comprise a thin metal (e.g., steel, brass, copper, aluminum, or iron) plate. The third window can comprise a metal sheet. The third window can comprise a plate formed from anodized aluminum. In some cases, a temperature of the window can be measured instead of or in addition to measuring a temperature of the liquid sample. The window can be configured to adjust to the temperature of the liquid sample within about 1 s, 0.5 s, 0.1 s, 0.05 s, 0.01 s, 0.005 s, 0.001 s, 0.0005 s, or 0.0001 s after contacting the liquid sample. A measurement of the window temperature can provide an accurate measurement of the liquid sample within about +5° C., +1° C., +0.5° C., +0.1° C., +0.05° C., +0.01° C., +0.005° C., or +0.001° C.

During measurement of a liquid sample, the spectrometer 102 fitted in the accessory 909 can be dipped into a liquid. Dipping the spectrometer into the liquid can reduce specular reflection of illumination light from a liquid surface. In some cases, specular reflections of illumination light from a liquid surface can confuse or inhibit acquisition of an accurate spectrometry measurement. In some cases, if the spectrometer is not dipped into the liquid transition of illumination from the liquid to air between the spectrometer and a surface of the liquid can cause light refraction. Light refraction can confuse or inhibit acquisition of an accurate spectrometry measurement. Dipping the spectrometer in the liquid can avoid the issues of specular reflections and/or light refraction that can occur as a result of illumination off of the surface of the liquid. When a user dips the attachment coupled to the spectrometer in a liquid the user can perform one or more steps to decrease formation of gas bubbles between the accessory window 1902 and the liquid for sampling. In some cases, a user can decrease formation of gas bubbles between the accessory window 1902 and the liquid for sampling by first dipping the accessory in with an elongate axis of the spectrometer at an angle less than 90° relative to the surface of the liquid.

When the spectrometer 102 fitted in the accessory 909 is dipped in a liquid for measurement of the liquid, a volume of liquid can fill a space 1906 that forms between the window 1902 and the reflective element 1907. In some cases, the space 1906 can be fully enclosed by opaque walls to prevent ambient light from interfering with a spectroscopy measurement. The walls may comprise one or more openings, for example a plurality of openings, to allow liquid to enter the space and gas to exit the space 1906 defined by the walls of the measurement chamber. The inside of a wall can be a side that contacts the liquid volume enclosed by the walls. The inside of a wall can be coated with a reflective coating. Alternatively the inside of a wall can be coated with a material that absorbs light. The inside of a wall can be coated with a material that does not reflect light. At least one of the walls can be opened and/or removed prior to a measurement to permit liquid to enter the space. At least one of the walls can be opened by a hinge connection. In some instances, at least one of the walls can comprise one or more openings configured to permit liquid to enter the space 1906. In some cases, the space 1906 can be open on at least one side to permit easy flow of liquid into the space for sampling. The space 1906 can be free of walls, and in some cases, posts can connect the accessory to the platform. The posts will be described in detail elsewhere herein.

The reflective element 1907 can comprise a material that is a diffuse reflector. The diffuse reflector can be embedded in a platform 1912, for example placed in a recess of platform 1912. The reflective element 1907 can comprise a material that is a specular reflector. The reflective element can comprise a material that is both a specular and diffuse reflector. The reflective element can comprise a smooth coating (e.g., polished gold coating) to permit specular reflection. A protective layer 1909 can be provided over the reflective element to protect the reflective element from the liquid. A protective layer 1909 can be provided over the reflective element to prevent the reflective element from contacting the liquid. A protective layer 1909 can be provided over the reflective element to prevent the reflective element from getting wet. The protective layer 1909 can be transparent. The protective layer 1909 can be glass. The protective layer 1909 can be plastic. The protective layer 1909 can be a cured transparent resin. In some cases, the reflective material can be formed from a material that is resistant to liquids. The reflective material can be formed from a material that can be exposed to a liquid without breaking, eroding, reacting, or becoming unusable, for example. In some cases, the reflective element can be formed from opal glass or sand blasted metal (e.g., aluminum, steel, copper, brass, or iron). In cases where the reflective element is resistant to liquids the protective layer can be omitted. In some cases, the reflective element can comprise a diffuser placed over a reflecting substrate.

In some configurations, the reflective element 1907 may comprise a diffuser placed over a light-blocking and light-absorbing material (such as an anodized aluminum foil or plate). A diffuser placed over a light-absorbing substrate may produce a reflectance spectral response with better flatness and stability than a diffuser placed over a reflecting substrate. If the diffuser is thick enough, there may be no need for a separate substrate as the forward transmitted light may be weak enough, and the backscattering strong enough.

Illumination from the illumination module can illuminate a volume of liquid contained in the space 1906 that fills with the volume of liquid when the spectrometer fitted in the accessory is dipped in a liquid. The reflective layer can increase the amount of light reflected towards the spectrometer. The reflective layer can increase the intensity of light that is reflected towards the spectrometer. The reflective layer can increase accuracy by increasing signal from liquids that are transparent (e.g., transparent to light in the IR range). The reflective layer can increase accuracy by increasing signal from liquids with low scattering characteristics.

The reflecting element 1907 may be particularly helpful for the measurement of spectra of essentially clear or lucid liquids (e.g., measurement of the percentage of alcohol in Vodka), and may be of relatively lesser importance for the measurement of highly diffusive liquids (e.g., measurement of the percentage of fat in milk). The use of a reflecting element or base for the measurement of clear liquids can be important both for minimizing the reflection of light from background objects (such as the base of the liquid sample container) and for increasing the intensity of light passing from the illumination module through the liquid and into the spectrometer.

A distance 1910 between the window 1902 and the reflective element 1907 can influence the accuracy of a spectroscopy measurement. The distance 1910 can be at least about 1 mm, 2 mm, 3 mm, 4 mm, 5 mm, 6 mm, 7 mm, 8 mm, 9 mm, 10 mm, 15 mm, 20 mm, 25 mm, 30 mm, 35 mm, 40 mm, 45 mm, or 50 mm. The distance 1910 can define the volume of the liquid contained in the space 1906. In some cases, the distance 1910 can be adjustable. Two or more posts 1911 can connect the window 1902 of the accessory and the reflective element. The posts can be permanently or removable attached to either or both of the accessory and a platform 1912 comprising the reflective element. In some cases, a first set of posts can be disconnected from the platform and the accessory and replaced with a second set of posts with a longer or shorter length relative to the first set of posts.

Figure 20:
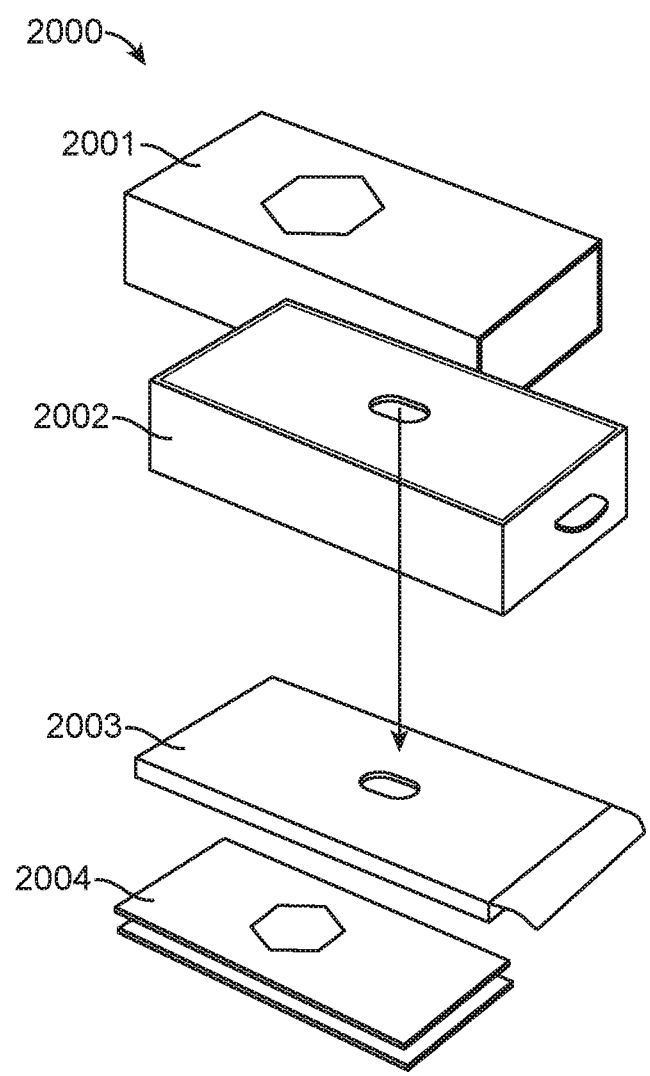
FIG. 20 shows a package in which a spectrometer kit can be housed.

The spectrometer 102 can be packed for sale and/or delivery. The package can comprise the spectrometer. The package can comprise one or more accessories 909 for use with the spectrometer. FIG. 20 shows a package that can house a kit comprising the spectrometer and one or more accessories. The accessories can comprise any of the accessories described herein. The accessories can comprise accessories for measuring of liquids, measuring of solids, measuring of pills, and/or calibration of the spectrometer.

The package 2000 can comprise an outer box 2001. An inner box 2002 can slide into the outer box 2001. An inner box 2002 can be size and shaped such that it fits into the outer box 2001. A tray 2003 can additionally be fitted in the outer box. Alternatively the tray can be fitted in the inner box. The spectrometer and one or more accessories can be contained in the inner box 2002. Instructions for use 2004 can be fitted in the tray.

Figure 21:
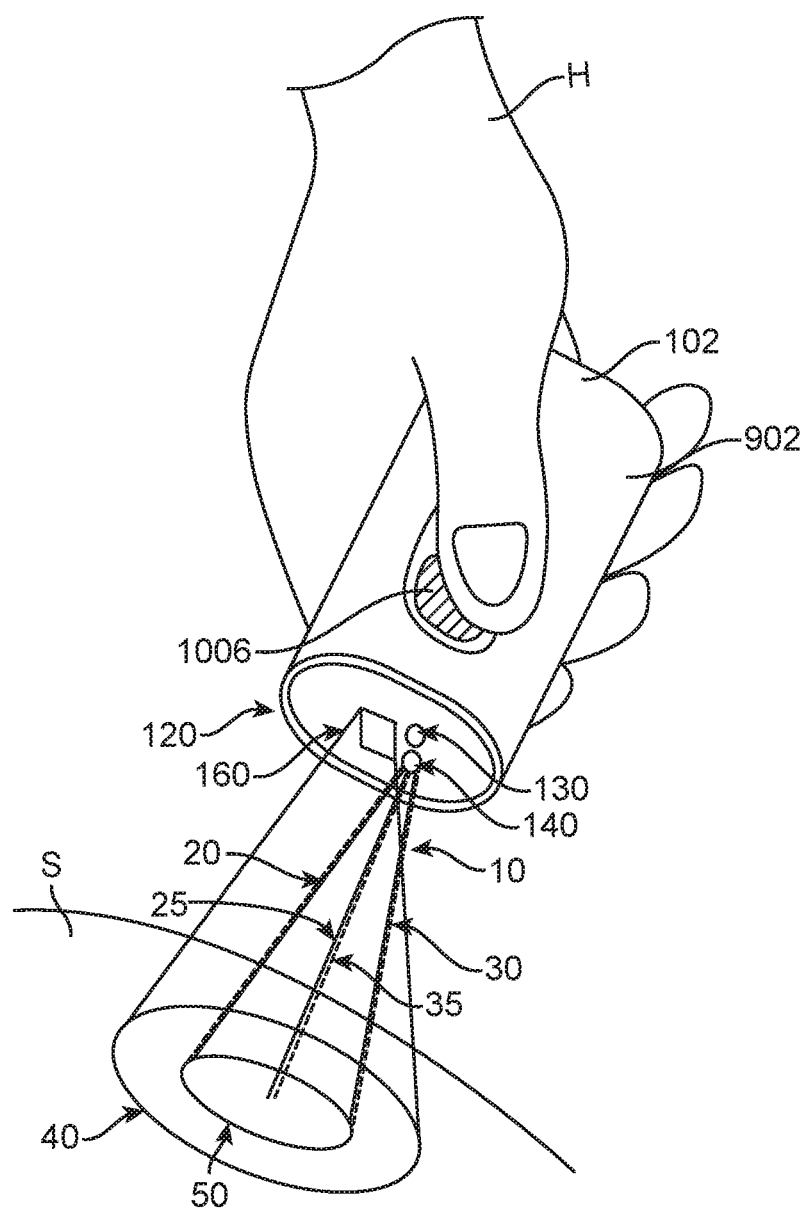
FIG. 21 shows an isometric view of a compact hand held spectrometer.

Referring now to FIG. 21, a user may initiate a measurement of a sample material S using the spectrometer 102 by interacting with a user input supported with a container 902 of the spectrometer. Although the spectrometer is shown without an accessory covering the measurement end of the spectrometer, one or more accessories as described herein can be placed on the measurement end and the spectrometer used similarly. The user input may, for example, comprise an operating button 1006. The container 902 may be sized to fit within a hand H of a user, allowing the user to hold and aim the spectrometer at the sample material, and manipulate the user input with the same hand H to initiate measurement of the sample material. The container 902 can house the different parts of the spectrometer such as the spectrometer module 160, illumination module 140, and sensor module 130. The spectrometer module may comprise a detector or sensor to measure the spectra of the sample material within a field of view 40 of the detector or sensor. The detector may be configured to have a wide field of view. The illumination module may comprise a light source configured to direct an optical beam 10 to the sample material S within the field of view 40. The light source may be configured to emit electromagnetic energy, comprising one or more of ultraviolet, visible, near infrared, or infrared light energy. The light source may comprise one or more component light sources. The field of view 40 can define the portion of the sample material S from which the spectral data is collected by the spectrometer 102. The illumination module may further comprise one or more optics coupled to the light source to direct the optical beam 10 toward the sample material S. The one or more optics may comprise one or more of a mirror, a beam splitter, a lens, a curved reflector, or a parabolic reflector, as described in further detail herein. The spectrometer 102 may further comprise circuitry coupled to the detector and the light source, wherein the circuitry is configured to transmit the optical beam 10 in response to user interactions with the user input using hand H holding the spectrometer. When a user initiates a measurement of a sample material S using the spectrometer 102, for example by pressing the operating button 1006 with hand H, the spectrometer emits an optical beam 10 toward the sample material within the field of view 40. When the optical beam 10 hits the sample material S, the light may be partially absorbed and/or partially reflected by the sample material; alternatively or in combination, optical beam 10 may cause the sample material to emit light in response. The sample emission, which may comprise at least a portion of the optical beam 10 reflected back by the sample and/or light emitted by the sample in response to the optical beam 10, is sensed by the detector or sensor of the spectrometer module 160. The spectrometer module 160 consequently generates the spectral data of the sample material as described in further detail herein.

The spectrometer 102 may be configured to begin measurement of a sample material S with just ambient light, without the optical beam 10. After completing the measurement with ambient light only, the illumination module 140 of the spectrometer 102 can generate the optical beam 10, and the spectrometer module 160 can begin measurement of the sample material with the optical beam 10. In this case, there may be a brief time lapse between the initiation of a measurement, for example by a user pressing the operating button 1006, and the generation of the optical beam 10 and the visible portions thereof. The ambient light-only measurement can be used to reduce or eliminate the contribution of ambient light in the spectral data of the sample material S. For example, the measurement made with ambient light only can be subtracted from the measurement made with the optical beam 10.

A portion of the optical beam 10 that is reflected from the sample material S may be visible to the user; this visible, reflected portion of optical beam 10 may define the measurement area 50 of the sample material S. The measurement area 50 of the sample may at least partially overlap with and fall within the field of view 40 of the detector of the spectrometer. The area covered by the field of view 40 may be larger than the visible area of the sample illuminated by the optical beam 10, or the measurement area 50 defined by the visible portion of the optical beam 10. Alternatively, the field of view may be smaller than the optical beam, for example. In many configurations, the field of view 40 of the detector of the spectrometer module is larger than the area illuminated by the optical beam 10, and hence the measurement area 50 is defined by the optical beam 10 rather than by the field of view 40 of the detector.

The visible portion of optical beam 10 may comprise one or more wavelengths corresponding to one or more colors visible to the user. For example, the visible portion of optical beam 10 may comprise one or more wavelengths corresponding to the colors red, orange, yellow, blue, green, indigo, violet, or a combination thereof. The visible portion of optical beam 10 reflected from the sample material S may comprise about 0.1% to about 10%, about 1% to about 4%, or about 2% to about 3% of optical beam 10. The visible portion of optical beam 10 may comprise light operating with power in a range from about 0.1 mW to about 100 mW, about 1 mW to about 75 mW, about 1 mW to about 50 mW, about 5 mW to about 40 mW, about 5 mW to about 30 mW, about 5 mW to about 20 mW, or about 10 mW to about 15 mW. The visible portion of optical beam 10 incident on the sample may have an intensity in a range from about 0.1 mW to about 100 mW, about 1 mW to about 75 mW, about 1 mW to about 50 mW, about 5 mW to about 40 mW, about 5 mW to about 30 mW, about 5 mW to about 20 mW, or about 10 mW to about 15 mW. The visible portion of optical beam 10 incident on the sample may have an intensity or total light output in a range from about 0.001 lumens to about 10 lumens, about 0.001 lumens to about 5 lumens, about 0.005 lumens to about 10 lumens, about 0.01 lumens to about 10 lumens, about 0.005 lumens to about 5 lumens, about 0.05 lumens to about 5 lumens, about 0.1 lumens to about 5 lumens, about 0.2 lumens to about 1 lumens, or about 0.5 lumens to about 5 lumens.

The optical beam 10 incident on the sample S may have an area of about 0.5 to about 2 $cm^2$, or about 1 $cm^2$. Accordingly, the optical beam 10 incident on the sample S may have an irradiance within a range from about 0.1 $mW/cm^2$ to about 100 $mW/cm^2$, about 1 $mW/cm^2$ to about 75 $mW/cm^2$, about 1 $mW/cm^2$ to about 50 $mW/cm^2$, about 5 $mW/cm^2$ to about 40 $mW/cm^2$, about 5 $mW/cm^2$ to about 30 $mW/cm^2$, about 5 $mW/cm^2$ to about 20 $mW/cm^2$, or about 10 $mW/cm^2$ to about 15 $mW/cm^2$. The optical beam 10 incident on the sample S may have an illuminance ($E_v$)

within a range from about 20 lux (lumens/m²) to about 100,000 lux, about 200 lux to about 75,000 lux, about 400 lux to about 50,000 lux, about 2,000 lux to about 25,000 lux, about 2,000 lux to about 15,000 lux, about 4,000 lux to about 15,000 lux, or about 4,000 lux to about 6,000 lux.

The light output of the visible portion of optical beam 10 may vary depending on the type of light source. In some cases, the visible light output of optical beam 10 may vary due to the different luminous efficacies of different types of light source. For example, blue light-emitting diode (LED) may have an efficacy of about 40 lumens/W, a red LED may have an efficacy of about 70 lumens/W, and a green LED may have an efficacy of about 90 lumens/W. Accordingly, the visible light output of optical beam 10 may vary depending on the color or wavelength range of the light source.

The light output of the visible portion of optical beam 10 may also vary due to the nature of interactions between the different components of a light source. For example, the light source may comprise a light source combined with an optical element configured to shift the wavelength of the light produced by the first light source, as described in further detail herein. In this instance, the visible light output of the visible portion of optical beam 10 may vary depending on the amount of the light produced by the light source that is configured to pass through the optical element without being absorbed or wavelength-shifted, as described in further detail herein.

The optical beam 10 may comprise a visible aiming beam 20. The aiming beam 20 may comprise one or more wavelengths corresponding to one or more colors visible to the user, such as red, orange, yellow, blue, green, indigo, or violet. Alternatively or in combination, the optical beam 10 may comprise a measurement beam 30, configured to measure the spectra of the sample material. The measurement beam 30 may be visible, such that the measurement beam 30 comprises and functions as a visible aiming beam. The optical beam 10 may comprise a visible measurement beam 30 that comprises a visible aiming beam. The measurement beam 30 may comprise light in the visible spectrum, non-visible spectrum, or a combination thereof. The aiming beam 20 and the measurement beam 30 may be produced by the same light source or by different light sources within the illumination module 140, and can be arranged to illuminate the sample material S within the field of view 40 of the detector or sensor of the spectrometer 102. The visible aiming beam 20 and the optical beam 30 may be partially or completely overlapping, aligned, and/or coaxial.

The visible aiming beam 20 may comprise light in the visible spectrum, for example in a range from about 390 nm to about 800 nm, which the user can see reflected on a portion of the sample material S. The aiming beam 20 can provide basic visual verification that the spectrometer 102 is operational, and can provide visual indication to the user that a measurement is in progress. The aiming beam 20 can help the user visualize the area of the sample material being measured, and thereby provide guidance the user in adjusting the position and/or angle of the spectrometer 102 to position the measurement area over the desired area of the sample material S. The aiming beam 20 may be configured with circuitry to be emitted throughout the duration of a measurement, and automatically turn off when the measurement of the sample material S is complete; in this case, the aiming beam 20 can also provide visual indication to the user of how long the user should hold the spectrometer 102 pointed at the sample material S.

The visible aiming beam 20 and the measurement beam 30 may be produced by the same light source, wherein the visible aiming beam 20 comprises a portion of the measurement beam 30. Alternatively, the aiming beam 20 may be produced by a first light source, and the measurement beam 30 may be produced by a second light source. For example, the measurement beam 30 may comprise an infrared beam and the aiming beam 20 may comprise a visible light beam.

The measurement beam 30 may be configured to illuminate the measurement area of the sample S, and the aiming beam 20 may be configured to illuminate an area of the sample overlapping with the measurement area, thereby displaying the measurement area to the user. The visible area illuminated by the visible aiming beam 20 may comprise from about 50% to about 150% or about 75% to about 125% of the measurement area, or at least about 90%, at least about 95%, or at least about 99% of the measurement area.

One or more optics of the illumination module, such as a lens or a parabolic reflector, may be arranged to receive the aiming beam 20 and the measurement beam 30 and direct the aiming beam and measurement beam toward the sample material S, with the aiming beam and measurement beam overlapping on the sample. The aiming beam 20 may be arranged to be directed along an aiming beam axis 25, while the measurement beam 30 may be arranged to be directed along a measurement beam axis 35. The aiming beam axis 25 may be co-axial with measurement beam axis 35.

The sensor or detector of the spectrometer module 160 may comprise one or more filters configured to transmit the measurement beam 30 but inhibit transmission of the aiming beam 20. In many configurations, the spectrometer module comprises one filter configured to inhibit transmission of visible light, thereby inhibiting transmission of portions of the aiming beam 20 and measurement beam 30 reflected from the sample that comprise visible light. In some configurations, the spectrometer module 160 may comprise a plurality of optical filters configured to inhibit transmission of a portion of the aiming beam 20 reflected the sample material S, and to transmit a portion of the measurement beam 30 reflected from the sample. In configurations of the spectrometer module comprising a plurality of optical channels, the spectrometer module may comprise a plurality of filters wherein each optical filter corresponds to an optical channel. Each filter may be configured to inhibit transmission of light within a specific range and/or within a specific angle of incidence, wherein the filtered specific range or specific angle of incidence may be specific to the corresponding channel. In some configurations, each optical channel of the spectrometer module may comprise a field of view. The field of view 40 of the spectrometer module may hence comprise a plurality of overlapping fields of view of a plurality of optical channels. The aiming beam and the measurement beam may overlap with the plurality of overlapping fields of view on the sample S. In some configurations, a diffuser may be disposed between the plurality of optical filters and the incident light from the sample, wherein each optical filter corresponds to an optical channel. In such configurations, the plurality of optical channels may comprise similar fields of view, each field of view at least partially overlapping with the fields of view of other optical channels, wherein the spectrometer substantially comprises a field of view of +1-90°.

Optionally, the visible aiming beam 20 may be produced by a light source separate from the illumination module 140. In this case, the separate light source may be configured to produce the aiming beam such that the aiming beam illuminates a portion of the sample material that overlaps with the measurement area of the sample.

Figure 22:
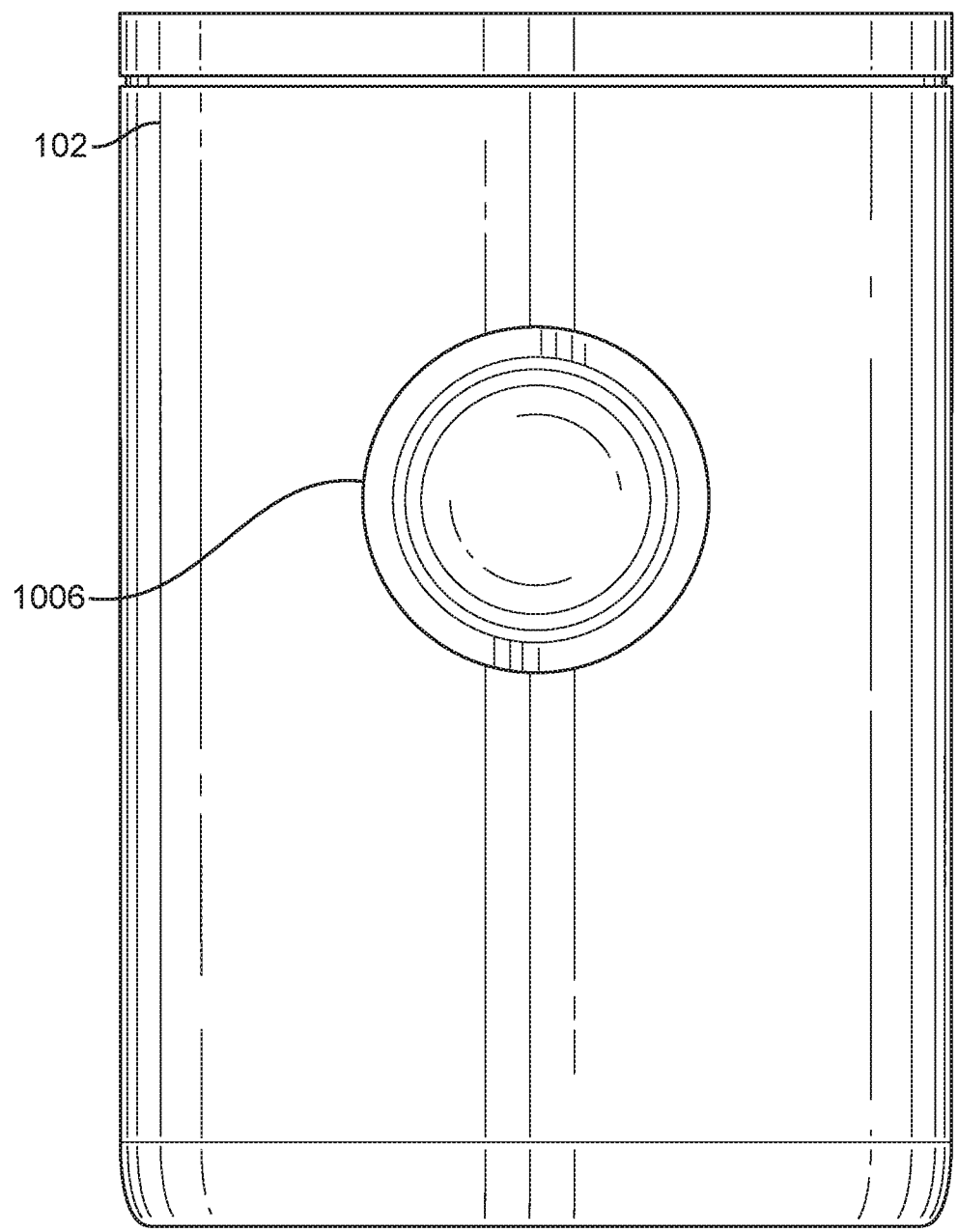
FIG. 22 shows a top view of a spectrometer showing an operation button.

FIG. 22 shows a top view spectrometer 102. The spectrometer can comprise an operating button 1006. An operating button 1006 can allow a user to control battery power to one or more components in the spectrometer. In some cases, a user can power a spectrometer on and off by manipulating the operating button. An operating button can be a compressible button, switch, or touchscreen (e.g. capacitive screen).

Figure 23:
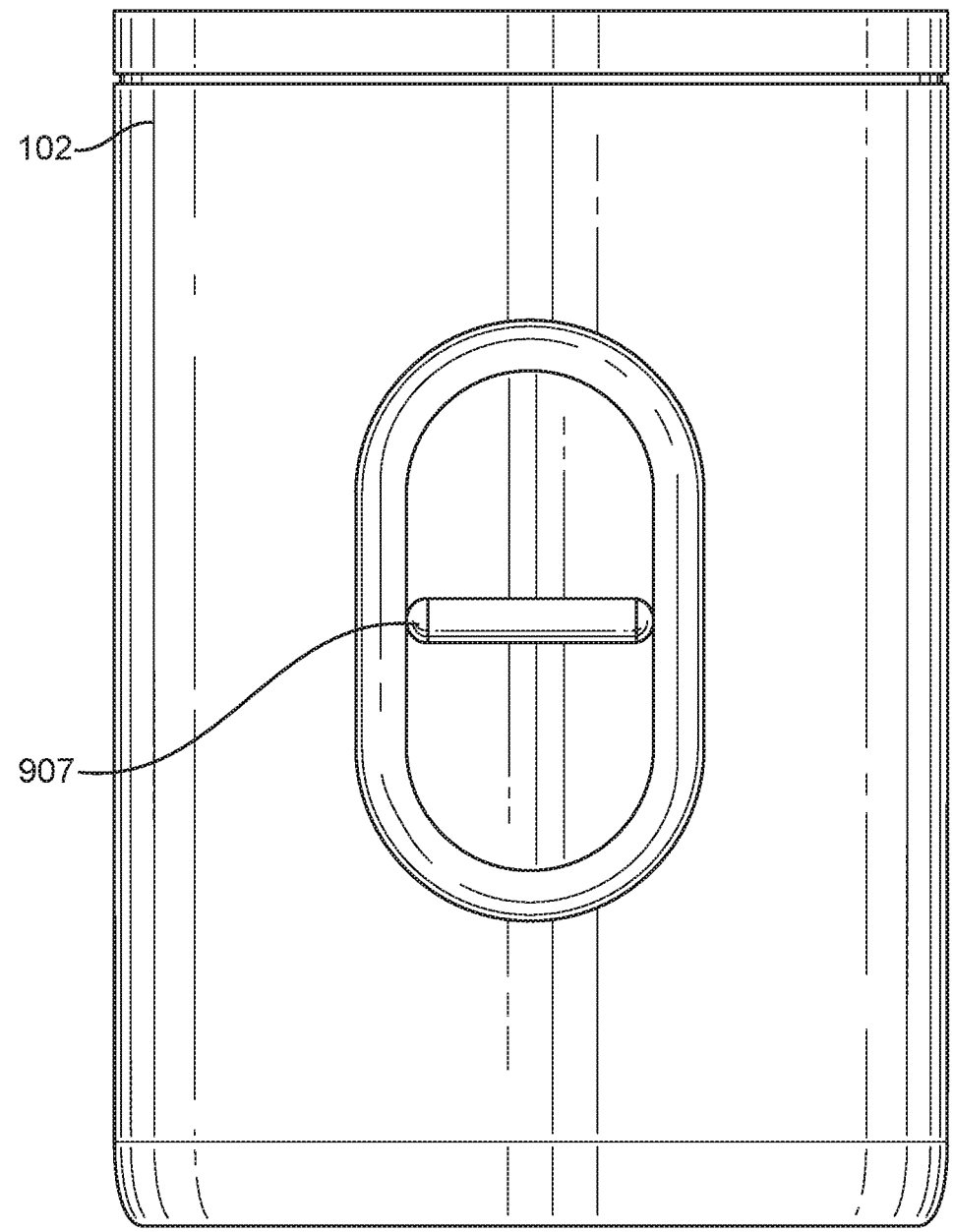
FIG. 23 shows a bottom view of a spectrometer showing a protrusion.

FIG. 23 shows a bottom view of a spectrometer 102 opposed a side of a spectrometer comprising an operating button. The spectrometer can comprise a protrusion 907 on the spectrometer. When the spectrometer is fitted in a cover or sheath the protrusion may be accessed through the one or more openings in the sheath. The protrusion 907 can comprise a raised bump, raised line, a groove, a depression, a textured surface, a nub, and/or a raised structural feature that can be gripped by a user's hand and/or finger. A user may push the spectrometer 100 out of the container when the sheath is placed in the container by pushing and/or pulling on the protrusion 907 to apply a shear force to the spectrometer. In some cases, the protrusion can be recessed in a surface of the spectrometer such that the protrusion does not interfere with the sheath (e.g., container) when the spectrometer is pushed into or pulled out of the container. The protrusion can be on a side of the spectrometer that comprises the button 1006. The protrusion can be on a side of the spectrometer that does not comprise the protrusion. The protrusion can be on a side of the spectrometer opposite the side of the spectrometer that comprises the button.

Figure 24:
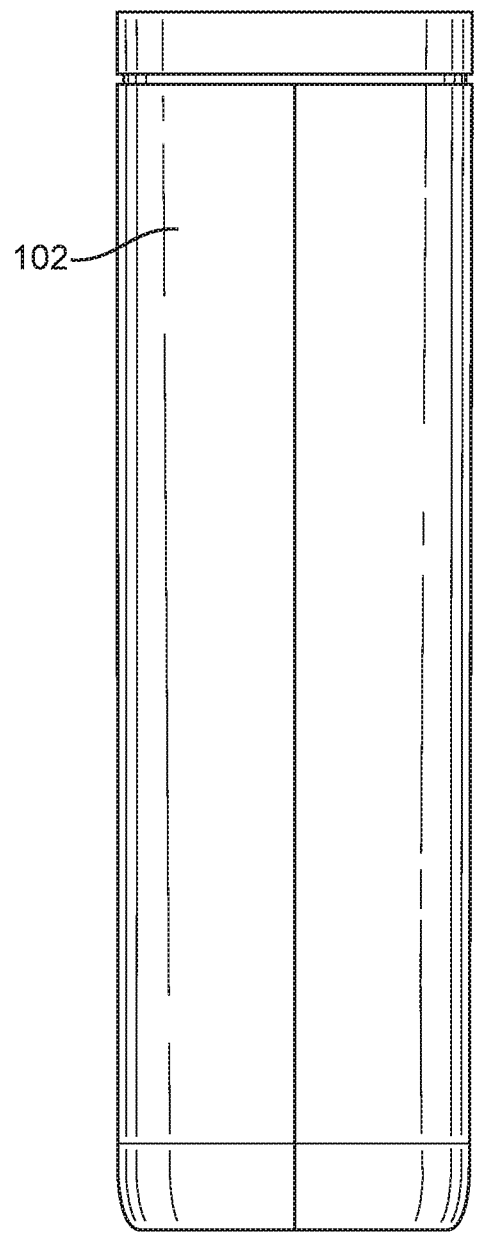
FIG. 24 shows a side view of a spectrometer.

FIG. 24 shows a side view of the spectrometer 102.

Figure 25:
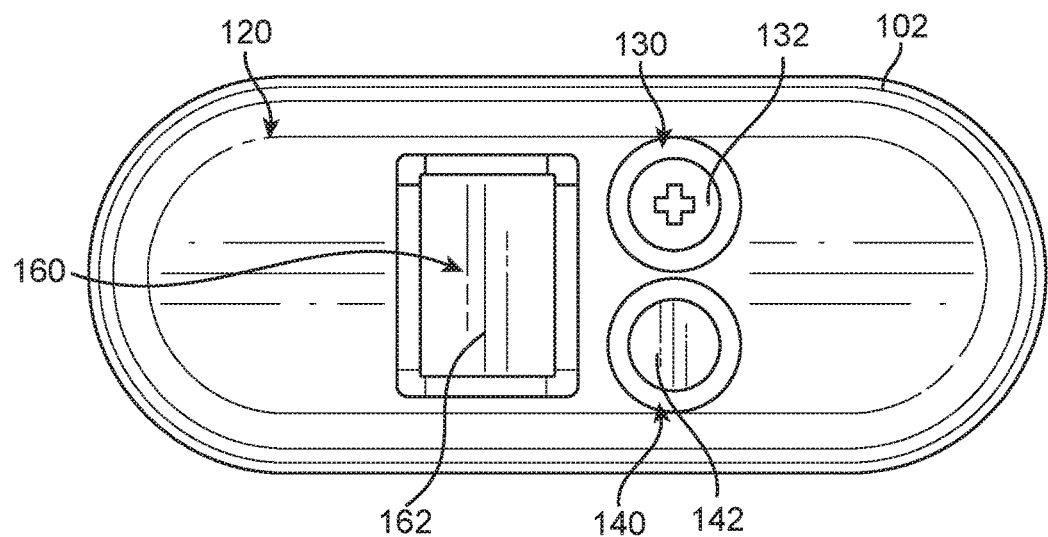
FIG. 25 shows an end view of spectrometer head.

FIG. 25 shows an end view of the spectrometer head 120. The spectrometer head comprises one or more of a spectrometer module 160, a temperature sensor module 130, and an illumination module 140. Each module, when present, can be covered with a module window. For example, the spectrometer module 160 can comprise a spectrometer window 162, the temperature sensor module 130 can comprise a temperature sensor window 132, and the illumination module 140 can comprise an illumination window 142.

Figure 26:
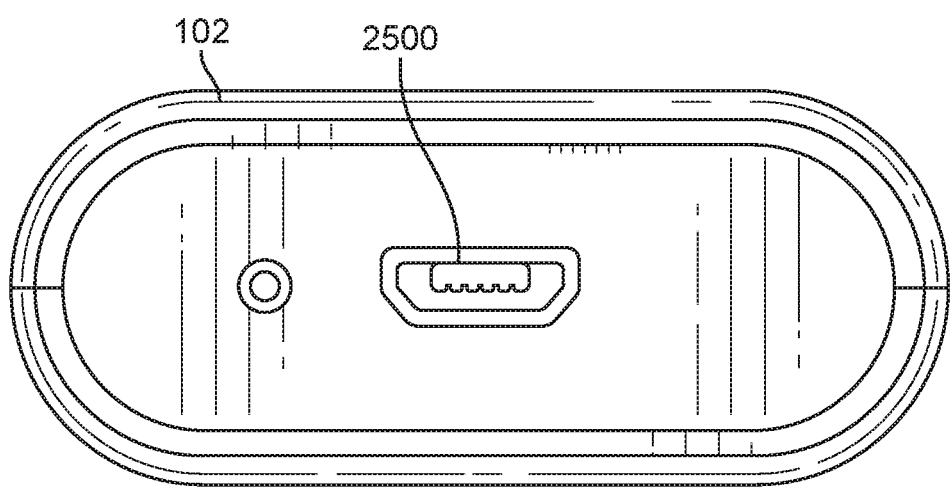
FIG. 26 shows an end of a spectrometer comprising a charging contact.

FIG. 26 shows an end of the spectrometer 102 comprising a charging port 2500. The charging port can provide an electrical connection between an energy storage device (e.g., battery) housed in the spectrometer and an energy source configured to provide energy to the energy storage device. In some cases, the charging port can be a USB charging port. In some cases, the charging port can comprise a pin electrical connection. The electrical connection can be configured to be fitted on a charging cradle. In some cases, the charging port 2500 can be provided on a side of the spectrometer opposite a side of the spectrometer comprising the spectrometer head.

Figure 27:
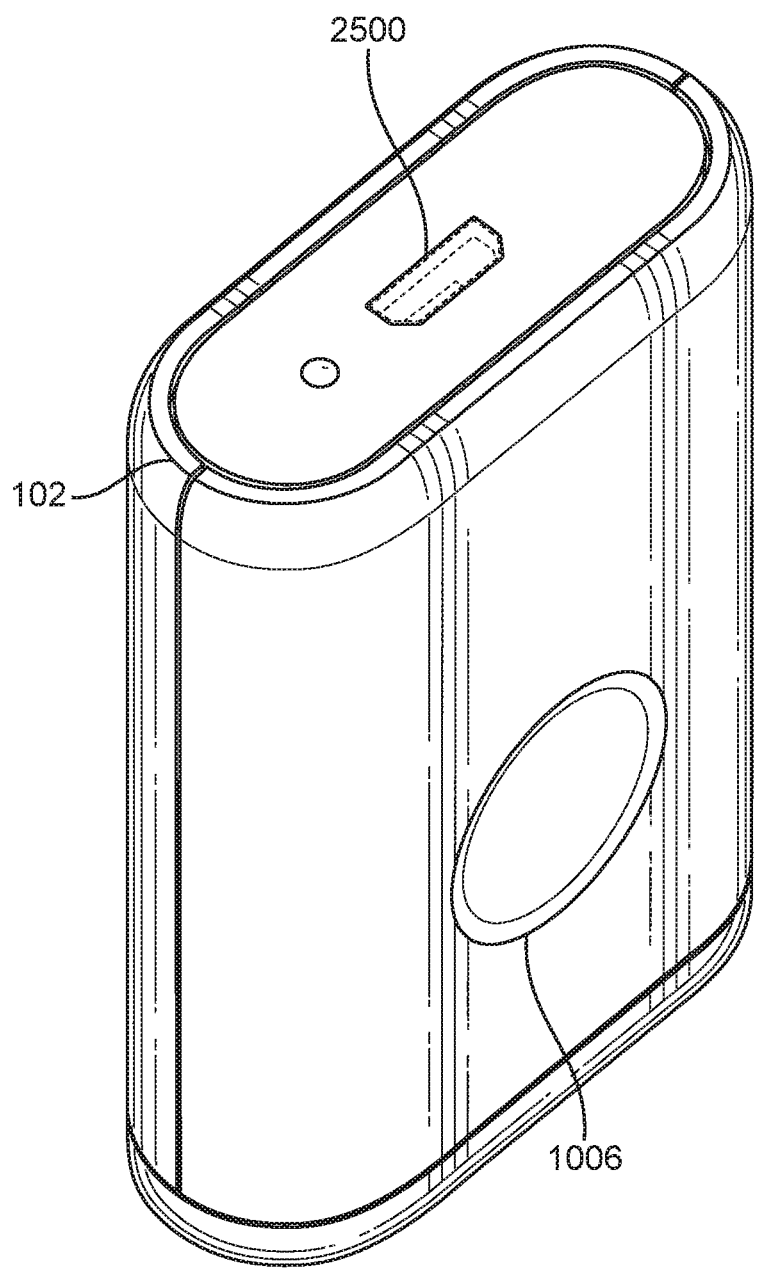
FIG. 27 shows an isometric view of a spectrometer with a side comprising a charge contact facing up.

FIG. 27 shows an isometric view of the spectrometer 102.

Figure 28:
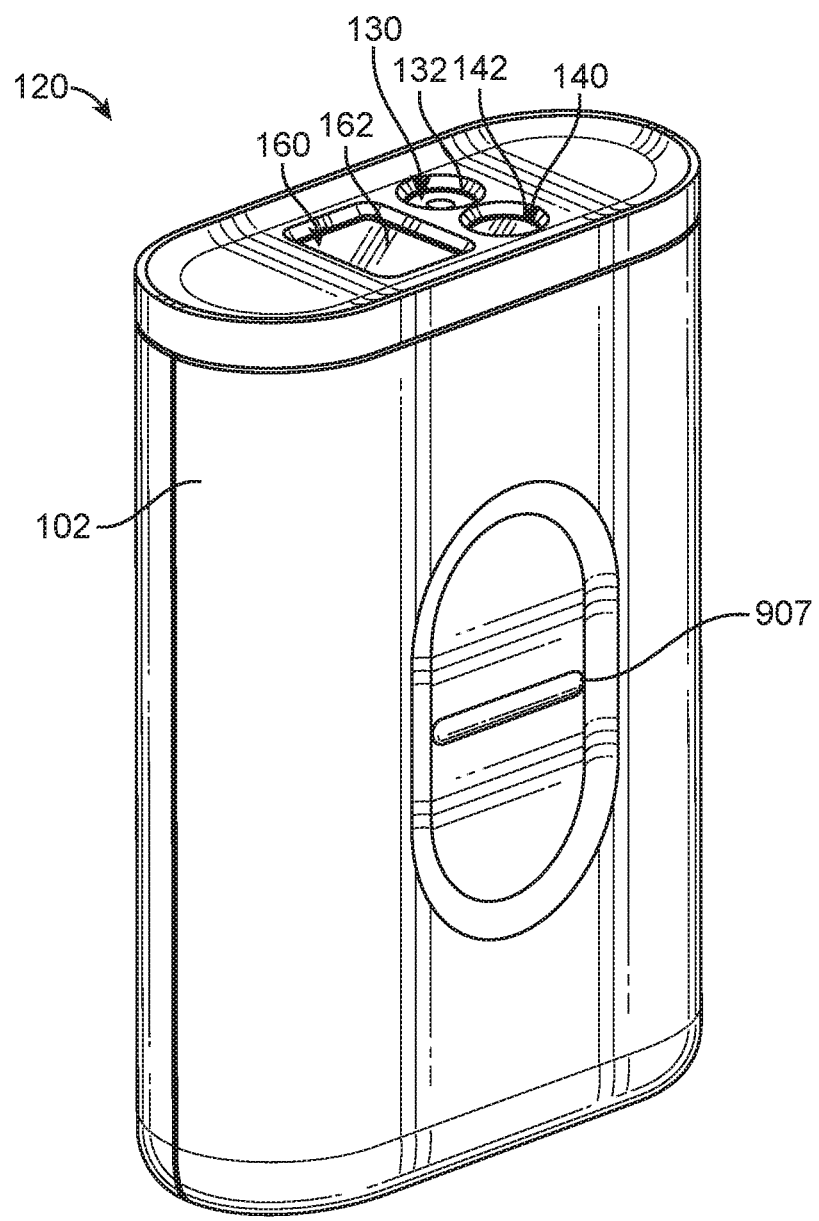
FIG. 28 shows an isometric view of a spectrometer with a side comprising a spectrometer head facing up.

FIG. 28 shows another isometric view of the spectrometer showing the spectrometer head 120 and the protrusion 907.

Figure 29:
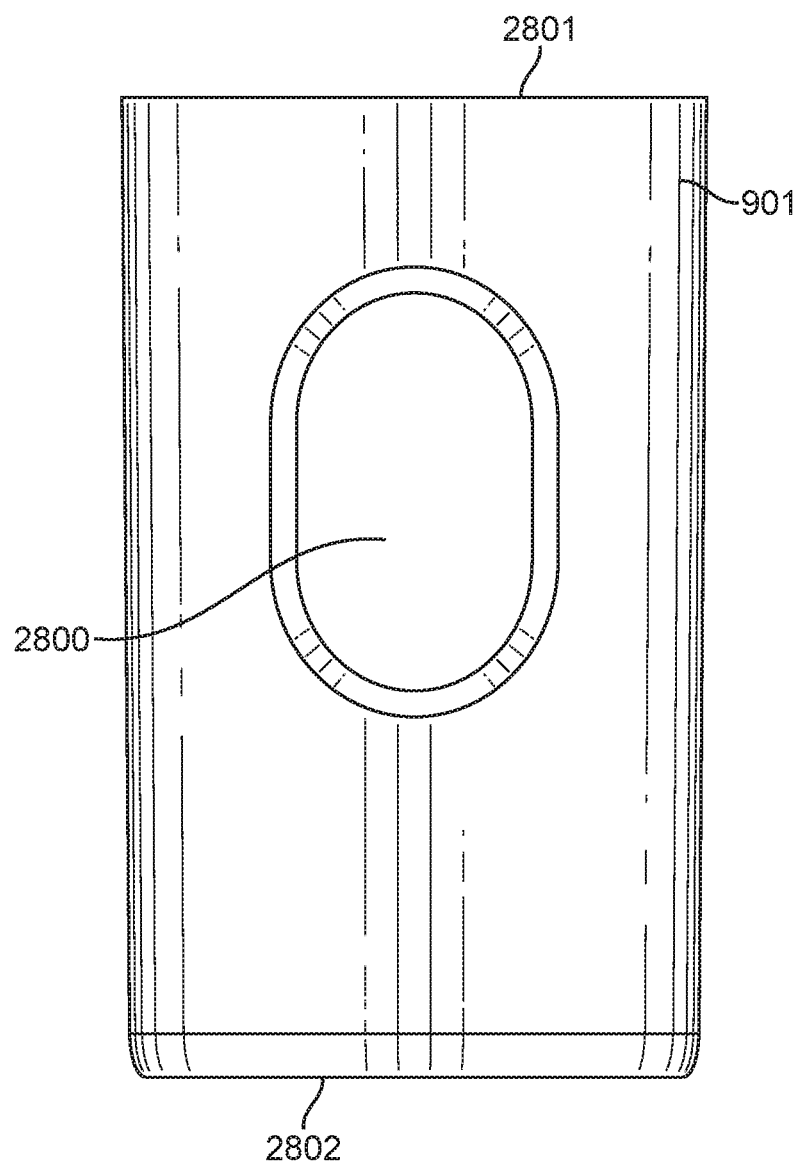
FIG. 29 shows a top view of a cover showing a hole.

FIG. 29 shows a top view of cover 901 configured to house the spectrometer. The spectrometer appears similarly in bottom view and can be symmetrical, for example. The cover can be a protective cover for the spectrometer. The cover can provide a controlled environment for measuring of one or more samples with the spectrometer. The cover can provide a controlled environment for calibration the spectrometer. The cover 901 can comprise one or more holes 2800 through which the spectrometer can be accessed when the spectrometer is fitted in the cover. The button of the spectrometer can be accessed through the hole. The protrusion of the spectrometer can be accessed through the hole. The cover can have an open end 2801 through which the spectrometer can enter and exit the cover. The cover can have a closed end 2802 opposite the open end.

Figure 30:
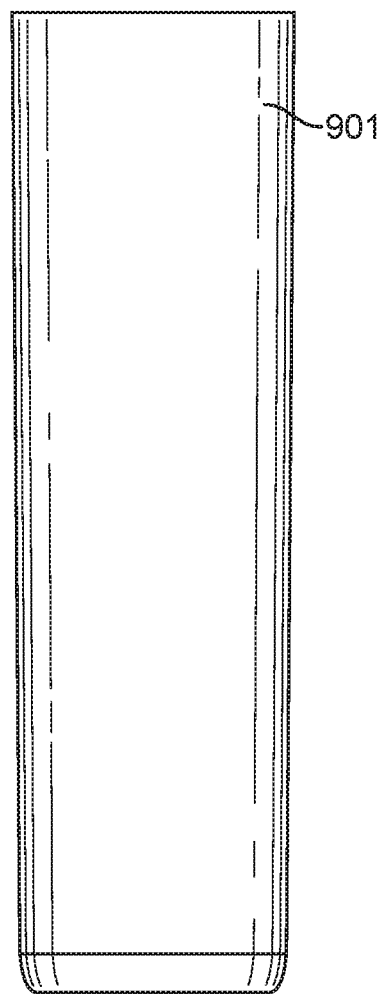
FIG. 30 shows a side view of a cover.

FIG. 30 shows a side view of the cover 901.

Figure 31:
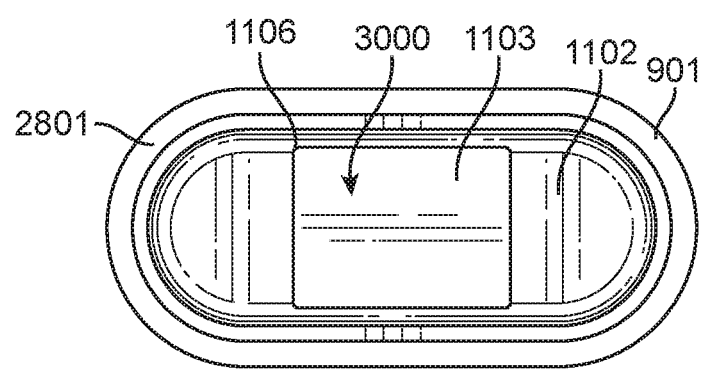
FIG. 31 shows an end view of an open side of a cover.

FIG. 31 shows an end view of the open end 2801 of the cover 901. When looking into the open end the interior surfaces of the cover can be seen. A bottom interior surface (e.g., base) 1102 of the cover can comprise a cavity 3000. The base 1102 can house the reflective material 1103. The reflective material can be adhered to an inner surface of the cover with an adhesive. The base can house the reflective material 1103 in a reflector box 1106 embedded in the base.

Figure 32:
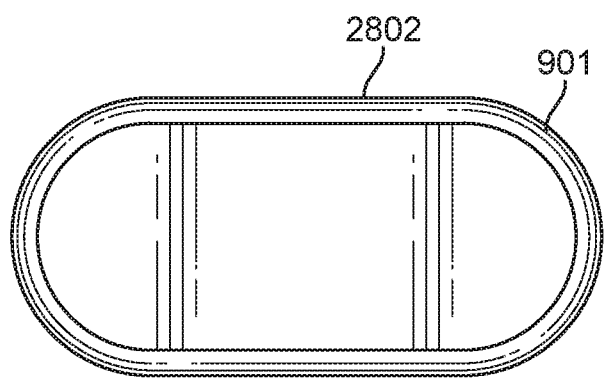
FIG. 32 shows an end view of a closed side of a cover.

FIG. 32 shows an end view of the closed end of the cover 901. The closed end of the cover can comprise a flat surface. The closed end of the cover can comprise a solid surface. The closed end of the cover can comprise a closed surface.

Figure 33:
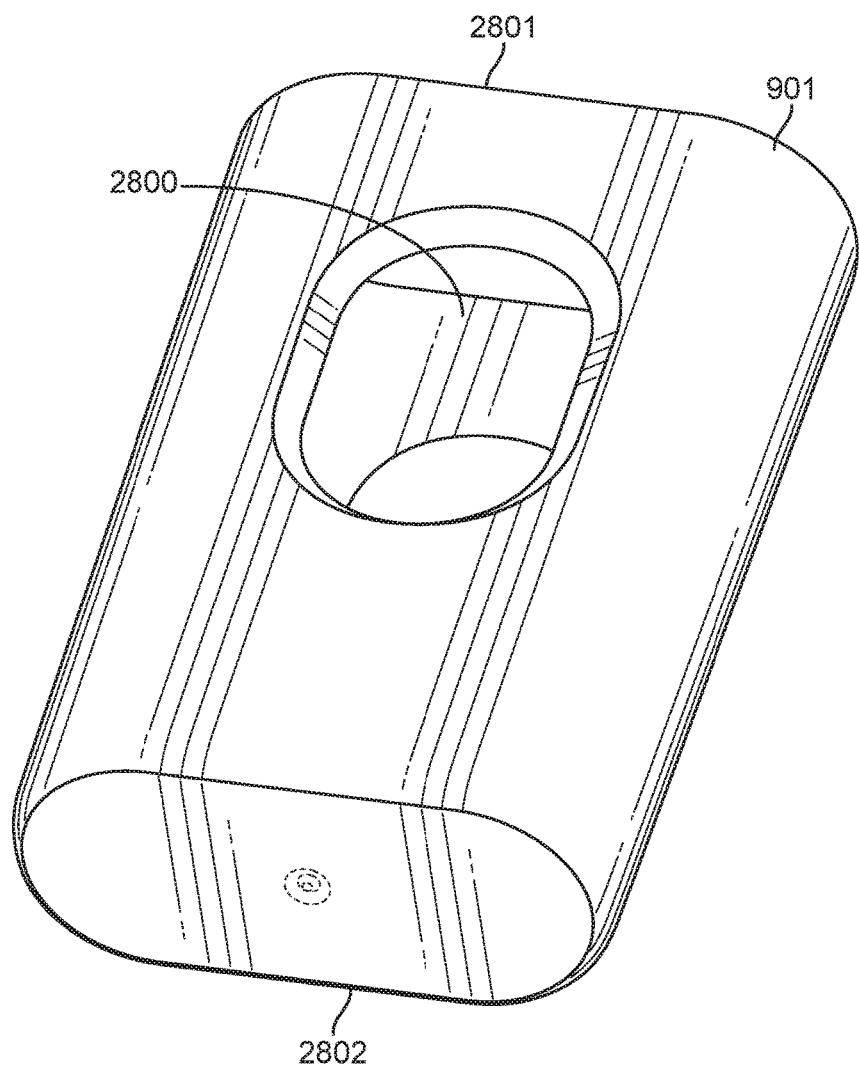
FIG. 33 shows an isometric view of a cover with a closed side of the cover facing a front of the view.

FIG. 33 shows an isometric view of the cover 901.

Figure 34:
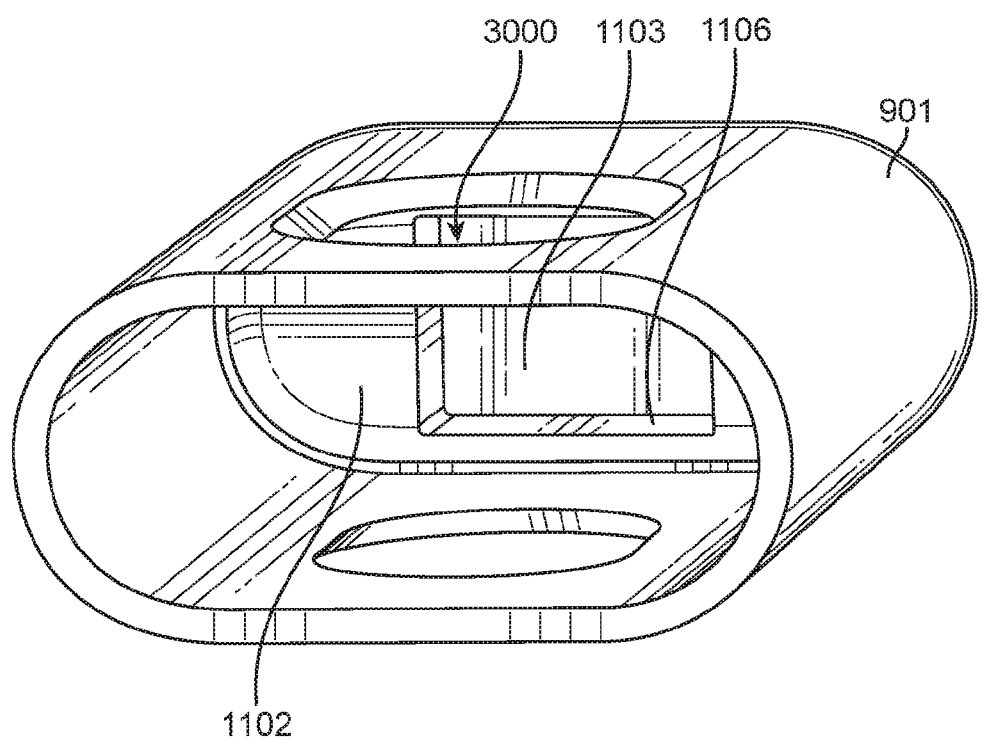
FIG. 34 shows an isometric view of the cover showing a base of the cover.

FIG. 34 shows an isometric view of the cover 901 that shows the interior of the cover including the base 1102.

Figure 35:
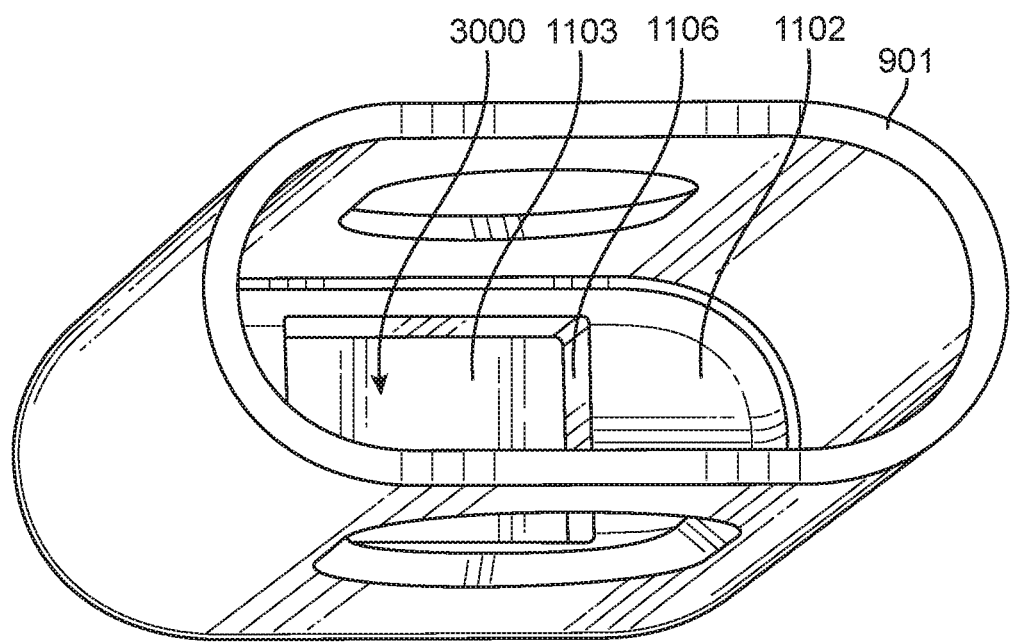
FIG. 35 shows an isometric view of the cover showing a base of the cover with a top right corner of the base visible.

FIG. 35 shows an isometric view of the cover 901 that shows the interior of the cover including the base 1102.

Figure 36B:
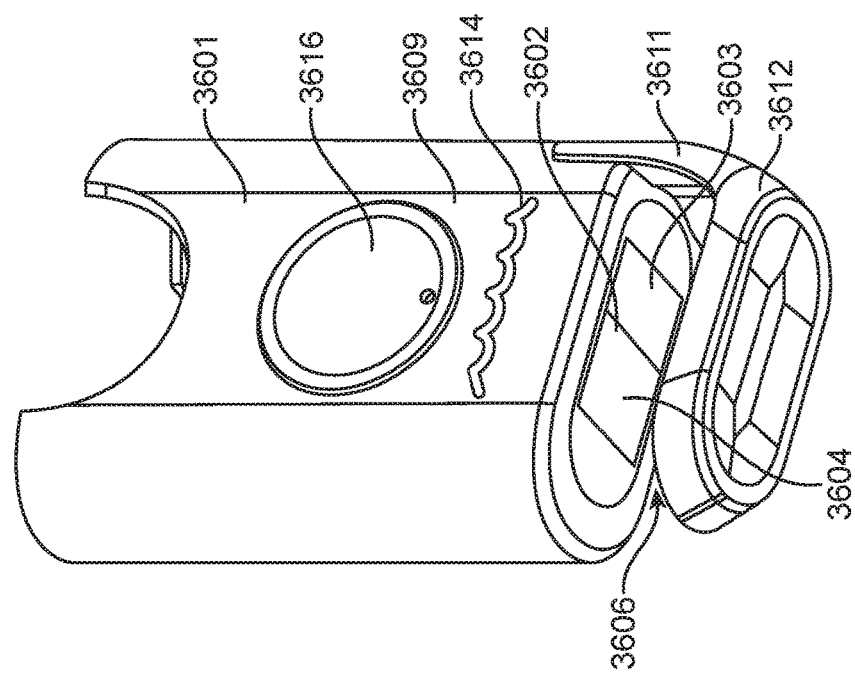
FIGS. 36A and 36B are perspective views of an exemplary accessory configured to facilitate measurement of a liquid sample.
Figure 36A:
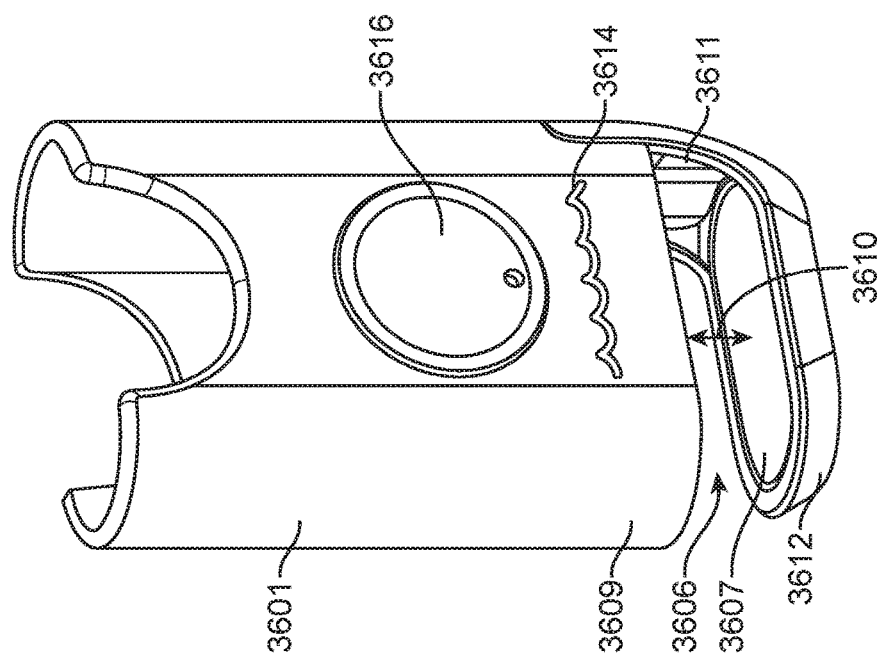

FIGS. 36A and 36B are perspective views of an exemplary liquid measurement accessory 3609 configured to facilitate measurement of a liquid sample. The accessory 3609 comprises a protective cover 3601, wherein the spectrometer may be placed within the protective cover when the accessory is coupled to the spectrometer. As described herein in reference to FIGS. 19A-19B, the protective cover can form a liquid-tight seal or air-tight seal against the spectrometer, such that when the spectrometer is coupled to the accessory, liquid may not be able to permeate a boundary between the spectrometer and the protective cover. For example, the protective cover may comprise a gasket, o-ring, or other mechanical seal, the seal comprising a rubber, Teflon, plastic, or metal material, for example. The protective cover can thus allow the spectrometer, coupled to the accessory and placed within the protective cover, to be dipped in the liquid sample without the liquid directly contacting or damaging the spectrometer.

The accessory 3609 can comprise a window 3602, similar to window 1902 describe in reference to FIGS. 19A-19B. The window 3602 can be configured to permit transmission of light energy from the illumination module of the spectrometer head. In embodiments wherein the window comprises a material different from the protective cover, the window may be configured to form a liquid-tight seal against the material of the protective cover, such that liquid may be prevented from reaching the spectrometer placed within the protective cover. The window 3602 may comprise a first window 3603 and a second window 3604, wherein the first window and the second window may be optically isolated from each other in order to inhibit interference of signals. The first window may be arranged adjacent to the illumination window 142 (as shown in FIG. 3) of the spectrometer when the spectrometer is coupled to the accessory, such that light from the illumination module can be transmitted through the illumination window and the first window to the liquid sample. The second window may be arranged adjacent to the spectrometer window 162 (as shown in FIG. 3) of the spectrometer when the spectrometer is coupled to the accessory, such that light from the liquid sample can be transmitted through the second window and the spectrometer window to the detector of the spectrometer. Many aspects of the window 3602, first window 3603, and second window 3604 may be similar to aspects of the window 1902, first window 1903, second window 1904, or third window 1905 described in reference to FIGS. 19A-19B.

The accessory 3609 can further comprise a platform or base 3612 coupled to the protective cover 3601, wherein the base supports a reflective element 3607. The reflective element 3607 may be similar in many aspects to reflective element 1907 described in reference to FIGS. 19A-19B. For example, the reflective element 3607 may comprise a material that is a diffuse reflector, and may be embedded in the base 3612 with or without a protective layer provided over the reflective element. The base may be coupled to the protective cover with an arm or post 3611 configured to place the reflective element at a predetermined measurement distance 3610 from the window 3602. Alternatively, the base may be coupled to the protective cover with two or more arms or posts. When the spectrometer coupled to the accessory is partially dipped or immersed in a liquid sample for measurement of the sample, the liquid sample can fill a space 3606 between the end of the protective cover 3601 comprising the window 3602 and the reflective element 3607. Illumination from the illumination module can illuminate the volume of the liquid sample filling the space 3606. The reflective element can increase the amount and/or intensity of light reflected back towards the spectrometer, thereby helping to increase the accuracy of measurement. The distance 3610 can be configured to be similar in many aspects to the distance 1910 described in reference to FIGS. 19A-19B.

The protective cover 3601 of the accessory 3609 may further comprise a liquid level indicator 3614. The liquid level indicator may be configured to indicate an ideal liquid height on the protective cover as the handheld spectrometer coupled to the liquid measurement accessory is dipped or immersed in the liquid sample. As a user begins to immerse the spectrometer/liquid accessory assembly into the liquid sample and the liquid level on the protective cover rises, the user may use the liquid level indicator as a visual guide for determining when to stop lowering the spectrometer assembly further down in the liquid sample.

The protective cover 3601 may further comprise a movable portion 3616, configured to allow access to an operation mechanism of the handheld spectrometer (e.g., operating button 1006 shown in FIG. 10) when the handheld spectrometer is placed within the protective cover. The movable portion may be positioned so as to be aligned with the operation mechanism of the spectrometer when the spectrometer is placed within the protective cover. The movable portion may, for example, comprise a soft, flexible material that can deform in response to pressure, to allow operation of the operation mechanism positioned beneath the movable portion. The movable portion is preferably configured to form a liquid-tight seal against the protective cover about the periphery of the movable portion, to prevent liquid from permeating the boundary of the movable portion and thereby prevent liquid from directly contacting the handheld spectrometer.

Figure 37A:
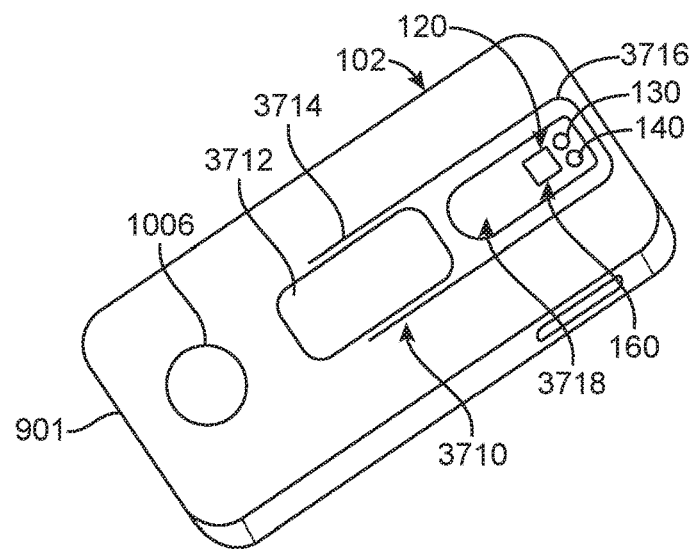
FIG. 37A shows a removable spectrometer cover with a handheld spectrometer as described herein placed in the cover.

FIG. 37A shows a removable spectrometer cover 901 with a handheld spectrometer 102 as described herein placed in the cover. The cover has an opening and an interior sized and shaped to receive and hold the handheld spectrometer 102. The cover 901 comprises an opening 3718 through which the spectrometer can take measurements. The illumination module 140 of the optical head 120 can transmit light through the opening 3718. The sensor module 130 is configured to receive light reflected from the sample as described herein. An operating button 1006 can be used to operate the spectrometer as described herein. The cover comprises a calibration material as described herein.

The cover 901 and the spectrometer 102 are configured to calibrate the spectrometer and measure a sample with the spectrometer coupled to the cover. The cover 901 comprises a movable portion such as a slider 3710 comprising a movable panel 3712 and a guide 3714, for example. The movable portion comprising the panel and guide are arranged to allow the user to slide the panel 3712 over the opening 3718 to place the calibration material 924 as described herein in front of the illumination module and sensor module, such that the calibration material is within the field of view of the spectrometer in order to calibrate the spectrometer as described herein. The cover 901 may comprise a stop 3716 to limit movement of the panel and position the calibration material with a predetermined position and orientation in relation to the spectrometer and illumination module as described herein. The calibration material 924 as described herein is located on an interior surface of the panel, for example. To measure the sample, the user can slide the panel to expose opening 3712, the light source and measurement window of the spectrometer as described herein. The user can aim the spectrometer at the sample and measure spectral data of the sample with the spectrometer calibrated as described herein.

Figure 37B:
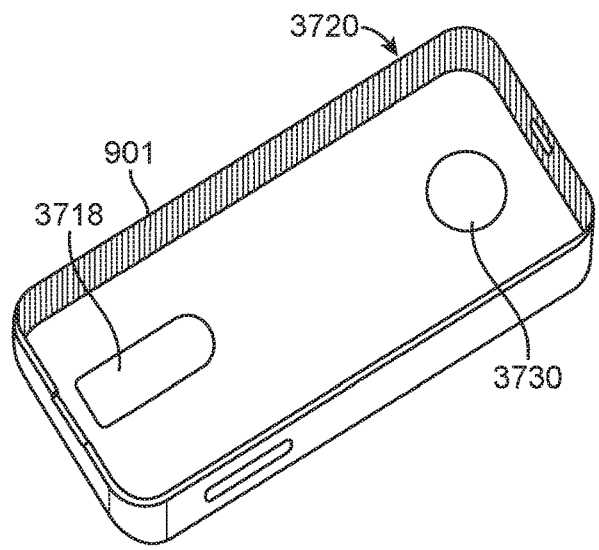
FIG. 37B shows the cover without the spectrometer.

FIG. 37B shows the cover 910 without the spectrometer. The opening 3720 of the cover 910 is sized and shaped to receive the spectrometer. The opening 3718 of the cover 910 is sized and shaped to transmit light from the illumination module 140 of the optical head 120, and to receive light reflected from the sample with the sensor module 130. The cover 901 may comprise an opening 3730 through which the user can access a spectrometer control such as operating button 1006.

Figure 37C:
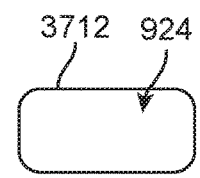
FIG. 37C shows a panel comprising a calibration material as described herein.

FIG. 37C shows the panel 3712 comprising the calibration material 924 as described herein. The calibration material 924 can be located on an interior surface of the panel, for example.

The accuracy of measurements by a spectrometer as described herein may be affected by various elements of the spectrometer, such as the illumination source, light guiding elements, reflective elements, or detecting elements, or by various accessories of the spectrometer used for sample measurement. Even relatively small differences between spectrometer systems can be important, particularly when spectral data generated by a plurality of similar spectrometer systems are compared. To reduce the variations in measured sample spectra due to differences in various spectrometer system components, each spectrometer and/or each accessory of the spectrometer may be calibrated during production of the devices. Also, each spectrometer and/or each accessory as described herein may be assigned a unique identifier at the production site. The unique identifier of a spectrometer and/or each accessory may be stored in a remote database, such as the cloud, and the spectrometer identifier (ID) may be associated with the identifiers of one or more accessories. The calibration spectra of each device may be digitally associated with the unique identifier of the device and stored in a database, such as a database stored on a computing device configured to analyze sample measurement data, for example a remote database. When a user measures a sample material, the user may also take one or more calibration measurements of one or more accessories of the spectrometer system. The calibration data for each accessory and the unique identifier of the accessory may be transmitted to a remoted processing unit along with the sample measurement data and the unique identifier of the spectrometer. The processing unit may then generate the sample spectra in response to the sample measurement data, the unique identifier of the spectrometer, the calibration data, and the unique identifier of the accessory. Such a calibration process can account for variations among spectrometer system components, thus generating more accurate and consistent sample spectra.

According to some embodiments of the invention, for example during production, the spectrometer ID, cover ID, and accessory ID related to the same spectrometer are stored the remote database as described herein, for example the cloud. The spectrometer ID may be associated with and point to the cover and/or the accessory ID.

In operation, for example as part of the calibration process, the related cover and accessory ID are identified based on the spectrometer ID (which points to the cover and accessory ID).

Figure 38:
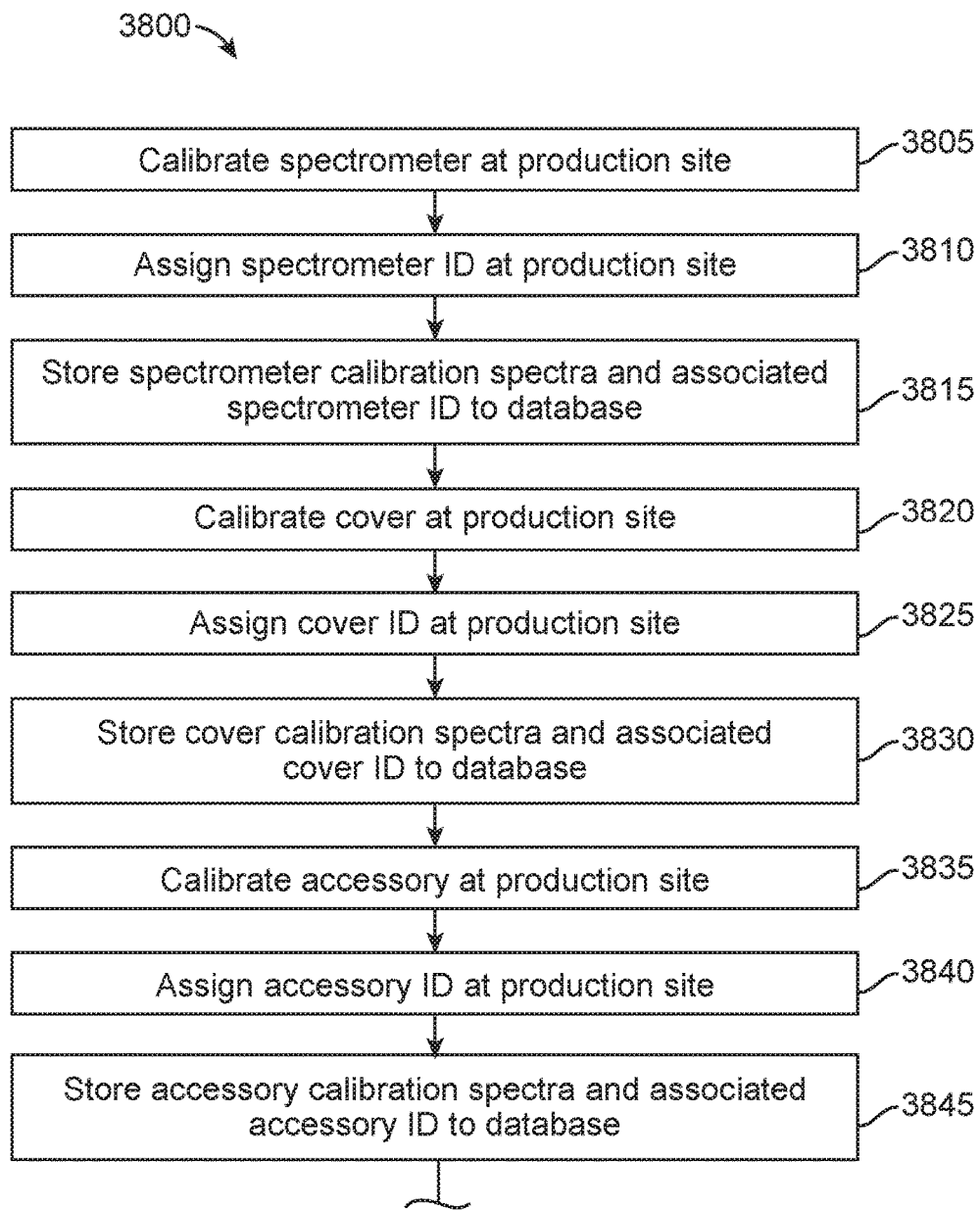
FIG. 38 shows a method for a calibration procedure to improve the accuracy of sample measurements taken with a spectrometer system as described herein.
Figure 38:
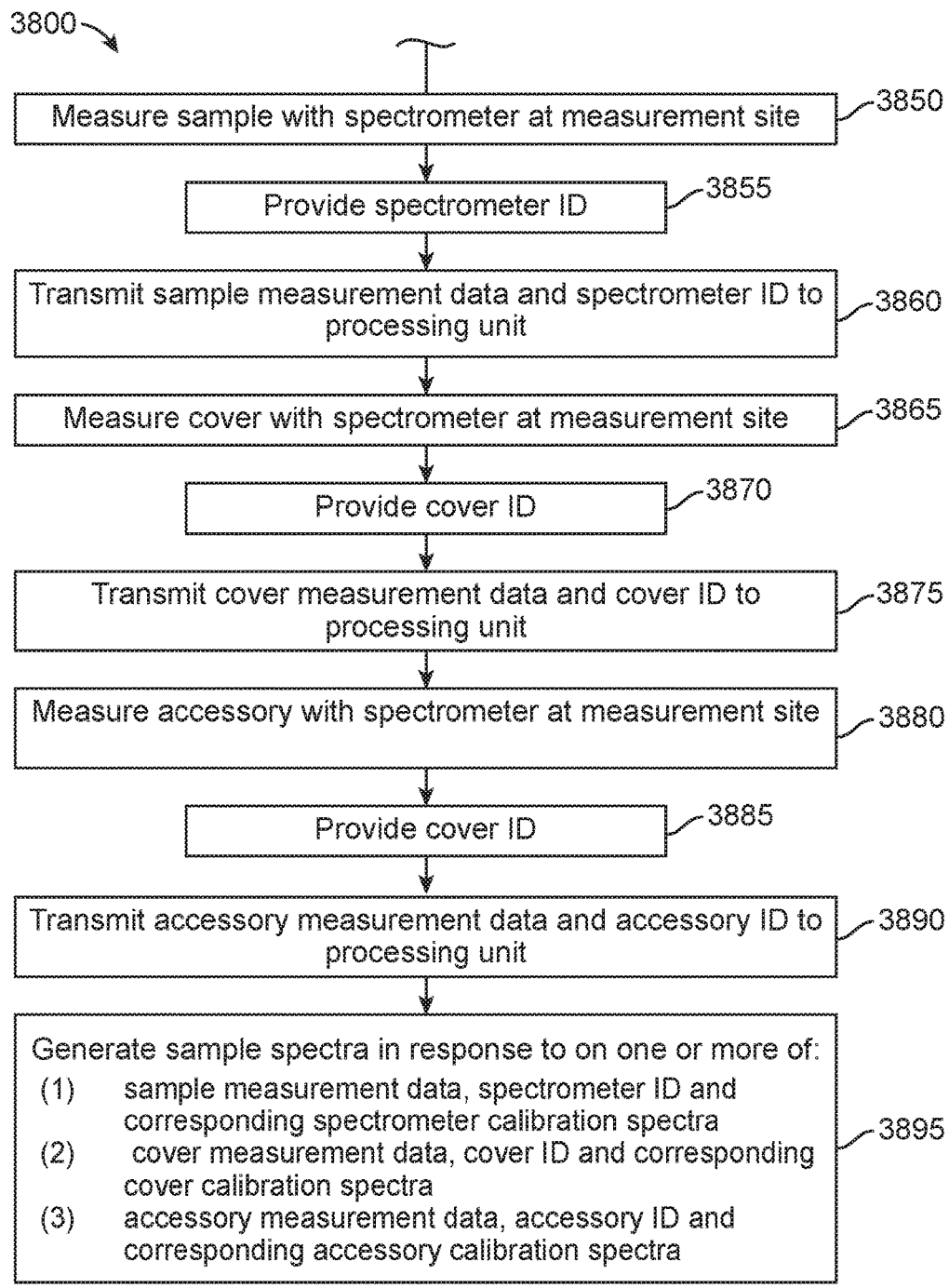

FIG. 38 shows a method 3800 for a calibration procedure to improve the accuracy of sample measurements taken with a spectrometer system as described herein. As described herein, the spectrometer may be removably coupled to a cover (e.g., cover of FIGS. 9A-9B and 11), wherein the spectrometer may be placed within the cover in a calibration orientation (as shown in FIG. 9D). Alternatively or in combination, the spectrometer may be removably coupled to an accessory (e.g., sample container of FIGS. 9A-9B, 13-18B; liquid measurement accessory of FIGS. 19A-19B, 36A-36B). Each cover or accessory may comprise a unique identifier and an associated reference or calibration material (e.g., calibration/reference material 924 of FIG. 9D, reflective material 1103 of FIG. 11, reflective foil 1709 of FIG. 17, reflective element 1907 of FIG. 19A, etc.), and the spectrometer may measure the spectral response of the calibration material while coupled to the accessory, or disposed within the cover in the calibration orientation. Due to variations in materials and manufacturing processes, each cover or accessory produced may generate a slightly different calibration spectral response. Further, one or more elements of a given spectrometer, such as the illumination source, light guiding elements, reflective elements, or detecting elements, may generate slightly different responses at different measurement time points. Method 3800 may comprise the steps as follows to account for this variability in the spectral response of different spectrometers, covers, or accessories, thereby improving the accuracy of the sample spectra generated by the spectrometer system.

In step 3805, a handheld spectrometer may be calibrated at a production site. For example, one or more reference materials with known spectral responses, referred to herein as the "golden" reference, may be measured at one or more given wavelengths with the handheld spectrometer to generate spectrometer calibration spectra.

In step 3810, a spectrometer identifier (ID) may be assigned to the handheld spectrometer at the production site. The spectrometer ID may comprise a unique identifier such as an alphanumeric serial code, a barcode, a Quick Response (QR) code, a 2D code, magnetic code, or any other type of unique identifier. The spectrometer ID may be physically displayed on the spectrometer (e.g., printed, engraved, embossed, debossed, labeled, etc. on the housing or body of the spectrometer), and/or may be integrated into the spectrometer (e.g., magnetically embedded in the housing or body of the spectrometer, electronically embedded in a processing unit of the spectrometer, etc.).

The unique identifier may comprise a machine readable identifier, and the spectrometer can be configured to read the unique identifier. For example, the unique identifier may comprise an optical identifier such as a bar code or QR code, and the spectrometer may comprise a camera configured to read the code. Alternatively or in combination, a smartphone can be used to read the optical code and associate the unique identifier with the spectrometer.

In step 3815, the spectrometer calibration spectra of a given handheld spectrometer and the unique spectrometer ID of said handheld spectrometer may be stored to a database. The spectrometer calibration spectra may be digitally coupled to the corresponding spectrometer ID, such that each spectrometer calibration spectrum and corresponding spectral data file stored in the database is associated with the unique spectrometer ID. The database may be stored in a local or remote processing unit configured to perform analysis of spectral data produced by the handheld spectrometer. For example, as described herein in reference to FIG. 2, a spectrometer 102 and/or a handheld computing device 110 may be in wireless communication 116 with a cloud-based storage system or server 118, and the cover spectral response may be stored in a database stored on the server 118. Alternatively or in combination, the database may be stored on a processor 106 of the spectrometer 102 or on a processor of the handheld computing device 110.

In step 3820, a cover of a handheld spectrometer may be calibrated at a production site. For example, a reference material provided with the cover may be measured with a reference spectrometer to generate the cover spectrum. A "golden" calibration reference may be measured with the same reference spectrometer just before or after generating the cover spectrum, wherein the "golden" calibration reference is located at the production site. The cover spectrum may then be divided by the "golden" reference spectrum to generate the cover calibration spectra.

In step 3825, a cover ID may be assigned to cover at the production site. The cover ID may comprise any unique identifier as described in reference to the spectrometer ID. The cover ID may be physically displayed on the cover (e.g., printed, engraved, embossed, debossed, labeled, etc.), and/or may be integrated into the cover (e.g., magnetically embedded, electronically embedded, etc.). The cover ID may comprise the same or a different type of unique identifier as the spectrometer ID.

In step 3830, the cover calibration spectra of a given cover and the cover ID of said cover may be stored to a database, which may be the same database as described in reference to step 3815, or a similar database. The cover calibration spectra may be digitally coupled to the corresponding cover ID, such that each cover calibration spectrum and corresponding spectral data file stored in the database is associated with the unique cover ID. The cover ID may also be digitally coupled to the spectrometer ID of the spectrometer associated with the cover, such that the spectrometer ID of a spectrometer can point to the associated cover ID and calibration spectra of the cover corresponding to the cover ID.

In step 3835, an accessory of a handheld spectrometer may be calibrated at a production site. For example, a reference material provided with the accessory may be measured with a reference spectrometer to generate the accessory spectrum. A "golden" calibration reference may be measured with the same reference spectrometer just before or after generating the accessory spectrum, wherein the "golden" calibration reference is located at the production site. The cover accessory spectrum may then be divided by the "golden" reference spectrum to generate the accessory calibration spectra.

In step 3840, an accessory ID may be assigned to accessory at the production site. The accessory ID may comprise any unique identifier as described in reference to the spectrometer ID. The accessory ID may be physically displayed on the cover (e.g., printed, engraved, embossed, debossed, labeled, etc.), and/or may be integrated into the cover (e.g., magnetically embedded, electronically embedded, etc.). The accessory ID may comprise the same or a different type of unique identifier as the spectrometer ID or the cover ID.

In step 3845, the accessory calibration spectra of a given accessory and the accessory ID of said accessory may be stored to a database, which may be the same database as described in reference to step 3815, or a similar database. The accessory calibration spectra may be digitally coupled to the corresponding accessory ID, such that each accessory calibration spectrum and corresponding spectral data file stored in the database is associated with the unique accessory ID. The accessory ID may also be digitally coupled to the spectrometer ID of the spectrometer associated with the accessory, such that the spectrometer ID of a spectrometer can point to the associated accessory ID and calibration spectra of the accessory corresponding to the accessory ID.

In step 3850, a sample may be measured with the handheld spectrometer at a measurement site to generate sample measurement data. For example, the spectrometer may be placed in a cover in the measurement orientation and used to measure a sample surface, the spectrometer may be coupled to a sample container and used to measure a sample received within the sample container, or the spectrometer may be coupled to a liquid measurement accessory and used to measure a liquid sample while partially immersed in the liquid sample.

In step 3855, the spectrometer ID of the handheld spectrometer used in step 3850 may be provided to a local processing unit in communication with the handheld spectrometer. For example, the spectrometer ID may be embedded in a chip in or on the spectrometer, and read through electrical contacts (e.g., I²C or SPI communication) or through wireless communication systems (e.g., near-field communication, radio frequency identification, Bluetooth, WiFi, etc.). Alternatively or in combination, the user may provide the spectrometer ID to the local processing unit, for example by manually entering the ID comprising a serial number, scanning a barcode or QR code with an optical scanner, etc.

In step 3860, the sample measurement data generated in step 3850 and the spectrometer ID obtained in step 3855 may be transmitted to a processing unit configured to generate the sample spectra. The processing unit may comprise a local or a remote processing unit, and data may be transmitted to said processing unit via a wired or wireless connection.

In step 3865, a reference material of a cover may be measured with the handheld spectrometer at a measurement site to generate cover measurement data. For example, the spectrometer may be placed in the cover in the calibration orientation, and used to measure the calibration material provided near the closed end of the cover as described herein. In many instances, this calibration measurement is made shortly before or after the sample measurement, in order to ensure temporal proximity of the calibration measurement to the sample measurement and thereby account for variations of the spectrometer system over time.

In step 3870, the cover ID of the cover measured in step 3865 may be provided to a local processing unit in communication with the handheld spectrometer, in any of the ways described in reference to step 3855 for providing the spectrometer ID.

In step 3875, the cover measurement data generated in step 3865 and the cover ID obtained in step 3870 may be transmitted to a processing unit configured to generate the sample spectra, as described in reference to step 3860.

In embodiments wherein the spectrometer ID is digitally coupled to the corresponding cover ID along with the cover calibration spectra at a remote database, step 3870 may be omitted. In step 3875, the spectrometer ID, instead of the cover ID, may be transmitted to the processing unit along with the cover measurement data. The processing unit can then identify the cover ID associated with the transmitted spectrometer ID, and access the cover calibration spectra associated with said cover ID. In this way, the spectrometer ID can automatically identify the corresponding cover ID and cover calibration spectra, without the need for the user to provide the cover ID to the local processing unit.

In step 3880, a reference material of an accessory may be measured with the handheld spectrometer at a measurement site to generate accessory measurement data. For example, the spectrometer may be coupled to a sample container or a liquid measurement accessory as described herein, and the spectrometer may be used to measure a reference material provided in or on the accessory. In many instances, this calibration measurement is made shortly before or after the sample measurement, in order to ensure temporal proximity of the calibration measurement to the sample measurement and thereby account for variations of the spectrometer system over time.

In step 3885, the accessory ID of the accessory measured in step 3880 may be provided to a local processing unit in communication with the handheld spectrometer, in any of the ways described in reference to step 3855 for providing the spectrometer ID.

In step 3890, the accessory measurement data generated in step 3880 and the accessory ID obtained in step 3885 may be transmitted to a processing unit configured to generate the sample spectra, as described in reference to step 3860.

In embodiments wherein the spectrometer ID is digitally coupled to the corresponding accessory ID along with the accessory calibration spectra at a remote database, step 3885 may be omitted. In step 3890, the spectrometer ID, instead of the accessory ID, may be transmitted to the processing unit along with the accessory measurement data. The processing unit can then identify the accessory ID associated with the transmitted spectrometer ID, and access the accessory calibration spectra associated with said accessory ID. In this way, the spectrometer ID can automatically identify the corresponding accessory ID and accessory calibration spectra, without the need for the user to provide the accessory ID to the local processing unit.

In step 3895, the processing unit may generate the sample spectra in response to one or more of: (1) the sample measurement data, spectrometer ID, and the corresponding spectrometer calibration spectra stored on the database; (2) the cover measurement data, cover ID, and the corresponding cover calibration spectra stored on the database; and (3) the accessory measurement data, the accessory ID, and the corresponding accessory calibration spectra stored on the database. For example, the corrected sample spectra $R(\lambda)$ may be obtained as follows:

$$R(\lambda) = \frac{S(\lambda)}{C_i(\lambda)} \cdot \frac{C_i(\lambda)}{G(\lambda)} = \frac{S(\lambda)}{G(\lambda)}$$

wherein $S(\lambda)$ is the sample spectrum, $C_i(\lambda)$ is the calibration element spectrum, and $G(\lambda)$ is the "golden" reference spectrum, and wherein $$\frac{S(\lambda)}{C_i(\lambda)}$$

may comprise the sample measurement data divided by the cover or accessory measurement data, and wherein $$\frac{C_i(\lambda)}{G(\lambda)}$$

may comprise the cover or accessory calibration spectra. Note that the first $C_i(\lambda)$ and the second $C_i(\lambda)$ in the above equation for obtaining the corrected sample spectra $R(\lambda)$ are not always identical, since they are measured at a different time on different devices, and thus the equation is approximately correct. The first $C_i(\lambda)$ (i.e. $C_i(\lambda)$ user) is the calibration element spectrum measured for example by the user as he measures a substance, while the second $C_i(\lambda)$ (i.e. $C_i(\lambda)$) is the calibration element spectrum measured at the lab during the production process. So typically $$\frac{S(\lambda)}{G(\lambda)}$$

should be multiplied by a calibration element spectrum constant. The spectrum of the sample $S(\lambda)$ is thus normalized by the spectrum of the calibration element $C_i(\lambda)$ to reduce or substantially eliminate any spectral effects of the sampling system, and the temporal proximity is important to account for any variations of the system over time. In this manner, the variance between the calibration elements is substantially eliminated or reduced, and the sample measurement is effectively calibrated against the highly defined "golden" calibration reference. Generation of the sample spectra can thus take into account the spectral response of the specific cover or accessory used to calibrate the spectrometer and the spectral response of the spectrometer system at the time of measurement of the sample, thereby compensating for the variation among the spectral response of different spectrometer system components and improving the accuracy and reliability of the generated sample spectra.

If more than one "golden" calibration reference is required at the production site, a plurality of "golden" calibration references comprising high grade materials with high grade precision known to those of ordinary skill in the art may be used, such that the different "golden" references yield substantially similar spectra.

A processor can be configured with instructions to perform one or more of the steps of method 3800.

The steps of method 3800 are provided as an example of improving the accuracy of sample measurements by a spectrometer using a calibration procedure. A person of ordinary skill in the art will recognize many variations and modifications of method 3800 based on the disclosure provided herein. For example, some steps may be added or removed. Some of the steps may comprise sub-steps. Many of the steps may be repeated as many times as appropriate or necessary. One or more steps may be performed in a different order than as illustrated in FIG. 38.

Figure 39:
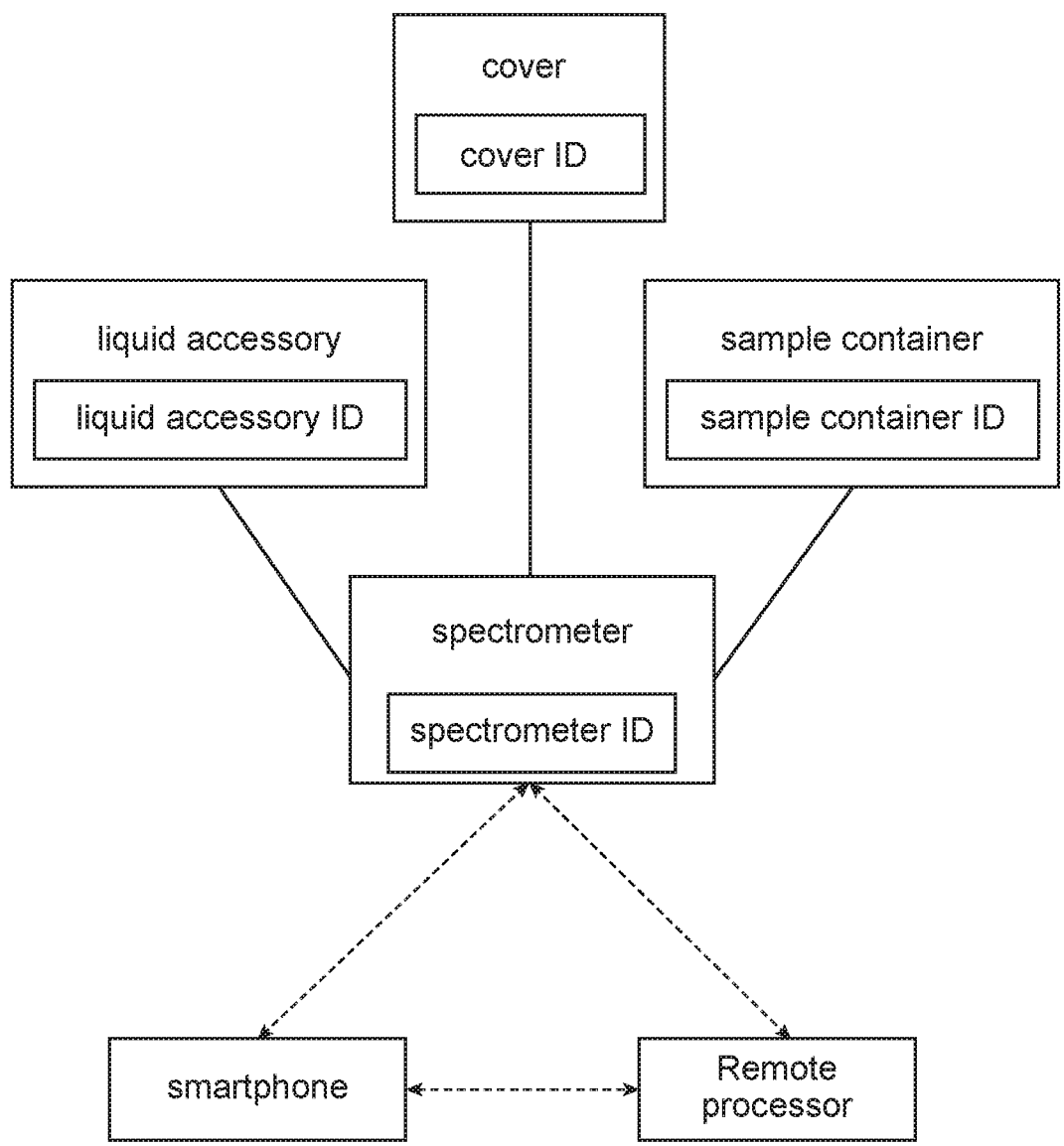
FIG. 39 shows unique identifiers and components of the spectrometer system as described herein.

FIG. 39 shows unique identifiers and components of the spectrometer system as described herein. Each of the cover, the liquid accessory, the sample container, the spectrometer and the smartphone may comprise a unique identifier. The spectrometer can be coupled to each of the liquid accessory, the cover and the sample container for measurements as described herein. The spectrometer can transmit data to the processor directly, such as with an internet connection or indirectly via the smartphone, for example with a double hop wireless configuration with a first wireless hop from the spectrometer to the smartphone and a second wireless hop from the smart phone to the remote processor.

The IDs of the cover, the liquid accessory and the sample container can be read in many ways as described herein, for example by measuring a QR code with the smartphone. The spectrometer ID can be stored in a memory of a processor on the spectrometer. Alternatively, the smart phone could read a code from the spectrometer. Although the spectrometer and phone are shown separately, the two can be combined with the spectrometer integrated with the smartphone in a single handheld unit. The unique IDs are associated with spectral data measured by the spectrometer and transmitted to the remote processor and processed as described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus to measure a spectrum of a plurality of objects, the apparatus comprising:
   a processor configured with instructions to,
      receive a unique identification code for each of a plurality of calibration covers associated with a plurality of spectrometers, wherein said unique identification code for each of the plurality of calibration covers is independent of the respective spectrometer associated with the respective calibration cover;
      receive spectral data from each of the plurality of spectrometers, and
      determine the plurality of objects in response to the spectral data and the plurality of unique identification codes for said each of the plurality of calibration covers.

2. An apparatus as in claim 1, wherein the processor is configured with instructions to receive a unique identification code for each of the plurality of spectrometers and determine the plurality of objects in response to the plurality of unique identification codes for each of the plurality of calibration covers and the unique identification code for each of the plurality of spectrometers.

3. An apparatus as in claim 1, wherein the processor comprises a remote processor configured to receive one or more of sample measurement data from a measurement of the plurality of objects, a spectrometer ID associated with the sample measurement data, corresponding spectrometer calibration data associated with the spectrometer ID, cover measurement data, a cover ID, corresponding cover calibration data associated with the cover ID, an accessory measurement data, an accessory ID, or corresponding accessory calibration spectral data associated with the accessory ID.

4. An apparatus as in claim 1, wherein the processor comprises a remote processor configured to receive sample measurement data from a measurement of the plurality of objects, a spectrometer ID associated with the measurement data of the plurality of objects, corresponding spectrometer calibration spectral data associated with the spectrometer ID, cover measurement data, a cover ID, corresponding cover calibration spectral data associated with the cover ID, accessory measurement data, an accessory ID, and corresponding accessory calibration spectral data associated with the accessory ID.

5. An apparatus as in claim 1, wherein the processor is configured with instructions to,
determine the plurality of objects in response to the spectral data and the unique identification code for each of the plurality of calibration covers.

6. An apparatus as in claim 1, wherein the processor is configured with instructions to receive a unique identification code for each of the plurality of spectrometers and measure the spectrum in response to the unique identification code for each of the plurality of calibration covers and the unique identification code for each of the plurality of spectrometers.

7. An apparatus as in claim 1, wherein the processor is configured with instructions to,
measure the spectrum of the plurality of objects in response to the unique identification code for each of the plurality of calibration covers.

8. An apparatus as in claim 1, further comprising:
the plurality of spectrometers to measure the spectral data of the plurality of objects; and
a plurality of accessories for each of the plurality of spectrometers, each of the plurality of accessories having the unique identification code; and
wherein the processor is configured with instructions to associate the unique identification code for each of the plurality of accessories with the plurality of spectrometers and transmit the unique identification code for each of the plurality of accessories and the spectral data to a remote processor.

9. The apparatus of claim 8, wherein the processor is configured with instructions to store a unique identification code for each of the plurality of spectrometers and associate the unique identification code for each of the plurality of spectrometers with the unique identification code for each of the plurality of accessories.

10. An apparatus as in claim 8, wherein the processor is configured to transmit one or more of sample measurement data from a measurement of the plurality of objects, a spectrometer ID associated with the sample measurement data, corresponding spectrometer calibration spectral data associated with the spectrometer ID, cover measurement data, a cover ID, corresponding cover calibration spectral data associated with the cover ID, accessory measurement data, an accessory ID, or corresponding accessory calibration spectral data associated with the accessory ID.

11. An apparatus as in claim 1, further comprising:
the plurality of spectrometers to measure the spectral data of the plurality of objects; and
the plurality of calibration covers for the plurality of spectrometers, each of the plurality of calibration covers having a unique identification code; and
wherein the processor is configured with instructions to associate the unique identification code for each of the plurality of calibration covers with the plurality of spectrometers and transmit the unique identification code for each of the plurality of calibration covers and the spectral data to a remote processor.

12. The apparatus of claim 11, wherein the processor is configured with instructions to store a unique identification code for each of the plurality of spectrometers and associate the unique identification code for each of the plurality of spectrometers with the unique identification code for each of the plurality of calibration covers.

13. An apparatus as in claim 11, wherein the processor is configured to transmit one or more of sample measurement data from a measurement of the plurality of objects, a spectrometer ID associated with the sample measurement data, corresponding spectrometer calibration spectral data associated with the spectrometer ID, cover measurement data, a cover ID, corresponding cover calibration spectral data associated with the cover ID, accessory measurement data, an accessory ID, or corresponding accessory calibration spectral data associated with the accessory ID.

14. An apparatus as in claim 1, further comprising:
the plurality of spectrometers;
a display; and
wherein a local processor is coupled to the display, wherein the local processor is configured to store a unique identification code for each of the plurality of spectrometers, and wherein the local processor is configured with instructions to receive the spectral data from a remote processor in response to the unique identification code for each of the plurality of spectrometers and display the spectral data.

15. A method of measuring spectra of a plurality of samples, the method comprising:
receiving a unique identification code for each of a plurality of calibration covers associated with a plurality of spectrometers, wherein said unique identification code for each of the plurality of calibration covers is independent of the respective spectrometer associated with the respective calibration cover,
receiving spectral data from each of the plurality of spectrometers, and
generating spectra of a plurality of samples in response to sample measurement data, a plurality of spectrometer identification codes, and a plurality of spectrometer calibration data associated with the plurality of spectrometer identification codes.

16. The method of claim 15, further comprising:
generating spectrometer calibration spectra of a handheld spectrometer, by measuring a reference material with the handheld spectrometer;
assigning a spectrometer identification code to the handheld spectrometer;
storing the spectrometer calibration spectra and the spectrometer identification code to a database; and
measuring a sample using the handheld spectrometer to generate sample measurement data.

17. The method of claim 16, wherein steps of generating the spectrometer calibration spectra and assigning the spectrometer identification code are performed during production of the handheld spectrometer.

18. The method of claim 16, further comprising:
generating cover calibration spectra of the plurality of calibration covers, by measuring a calibration material of the plurality of calibration covers using a reference spectrometer;
assigning a cover identification code to each of the plurality of calibration covers;
storing the cover calibration spectra and the cover identification code to the database;
measuring the calibration material of the plurality of calibration covers using the handheld spectrometer, before or after the measurement of the sample, to generate cover measurement data; and generating the spectra of the plurality of samples further in response to the cover measurement data, the cover identification code, and the cover calibration spectra associated with the cover identification code.

19. The method of claim 18, wherein steps of generating the calibration spectra of the plurality of calibration covers and assigning the cover identification code are performed during production of the plurality of calibration covers.

20. The method of claim 16, further comprising:
generating accessory calibration spectra of an accessory, by measuring a reference material of the accessory using a reference spectrometer;
assigning an accessory identification code to the accessory;
storing the accessory calibration spectra and the accessory identification code to the database;
measuring the reference material of the accessory using the handheld spectrometer, before or after the measurement of the sample, to generate accessory measurement data; and
generating the spectra of the plurality of samples further in response to the accessory measurement data, the accessory identification code, and the accessory calibration spectra associated with the accessory identification code.

21. The method of claim 20, wherein steps of generating the calibration spectra of the accessory and assigning the accessory identification code are performed during production of the accessory.

* * * * *